US009359282B2

(12) United States Patent
Badea et al.

(10) Patent No.: US 9,359,282 B2
(45) Date of Patent: *Jun. 7, 2016

(54) FUNCTIONALIZED NANODIAMONDS AS DELIVERY PLATFORMS FOR NUCLEIC ACIDS

(71) Applicant: University of Saskatchewan, Saskatoon (CA)

(72) Inventors: Ildiko Badea, Saskatoon (CA); Ronald Verrall, Saskatoon (CA); Jackson M. Chitanda, Saskatoon (CA); Randeep Kaur, Saskatoon (CA); Saniya Alwani, Saskatoon (CA)

(73) Assignee: University of Saskatchewan, Saskatoon, Saskatchewan (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/255,001

(22) Filed: Apr. 17, 2014

(65) Prior Publication Data

US 2014/0314850 A1    Oct. 23, 2014

Related U.S. Application Data

(60) Provisional application No. 61/813,913, filed on Apr. 19, 2013, provisional application No. 61/847,256, filed on Jul. 17, 2013.

(30) Foreign Application Priority Data

Jul. 17, 2013 (CA) ..................................... 2821348

(51) Int. Cl.
| | |
|---|---|
| *A61K 47/48* | (2006.01) |
| *A61K 31/4172* | (2006.01) |
| *C12N 15/113* | (2010.01) |
| *C07C 59/68* | (2006.01) |
| *C07C 255/41* | (2006.01) |
| *C07C 59/52* | (2006.01) |
| *H01J 49/00* | (2006.01) |
| *A61K 31/196* | (2006.01) |
| *A61K 48/00* | (2006.01) |
| *C01B 31/06* | (2006.01) |
| *H01J 49/16* | (2006.01) |
| *B82Y 5/00* | (2011.01) |

(52) U.S. Cl.
CPC ............... *C07C 59/68* (2013.01); *A61K 31/196* (2013.01); *A61K 31/4172* (2013.01); *A61K 47/48884* (2013.01); *A61K 48/0008* (2013.01); *C01B 31/065* (2013.01); *C07C 59/52* (2013.01); *C07C 255/41* (2013.01); *C12N 15/113* (2013.01); *H01J 49/0027* (2013.01); *H01J 49/164* (2013.01); *B82Y 5/00* (2013.01); *C07B 2200/11* (2013.01); *C07C 2104/00* (2013.01); *Y10T 428/2982* (2015.01); *Y10T 436/143333* (2015.01)

(58) Field of Classification Search
None
See application file for complete search history.

(56) References Cited

U.S. PATENT DOCUMENTS

| | | | |
|---|---|---|---|
| 7,326,837 | B2 | 2/2008 | Han et al. |
| 9,012,838 | B2 * | 4/2015 | El-Aneed ............... C07C 255/41 166/228 |
| 2005/0158548 | A1 | 7/2005 | Senga |
| 2005/0158549 | A1 | 7/2005 | Khabashesku et al. |
| 2009/0226495 | A1 | 9/2009 | Picardi |
| 2011/0006218 | A1 | 1/2011 | Mochalin et al. |
| 2011/0008447 | A1 | 1/2011 | Chao et al. |
| 2011/0252713 | A1 | 10/2011 | Chakraborty et al. |
| 2012/0271361 | A1 | 10/2012 | Zhou |
| 2014/0312218 | A1 * | 10/2014 | El-Aneed et al. ............. 250/282 |

FOREIGN PATENT DOCUMENTS

| | | |
|---|---|---|
| CA | 2692017 | 3/2009 |
| CA | 2795932 | 10/2011 |
| CA | 2796057 | 10/2011 |
| WO | 2011/130023 A2 | 10/2011 |
| WO | 2011130023 | 10/2011 |

OTHER PUBLICATIONS

Kauer et al (International Journal of Nanomedicine (2013) 8: 203-220).*
Kruger et al (J Mater Chem. 2006;16(24):2322-2328) cited in Specification on p. 75, item No. 25.*
Kauer 2012. (Jul. 18, 2012) International Journal of Nanomedicine, vol. 7, pp. 3851-3866).*
Kauer 2013. (Jan. 8, 2013) International Journal of Nanomedicine, vol. 8, pp. 203-220).*
Cohen, Lucinda H., et al., "Small Molecule Analysis by MALDI Mass Spectrometry", Anal Bioanal Chem. 2002, 373, pp. 571-586.
Cohen, Lucinda, et al., "Small-Molecule Desorption/Ionization Mass Analysis", MALDI MS, A Practical Guide to Instrumentation, Methods and Applications, 2007, pp. 299-337.
Kaur, Randeep, et al, "Lysine-functionalized nanodiamonds: synthesis, physiochemical characterization, and nucleic acid binding studies", International Journal of Nanomedicine, 2012:7, pp. 3851-3866.
Kaur, Randeep, et al., "Nanodiamonds as novel nanomaterials for biomedical applications: drug delivery and imaging systems", International Journal of Nanomedicine, 2013:8, pp. 203-220.

(Continued)

*Primary Examiner* — Marcela M Cordero Garcia
*Assistant Examiner* — Mindy Newman
(74) *Attorney, Agent, or Firm* — Bereskin & Parr LLP/S.E.N.C.R.L., s.r.l.; Patricia Folkins

(57) ABSTRACT

The present application relates to functionalized nanodiamonds, to complexes comprising a functionalized nanodiamond reversibly bound to a nucleic acid and to compositions comprising such functionalized nanodiamonds and complexes. In particular, the functionalized nanodiamonds comprise at least one naturally occurring basic amino acid, or analogs or derivatives thereof, covalently linked to a nanodiamond. The present application also includes methods and uses of the complexes and compositions, for example for delivering a nucleic acid to a cell.

19 Claims, 23 Drawing Sheets

(56) References Cited

OTHER PUBLICATIONS

Pham, M.D., et al, "Improved Mass Spectrometic Analysis of Membrane Proteins based on Rapid and Versatile Sample Preparation on Nanodiamond Particles", Analytical Chemistry, vol. 85, Issue 14, Jul. 16, 2013, pp. 6748-6755.

Krueger, Anke et al, "Bitonylated Nanodiamond: Simple and Efficient Functionalization of Detonation Diamond", Langmuir, 2008, 24(8), pp. 4200-4204, Mar. 1, 2008.

Liu, Yu, et al., "Functionalization of Nanoscale Diamond Powder: Fluoro- Alkyl-, Amino-, and Amino Acid-Nanodiamond Derivatives", Chem. Mater., 2004, 16(2)), pp. 3294-3930, Sep. 2, 2004.

* cited by examiner

FUNCTIONALIZED NANODIAMONDS AS DELIVERY PLATFORMS FOR NUCLEIC ACIDS

CROSS-REFERENCE TO RELATED APPLICATIONS

The present application claims the benefit of priority from U.S. provisional application Nos. 61/813,913 and 61/847,256 filed on Apr. 19, 2013 and Jul. 17, 2013, respectively, and Canadian patent application no. 2,821,348 filed on Jul. 17, 2013, the contents of each of which are incorporated herein by reference in their entirety.

FIELD

The present application relates to functionalized nanodiamonds comprising at least one naturally occurring basic amino acid covalently linked to a nanodiamond and to complexes comprising such functionalized nanodiamonds, said complexes comprising the functionalized nanodiamond reversibly bound to a nucleic acid. The present application also includes methods and uses of the complexes and compositions, for example for delivering a nucleic acid to a cell.

BACKGROUND

Nanodiamonds are carbon-based nanomaterials with an inert sp³ hybridized carbon core. In recent years, the scientific community has become increasingly interested in detonation nanodiamonds (NDs) because of their useful structural, mechanical, chemical, optical, and/or biological characteristics.[1] NDs were first produced in Russia in the 1960s through the incomplete combustion of carbon-containing explosives.[2] Detonation nanodiamonds are produced by the detonation of 2,4,6-trinitrotoluene (TNT) and Hexogen (RDX) in a closed system in the absence of oxygen. These diamond nanoparticles initially attracted the attention of the industrial world and they have been used, for example in the electrochemical coating of metals and to improve the physical properties of polymers and the shelf life of mechanical tools.[3] Investigations into their nanoscale properties have recently studied certain biological applications.[4,5,6]

An attractive feature of NDs is their uniform nanoscale size distribution. The primary particle size of a ND ranges from 4 to 5 nm,[1,7,8] with a chemically inert diamond core and a shell comprising sp²-hydridized carbon structures.[9] Various oxygen-containing functional groups are found on the surface of NDs,[8,10,11] such as carboxyl, hydroxyl, lactone, anhydride, ketone and ether[12] opening the potential for their conjugation with biochemical moieties. Upon oxidation, carboxylated nanodiamonds are obtained (Scheme 1). On the other hand, reduction processes introduce hydroxyl groups on the surface, as shown below in Scheme 1. Such oxidized or reduced forms of the nanodiamonds allow for variation in the possibilities of what can be grafted on the nanodiamond surface.[13,14] Surface modifications of NDs can be achieved through either a physical or a covalent (for example, amide or ester bonding) interaction.

Scheme 1

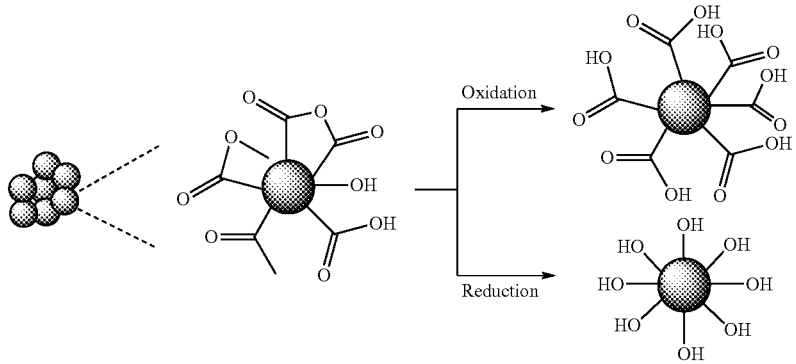

Physical adsorption of NDs has been reported using toxins,[15] proteins,[16,17] chemotherapeutic drugs,[5,6,18] and nucleic acids.[19,20] Carboxylic[21,22] and nitrogen-containing[23] functional groups have been grafted onto NDs using a radical generation mechanism, while alkyl-, amino-, and amino acid-functionalized nanodiamonds have been prepared through the chemical modification of fluorinated NDs with alkyl lithium, ethylenediamine, or glycine ethyl ester hydrochloride, respectively.[24] NDs have also been functionalized with amino acids[25] and alkyl chains[26] via covalent bonding.

NDs have been found to be biocompatible with various cell lines,[18,27,28] and they generally exhibit lower cytotoxicity than other carbon-based nanomaterials such as single- and multi-walled carbon nanotubes and carbon black.[27,28] As such, they have been assessed for their ability to act as vectors for the intracellular delivery of drugs and biochemical molecules. It has been shown that the hydrophilic nature of NDs is responsible for improving the aqueous solubility of chemotherapeutic and anti-inflammatory drugs that have initially showed poor solubility in water.[29] Chemotherapeutic drugs such as doxorubicin[5] and 10-hydroxycamptothecin[6] have been successfully delivered into cancer cells after being bound to NDs.

Polymer-coated NDs have been reported to improve the delivery of plasmid DNA (pDNA)[19] and small interfering RNA (siRNA)[29] into cellular systems. Contrary to self-assembling nanoparticles, NDs are useful in such applications because of their resistance to biological environmental changes, which could improve the overall delivery of an attached biomolecule.

Despite the promise NDs show as vectors for delivering small chemical drugs and large biotechnology products, it remains a challenge to obtain nanosized ND particles in laboratory and industrial settings owing to their strong tendency to assemble into micron-sized aggregates when dispersed in a polar liquid medium. As these aggregates have the potential to block capillaries, which could lead to toxic effects in the body,[30] the maintenance of dispersion stability of NDs is an important requirement when developing drug delivery formulations.

One way in which dispersion stability can be improved is through the use of chemical modifications such as fluorination[24] and biotinylation.[31] These methods have been shown to reduce the size of ND aggregates from micrometer sizes to 160[24] and 170 nm,[31] respectively.

While a variety of mechanical disaggregation approaches have also been explored, stirred media milling and bead-assisted probe sonication were the most successful in achieving high dispersion stability and producing single-digit nanometer particle sizes.[32] However, while primary-sized NDs may be attained by high-energy bead-assisted probe sonication, the potential for the contamination of samples with sonotrode material when using this technique[32] is unacceptable in life science applications.

To the best of the inventors' knowledge, no previous reported studies are known which have examined the disaggregation of NDs to particles less than 50 nm in size using a simple mechanochemical technique that can be applied at a laboratory level.

SUMMARY

A procedure for covalently bonding basic amino acids, such as lysine and histidine, to detonated nanodiamonds (ND) to obtain basic amino acid-functionalized nanodiamonds has been developed. Lysine-functionalized NDs as well as lysine/histidine-functionalized NDs were prepared. The lysine-functionalized NDs were found to bind plasmid DNA (specifically, pGTCMV.IFN-GFP) and small interfering RNA (specifically, anti-GFP siRNA) through electrostatic interactions. The basic amino acid-functionalized NDs were observed to interact with cells, and laser scanning confocal microscopic measurements and flow cytometry measurements showed cellular internalization of the basic amino acid-functionalized NDs. The basic amino acid-functionalized NDs also showed negligible cytotoxicity, remaining biocompatible from concentrations of 4 to 250 μg/mL in HeLa cells. A basic amino acid-functionalized ND-siRNA complex was observed to deliver siRNA to the cytoplasm of a cell.

Accordingly, the present application includes a functionalized nanodiamond comprising at least one naturally occurring basic amino acid, or an analog or derivative of a naturally occurring basic amino acid, or an acid addition salt thereof, covalently linked to a nanodiamond.

In an embodiment, the at least one naturally occurring basic amino acid is selected from selected from arginine, histidine and lysine, and analogs and derivatives thereof, or acid addition salts thereof.

The present application also includes a composition comprising a functionalized nanodiamond of the application and a carrier.

Also included is a complex comprising a functionalized nanodiamond of the application reversibly bound to a nucleic acid, as well as a composition comprising the complex and a carrier. In an embodiment, the composition is a pharmaceutical composition. In another embodiment, the composition is a vaccine composition The present application also includes a method for delivering a nucleic acid to a cell, comprising administering a complex of the application or a composition of the application to the cell, as well as a use of a complex of the application or a composition of the application for delivering a nucleic acid to a cell.

The present application also includes a method for treating a disease, disorder or condition comprising administering a complex of the application, a pharmaceutical composition of the application or a vaccine composition of the application to a subject in need thereof. In an embodiment, the disease, disorder or condition is treatable using nucleic acids (e.g. gene therapy, antisense therapy, or RNA interference).

The present application also includes a method of eliciting an immune response in a subject in need thereof, comprising administering a complex of the application or a vaccine composition of the application to the subject.

One advantage of the nanodiamond-based systems of the present application compared to other viral and non-viral nucleic acid delivery systems is their safety. Viral vectors, albeit highly efficient, pose a series of safety issues, including immune reactions. The majority of non-viral systems are based on cationic lipids and polymers; these agents also possess some intrinsic toxicity. Nanodiamonds are extremely stable physically and chemically. Their performance is less influenced by environmental factors, compared to organic cations (lipids and polymers).

The large active surface area of nanodiamonds opens the possibility of functionalization with naturally occurring basic amino acids in monolayer or multilayer arrangements on the nanodiamond. In addition, the presence of naturally occurring neutral and/or acidic amino acids, and/or analogs or derivative thereof, for example covalently attached to the nanodiamonds or present as an intermediate layer, can modulate the binding of the nucleic acids, improving the intracellular delivery and release of the genetic material inside the cell in the vicinity of the nucleus. Further, the possibility of attachment of targeting peptides can further improve tissue and cell-specific delivery contributing to increased efficiency and lower systemic toxicity of the nanodiamond complexes of the present application.

Other features and advantages of the present application will become apparent from the following detailed description. It should be understood; however, that the scope of the claims should not be limited by the embodiments set forth in the examples, but should be given the broadest interpretation consistent with the description as a whole.

BRIEF DESCRIPTION OF THE DRAWINGS

The present application will now be described in greater detail with reference to the drawings, in which.

(B) second derivatives of all spectra. A total of 512 individual interferograms were collected and averaged for each sample. The featureless region between wave numbers of 2700 and 1900 cm$^{-1}$ is not shown.

Figure 3:
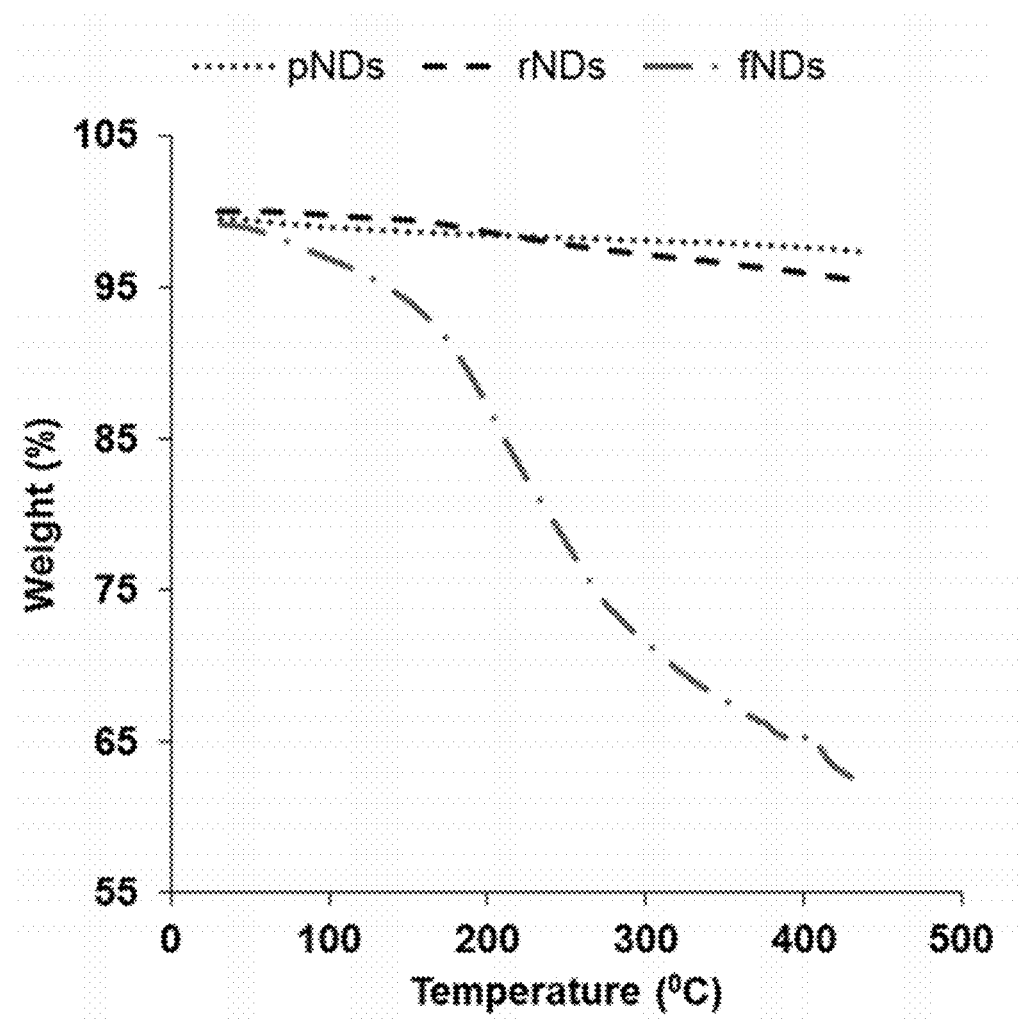

FIG. 3 shows thermograms of pristine carboxylated nanodiamonds (pNDs), reoxidized nanodiamonds (rNDs), and lysine-functionalized nanodiamonds (fNDs) in exemplary embodiments of the present application.

Figure 4:
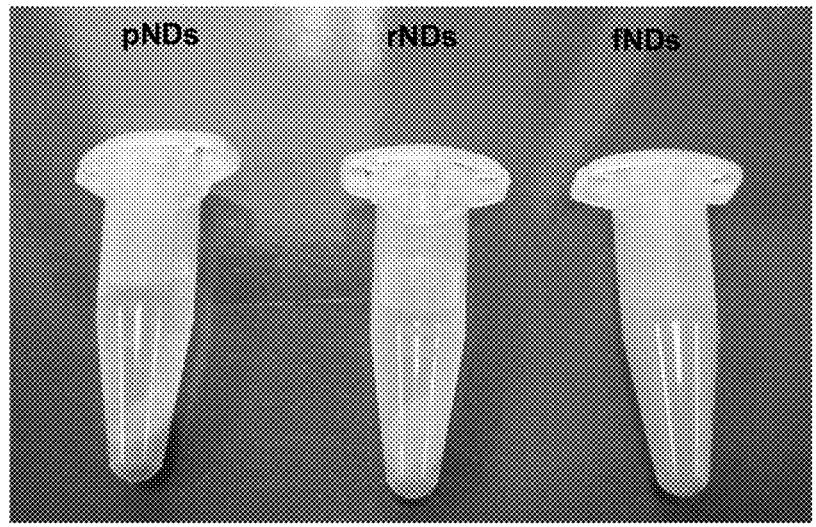

FIG. 4 shows exemplary dispersions of 2 mg/mL nanodiamonds (NDs) in water after 20 minutes of conventional bath sonication and 3-day incubation. Abbreviations: pNDs, pristine carboxylated nanodiamonds; rNDs, re-oxidized nanodiamonds; fNDs, lysine-functionalized nanodiamonds.

Figure 5:
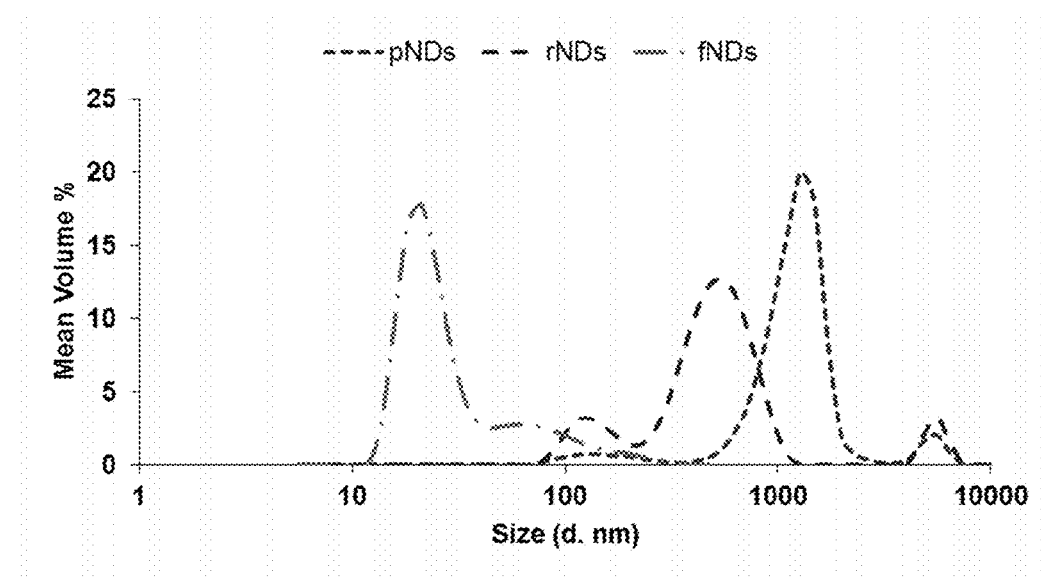

FIG. 5 shows exemplary size distributions of pristine carboxylated nanodiamonds (pNDs), reoxidized nanodiamonds (rNDs), and lysine-functionalized nanodiamonds (fNDs) in water, as measured by dynamic light scattering. Each curve is derived from three measurements (n≥10).

Figure 6:
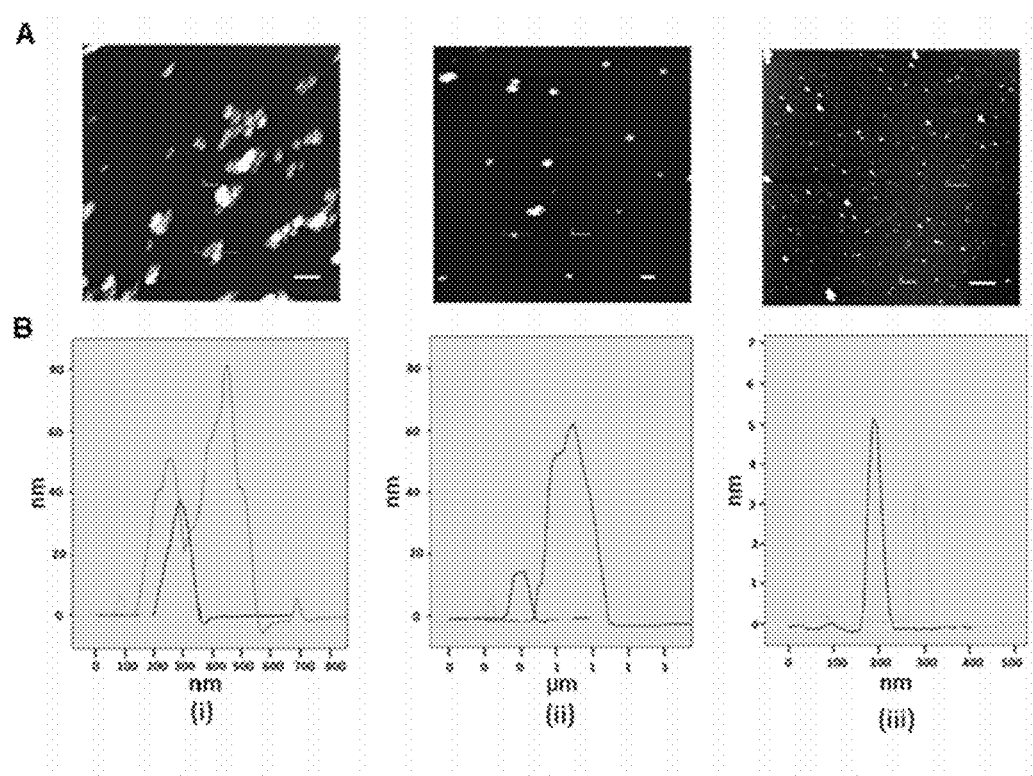

FIG. 6 shows (A) intermittent contact mode atomic force microscopy topographic images of nanodiamond samples in exemplary embodiments of the present application and (B) line-scan profiles of the particles indicated in each image. From left to right: (i) pristine carboxylated, (ii) reoxidized, and (iii) lysine-functionalized nanodiamonds. The bar (solid white line) represents 500 nm.

Figure 7:
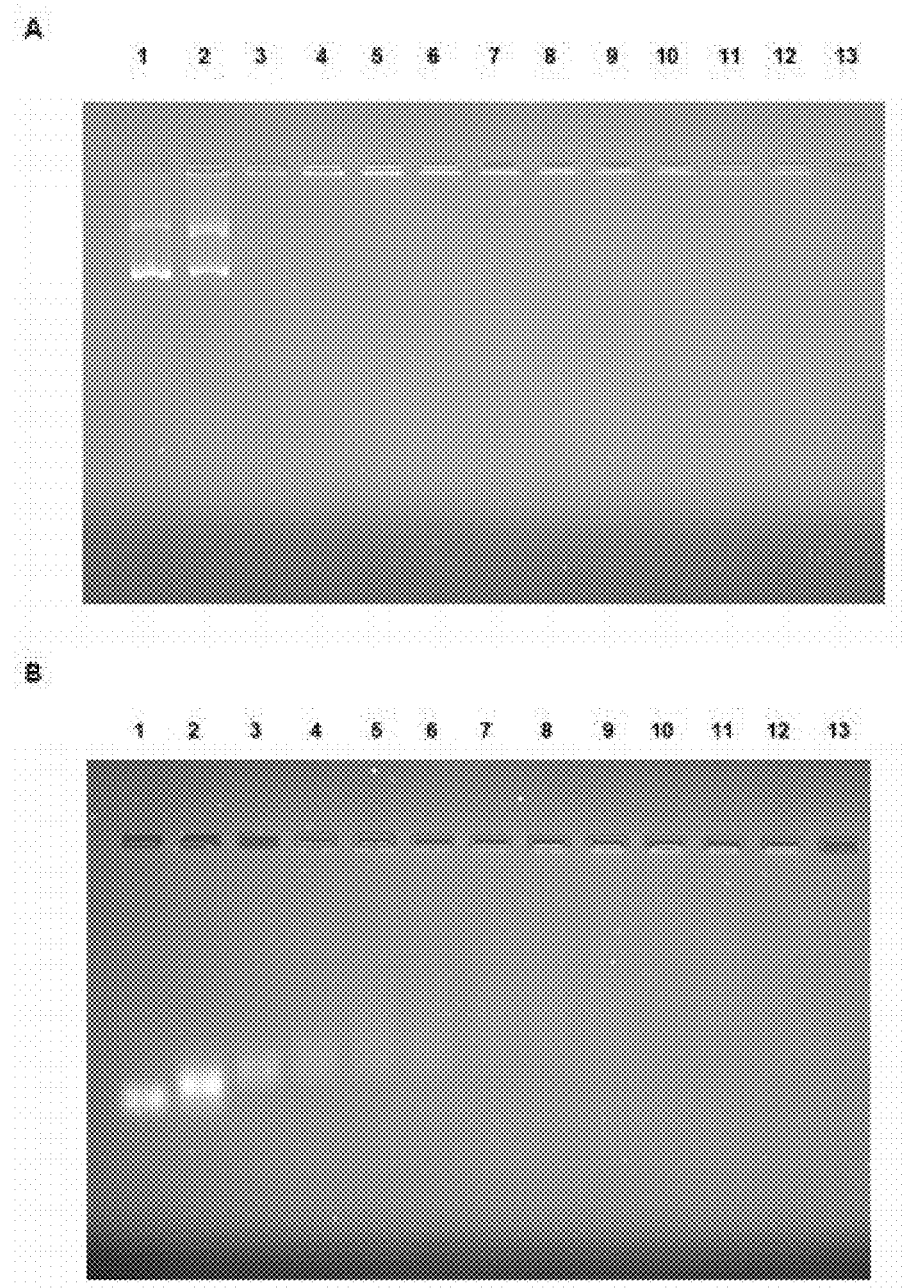

FIG. 7 shows results of agarose gel electrophoresis of (A) lysine-functionalized nanodiamond (fND)-plasmid DNA in exemplary embodiments of the present application and (B) fND-small interfering RNA complexes ("diamoplexes") with increasing weight ratios of fNDs to nucleic acid in exemplary embodiments of the present application: 1:1 (lane 2), 5:1 (lane 3), 10:1 (lane 4), 15:1 (lane 5), 20:1 (lane 6), 25:1 (lane 7), 30:1 (lane 8), 35:1 (lane 9), 40:1 (lane 10), 45:1 (lane 11), and 50:1 (lane 12). Lane 1 consists of standard nucleic acid only, and lane 13 is empty.

Figure 8:
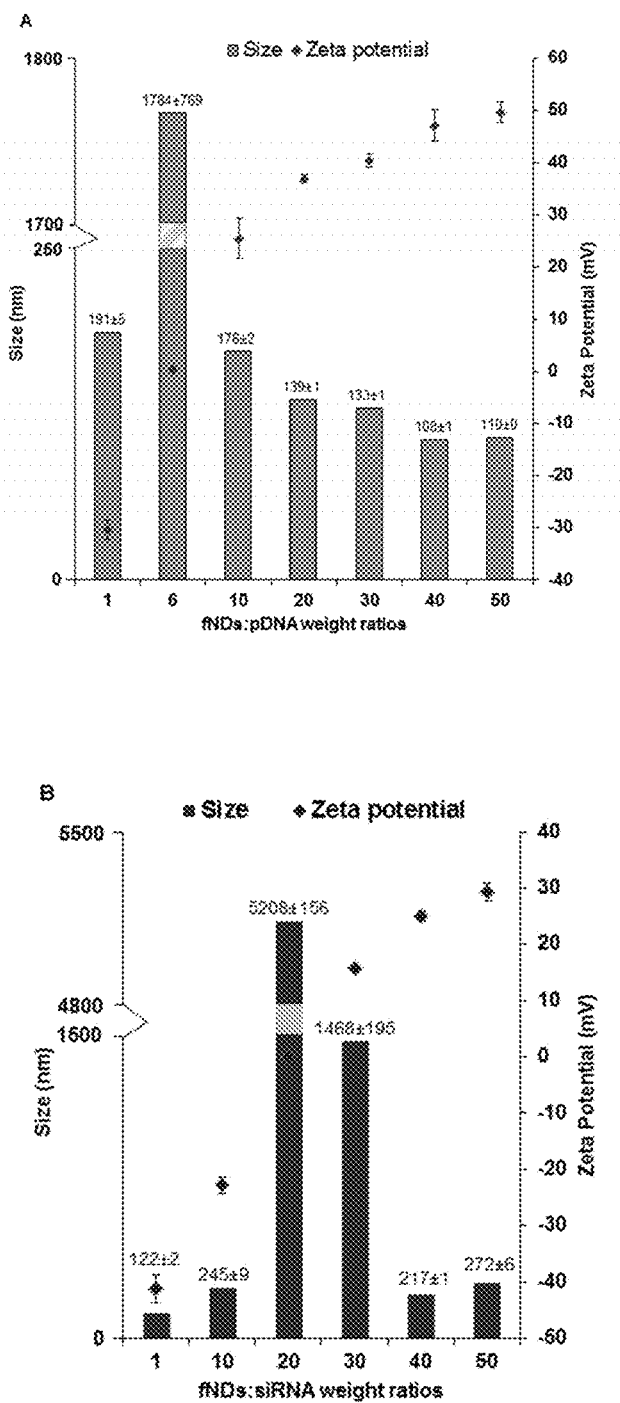

FIG. 8 shows size and zeta potential measurements using various weight ratios of (A) lysine-functionalized nanodiamonds and plasmid DNA (fNDs:pDNA) in exemplary embodiments of the present application and (B) fNDs and small interfering RNA (fNDs:siRNA) in exemplary embodiments of the present application. Each value represents mean plus or minus standard deviation of four measurements (n≥10).

Figure 9:
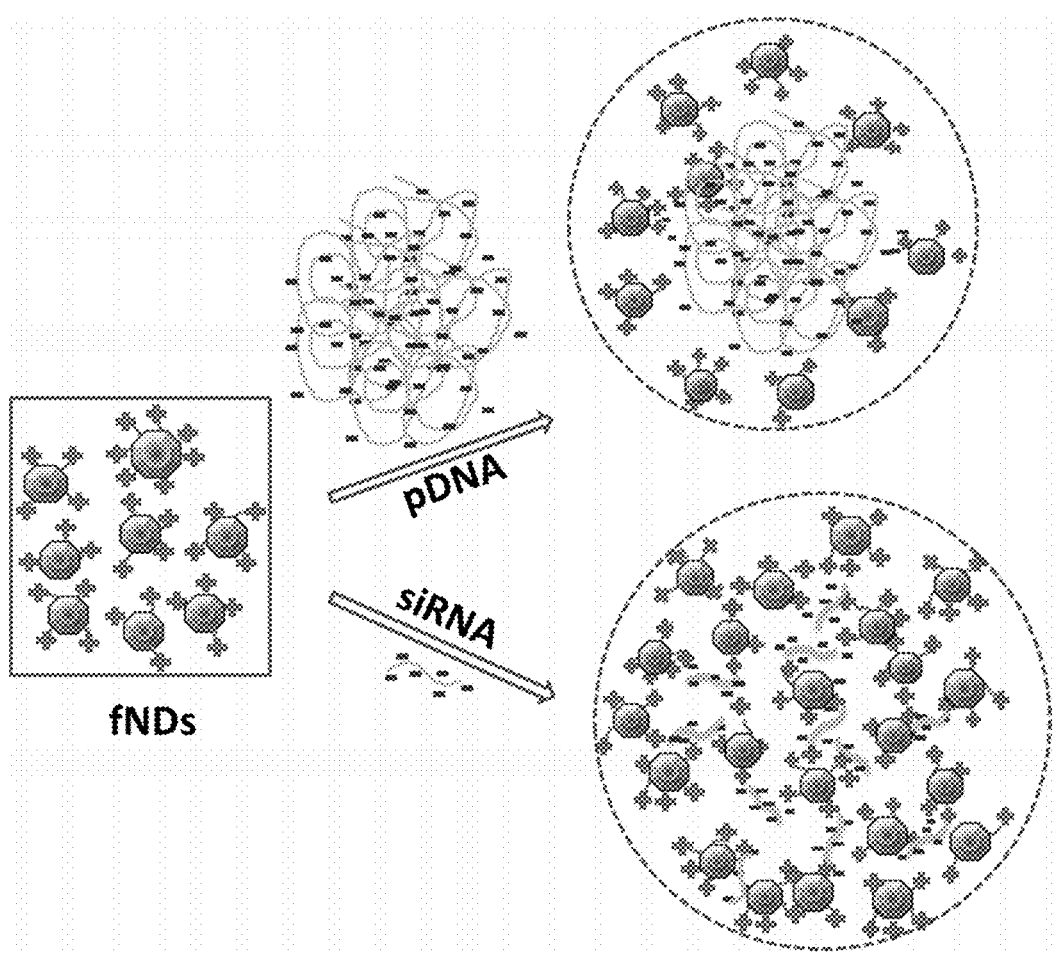

FIG. 9 shows a schematic representation of the different binding behavior of plasmid DNA (pDNA) and small interfering RNA (siRNA) to positively charged lysine-functionalized nanodiamonds (fNDs) in exemplary embodiments of the present application.

Figure 10:
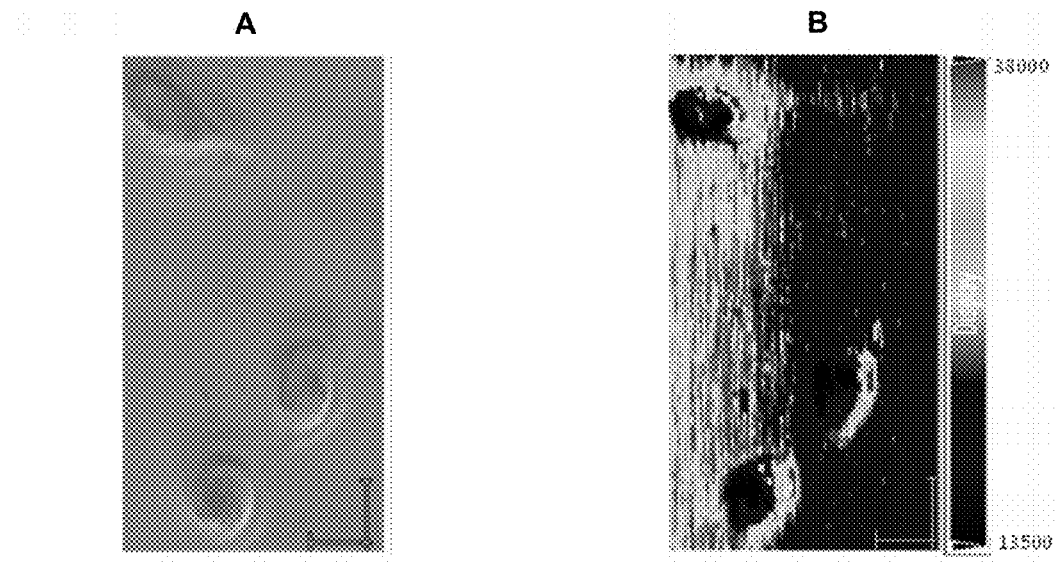

FIG. 10 shows an exemplary white light image and an exemplary backscattering mode map of pristine carboxylated nanodiamond treated cells: (A) white light image; (B) backscatter map constructed using the intensity of elastically scattered light at 1058.22 nm using 0.1% laser intensity source. The colors range from violet (lowest intensity; lower end of bar at the right of FIG. 10B) to red (highest intensity; upper end of bar at the right of FIG. 10B). Each scale bar is 20 μm.

Figure 11:
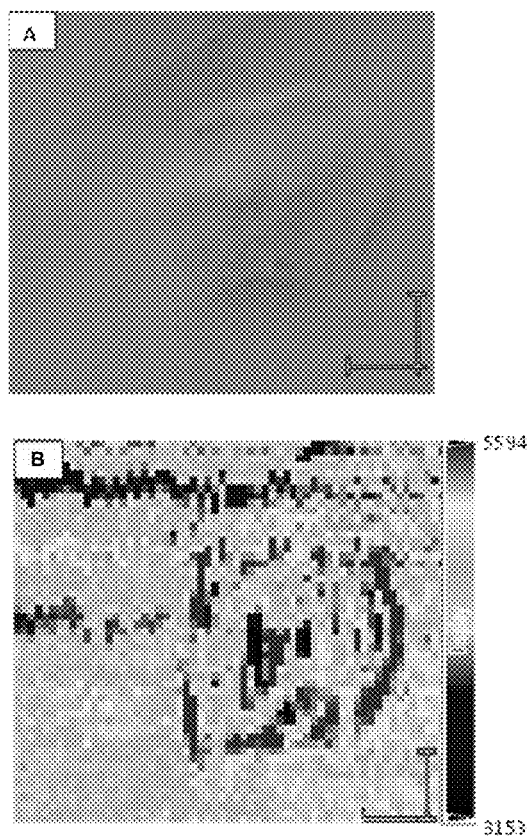

FIG. 11 shows an exemplary white light image and an exemplary backscattering mode map of a lysine-functionalized nanodiamond treated cell: (A) white light image; (B) backscatter map constructed from the intensity of elastically scattered light at 1058.22 nm using 0.05% laser intensity source. The colors range from violet (lowest intensity; lower end of bar at the right of FIG. 11B) to red (highest intensity upper end of bar at the right of FIG. 11B). Each scale bar is 10 μm. Other analyzed cells also showed cellular interaction of lysine-functionalized nanodiamonds with a different pattern (high intensity region located inside the cell rather than near the inner cellular membrane).

Figure 12:
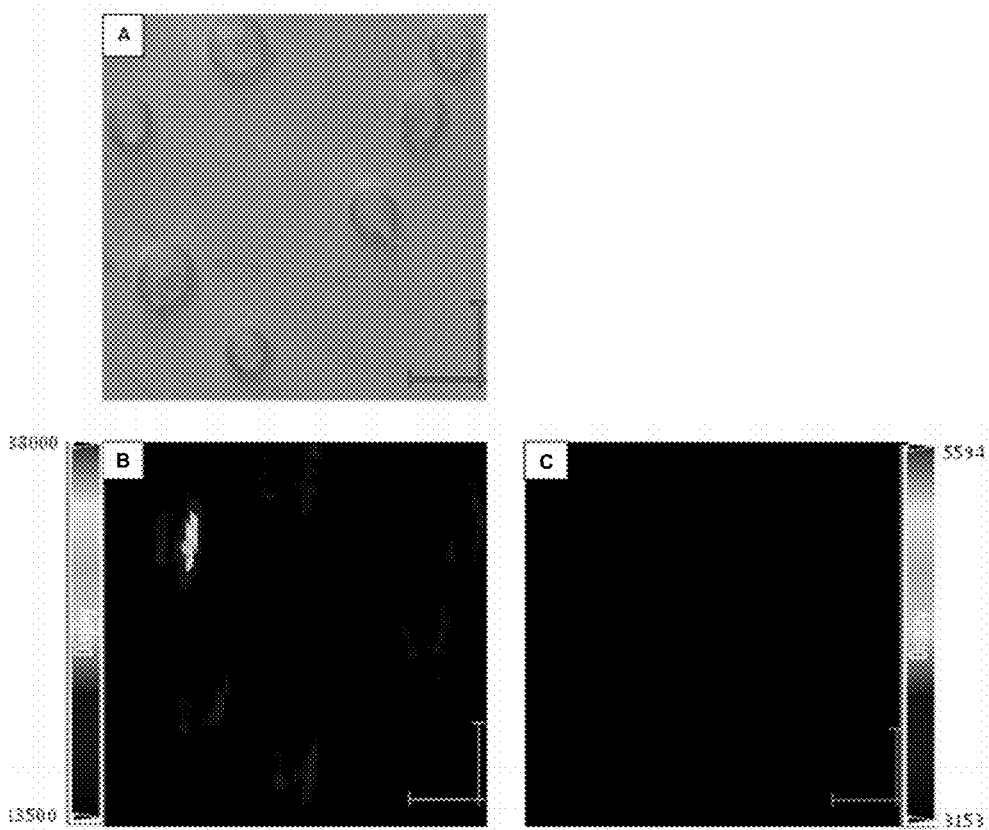

FIG. 12 shows an exemplary white light image and exemplary backscattering mode maps of untreated cells: (A) white light image; (B) backscatter map constructed using the intensity of elastically scattered light at 1058.22 nm using 0.1% laser intensity source (C) backscatter map constructed using the intensity of elastically scattered light at 1058.22 nm using 0.05% laser intensity source. No Raman and backscattering signals are observed in the intensity range of 3400 to 4000 and 3153 to 5594, respectively. In color images, the colors range from violet (lowest intensity; lower end of bars at the left of FIG. 12B and the right of FIG. 12C) to red (highest intensity; upper end of the bars at the left of FIG. 12B and the right of FIG. 12C). Each scale bar is 20 μm.

Figure 13:
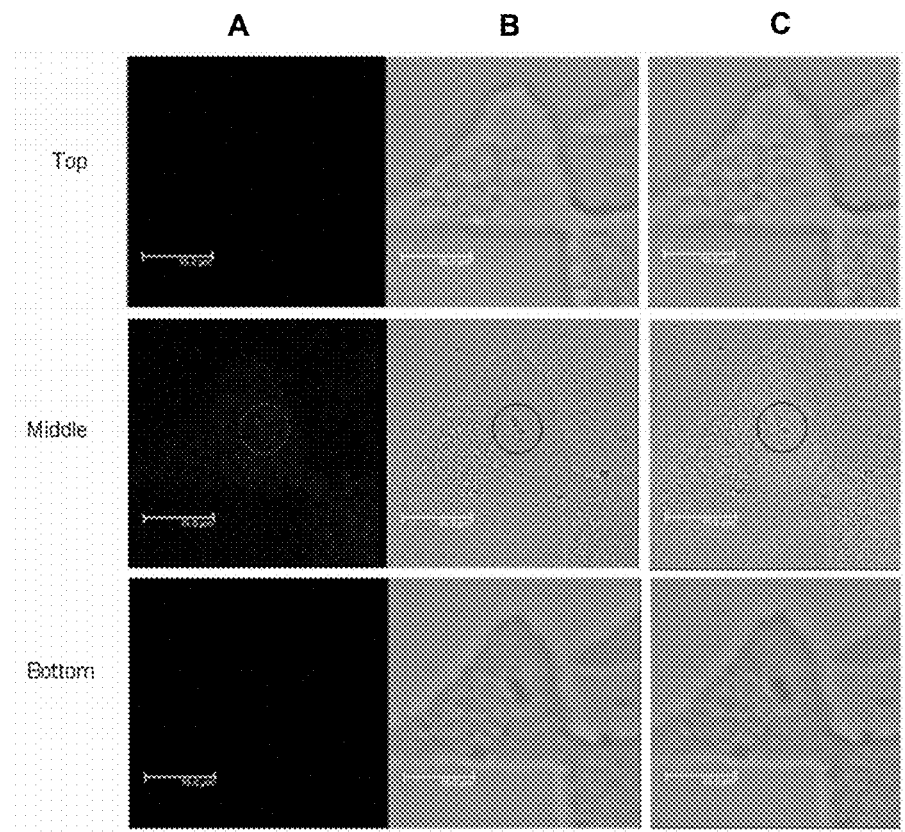

FIG. 13 shows laser scanning confocal microscopic images of a live cell treated with lysine-functionalized nanodiamonds in exemplary embodiments of the present application. Laser scanning confocal microscopic of HeLa cells incubated with lysine-functionalized nanodiamonds for 24 hours: From left to right: (A) fluorescence images, (B) bright field images and (C) overlay of fluorescence and bright field images. Excitation was performed using 476 nm laser and emission was collected from 492 to 677 nm. A total of 44 slices were images with 0.38 μm intervals.

Figure 14:
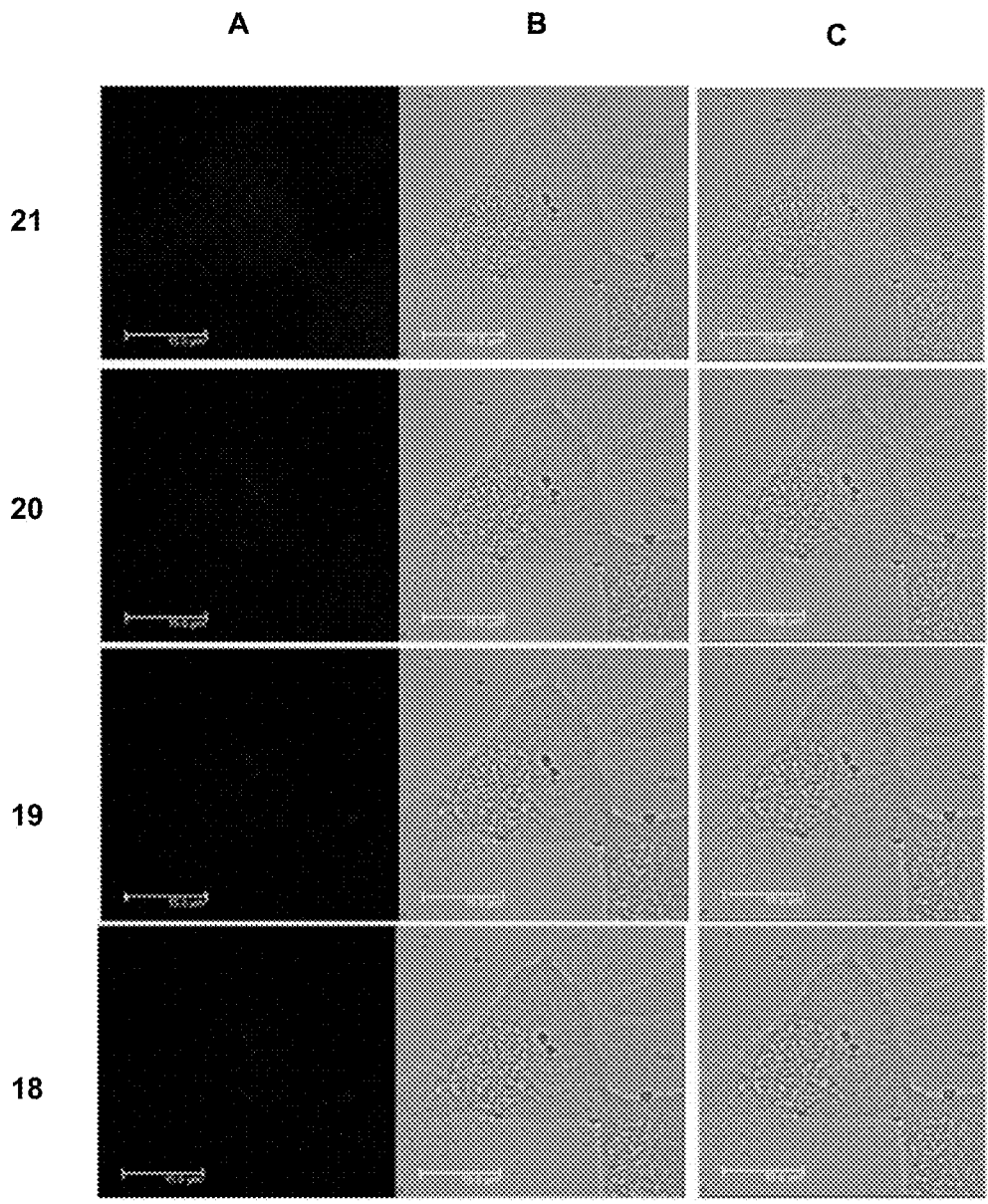

FIG. 14 shows laser scanning confocal microscopic images of four consecutive sections from middle towards the bottom of the cell treated with lysine-functionalized nanodiamonds in exemplary embodiments of the present application. Laser scanning confocal microscopic of four consecutive sections from the middle towards bottom of the HeLa cells incubated with lysine-functionalized nanodiamonds for 24 hours. From left to right; (A) fluorescence images, (B) bright field images and (C) overlay of fluorescence and bright field images. From top to bottom; sections 21, 20, 19 and 18 (intervals of 0.38 μm). Excitation was performed using 476 nm laser and emission was collected from 492 to 677 nm.

Figure 15:
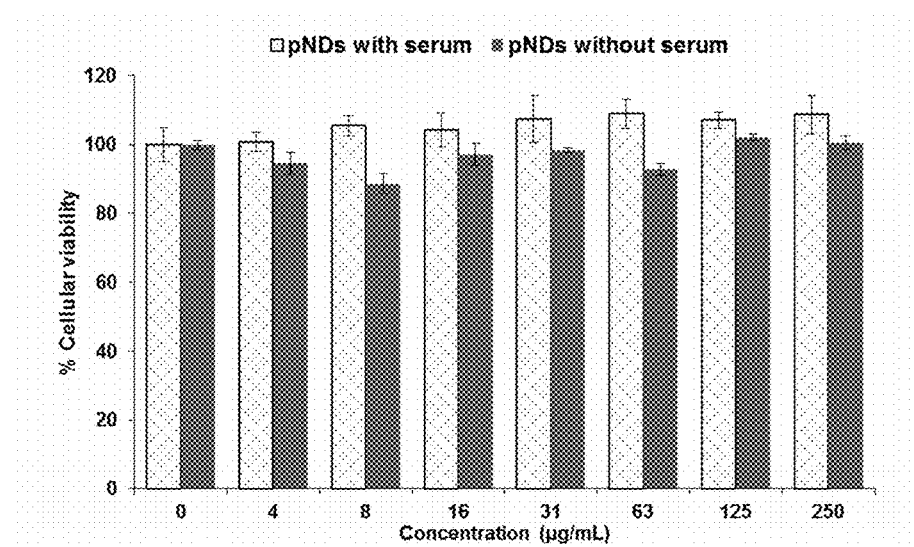

FIG. 15 shows results of a MTT cytotoxicity assay of HeLa cells treated with pristine carboxylated nanodiamonds with and without serum. Evaluation of HeLa cell viability after incubation with 0-250 μg/mL of pristine carboxylated nanodiamonds in the cell culture medium with and without serum for 24 hours as determined by MTT assay. Cells cultured without nanodiamonds were used as controls. Cells treated with pristine carboxylated nanodiamonds did not elicit significant cytotoxic effects when compared to control cells (Scheffé's post-hoc multiple comparison test, p<0.05). Results are expressed as mean±S.E.M., n=3.

Figure 16:
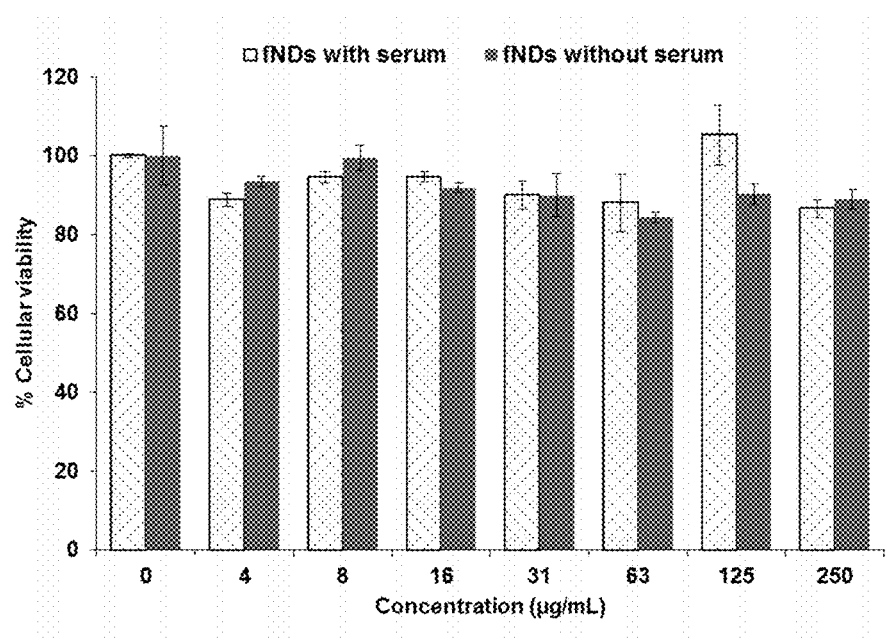

FIG. 16 shows the results of an MTT cytotoxicity assay of HeLa cells treated with lysine-functionalized nanodiamonds with and without serum in exemplary embodiments of the present application. Evaluation of HeLa cell viability after incubation with 0-250 μg/mL of lysine-functionalized nanodiamonds in the cell culture medium with and without serum for 24 hours as determined by MTT assay. Cells cultured without nanodiamonds were used as control group. Cells treated with lysine-functionalized nanodiamonds did not elicit significant cytotoxic effects when compared to control cells (Dunnett's T3 post-hoc multiple comparison test, p<0.05). Results are expressed as mean±S.E.M., n=3.

Figure 17:
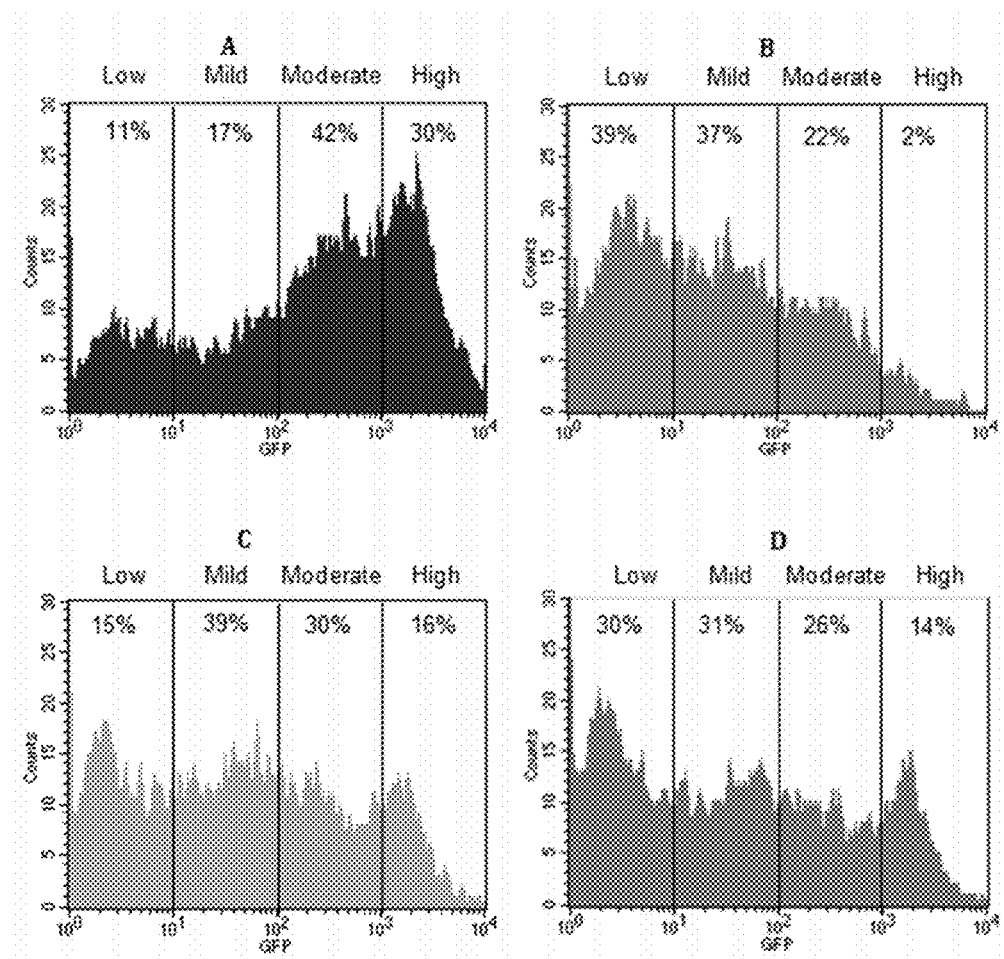

FIG. 17 shows flow cytometer histograms indicating the GFP fluorescence intensity trend in untreated and treated cell populations in exemplary embodiments of the present application. Fluorescence activated cell sorting histograms of (A)

control; (B) Lipofectamine:siRNA transfected; (C) fNDs: siRNA (35:1, w/w) transfected; (D) naked siRNA transfected HeLa/GFP cells.

Figure 18:
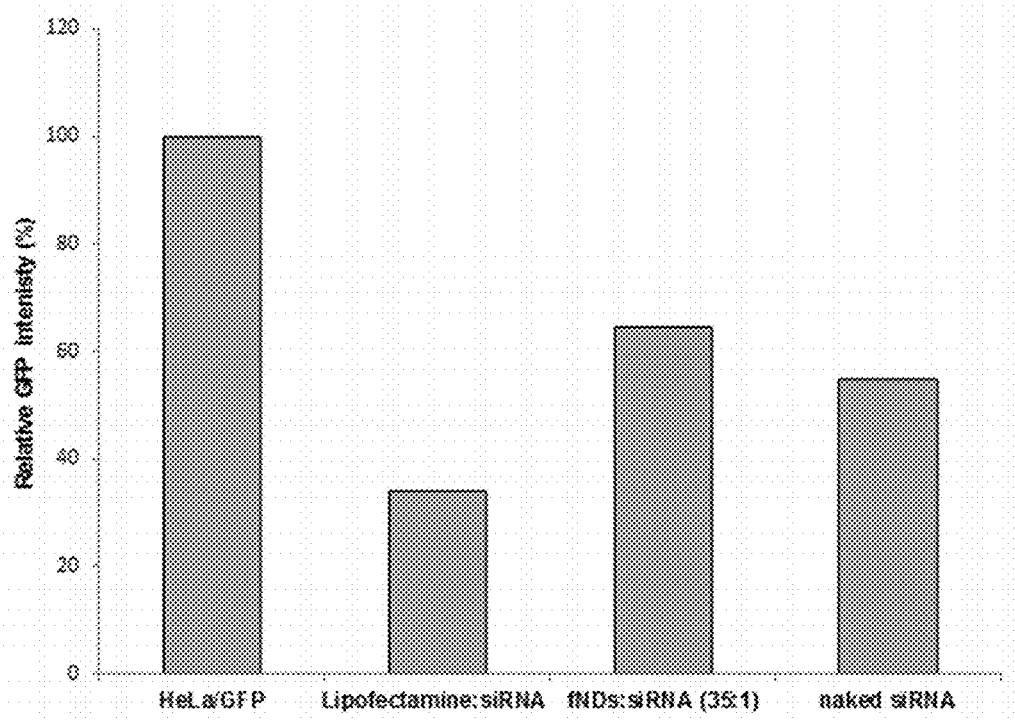

FIG. 18 shows the effect of using lysine-functionalized nanodiamonds to deliver small interfering RNA in exemplary embodiments of the present application. Percentage GFP intensity of control HeLa/GFP cells, Lipofectamine:siRNA, fNDs:siRNA (35:1, w/w) and naked siRNA transfected HeLa/GFP cells. The fluorescence intensity of green fluorescent protein was measured by flow cytometer and is expressed as a percentage relative to the untreated HeLa/GFP cells.

Figure 19:
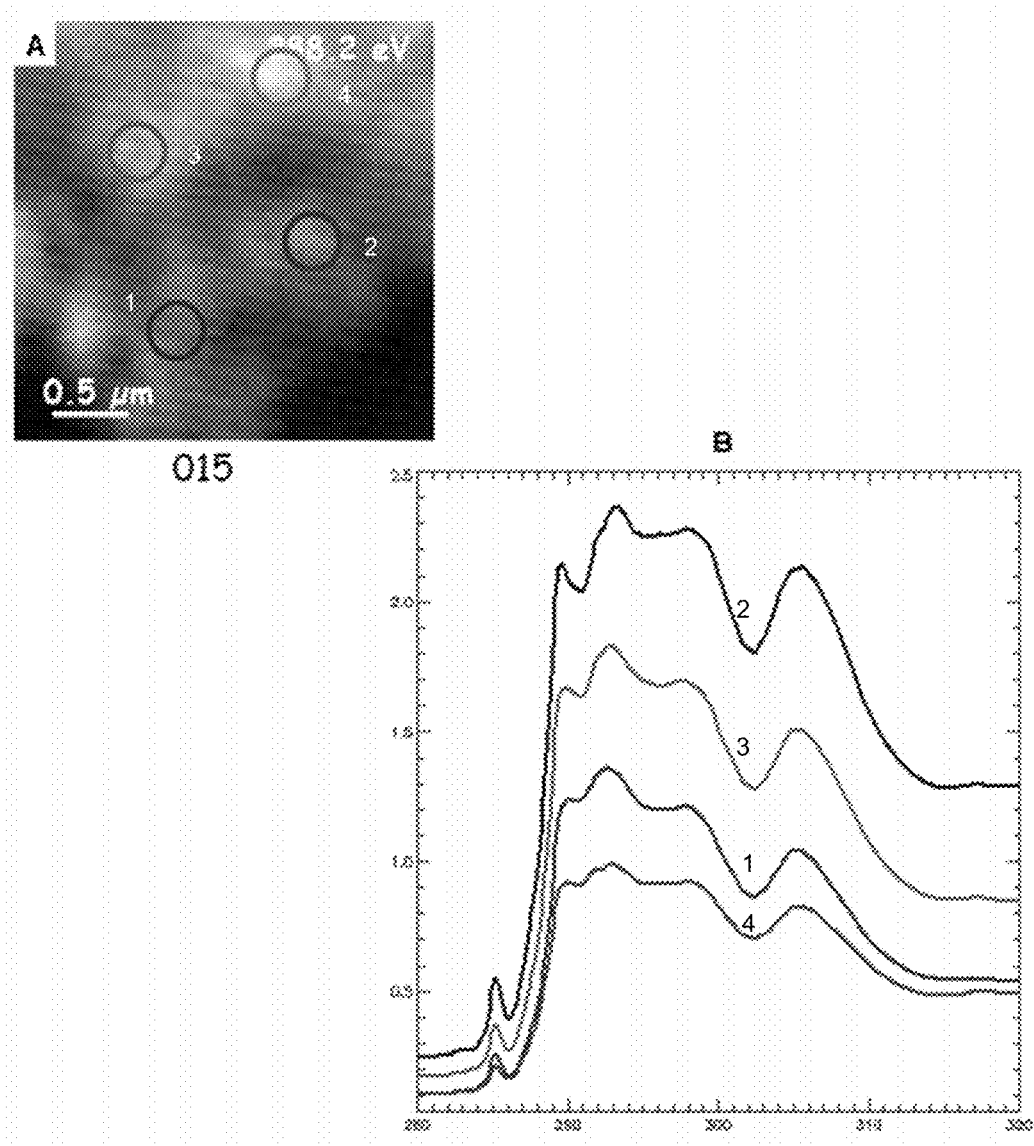

FIG. 19 shows X-ray absorption C 1s-edge spectra of nanodiamonds in exemplary embodiments of the present application. (A) Scanning transmission X-Ray microscopic image of nanodiamonds; (B) X-ray C 1s-edge spectra of the marked areas recorded by scanning transmission X-Ray microscope. The spectra obtained from four different regions of nanodiamonds showed same spectral pattern.

Figure 20:
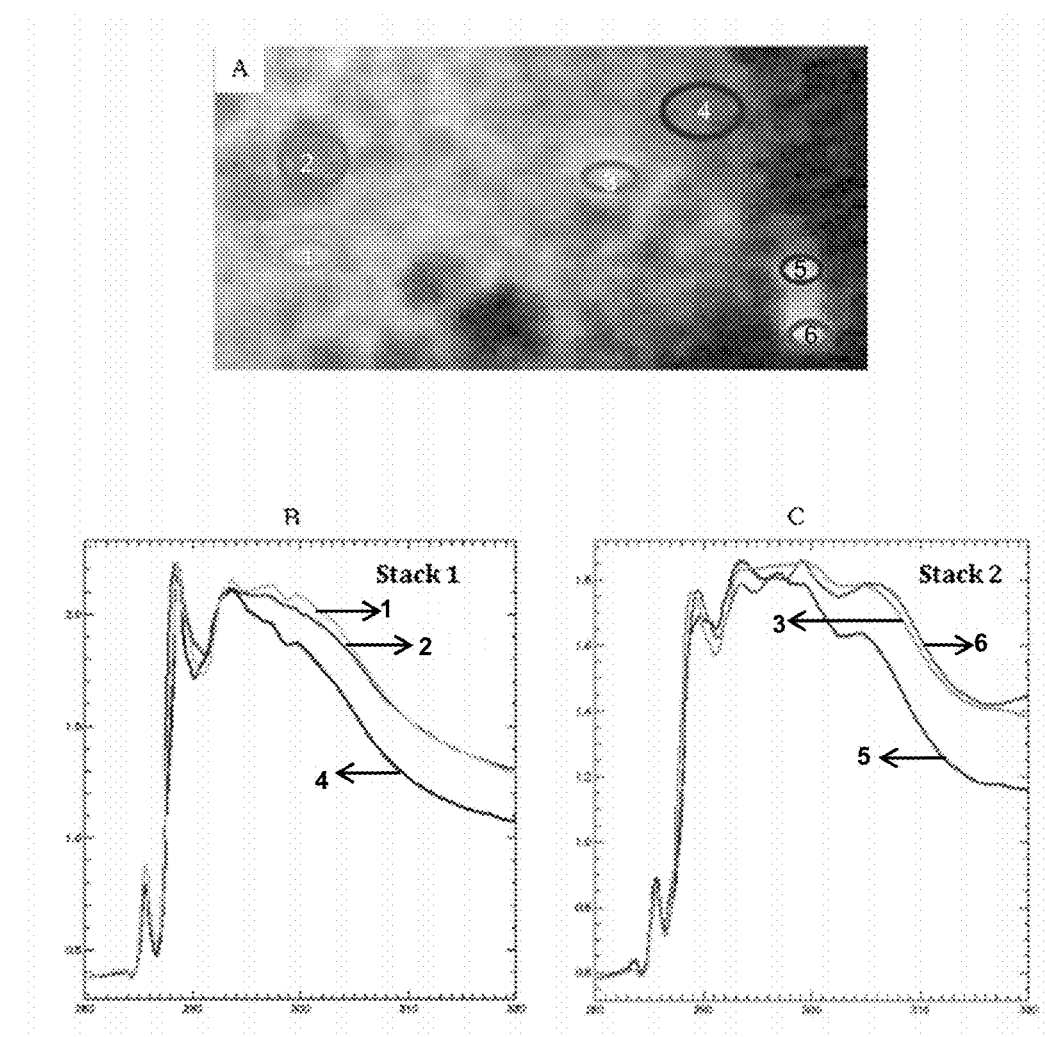

FIG. 20 shows X-ray absorption C 1s-edge spectra of a nanodiamond treated cell in exemplary embodiments of the present application. (A) Scanning transmission X-Ray microscopic image of a single A375 cell incubated with nanodiamonds; (B) and (C) C 1s-edge spectra of the marked areas recorded by scanning transmission X-ray microscope revealing association of nanodiamonds with cell.

Figure 21:
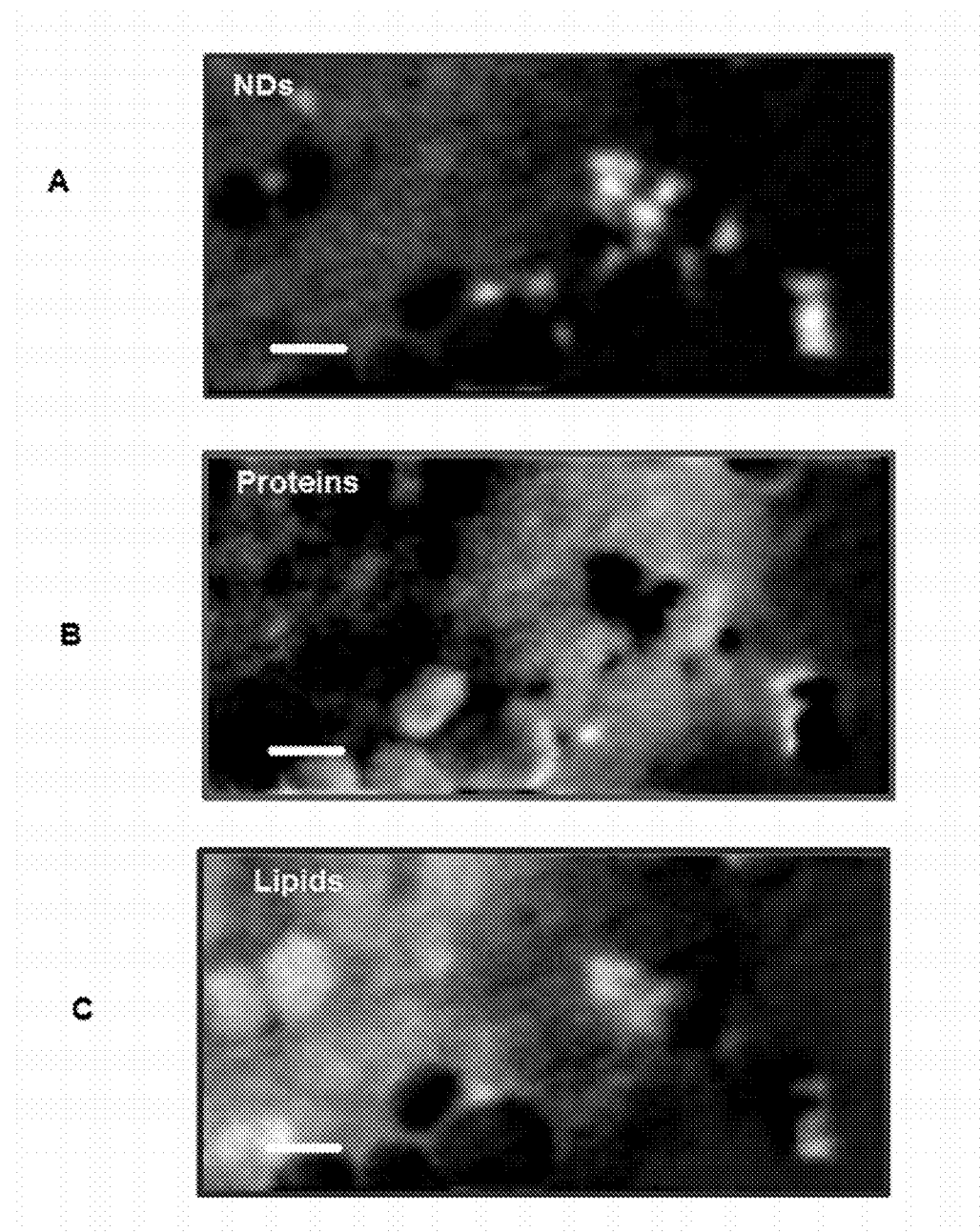

FIG. 21 shows a grey scale scanning transmission X-Ray microscopic map of a single A375 cell treated with nanodiamonds in exemplary embodiments of the present application. The brighter region indicates the distribution of (A) nanodiamonds; (B) proteins; (C) lipids.

Figure 22:
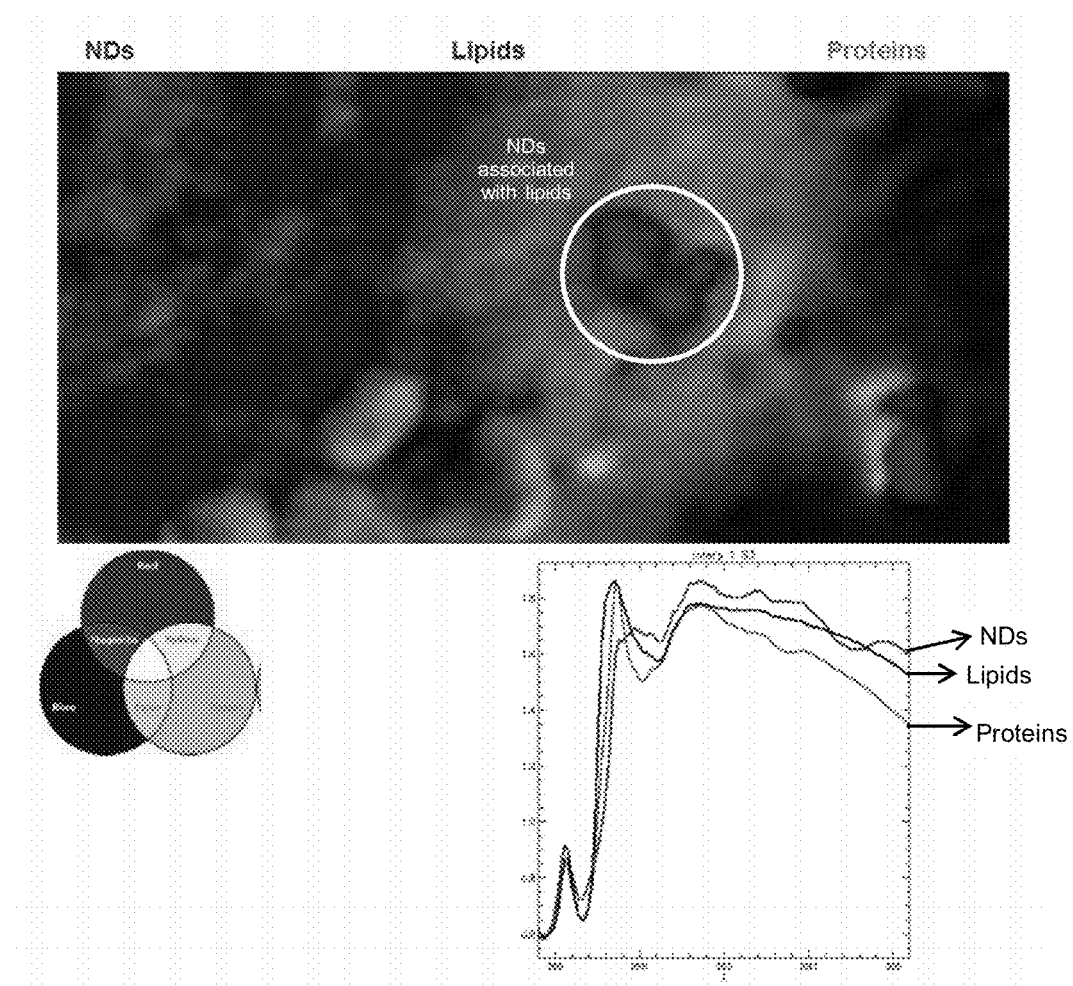
Figure 23:
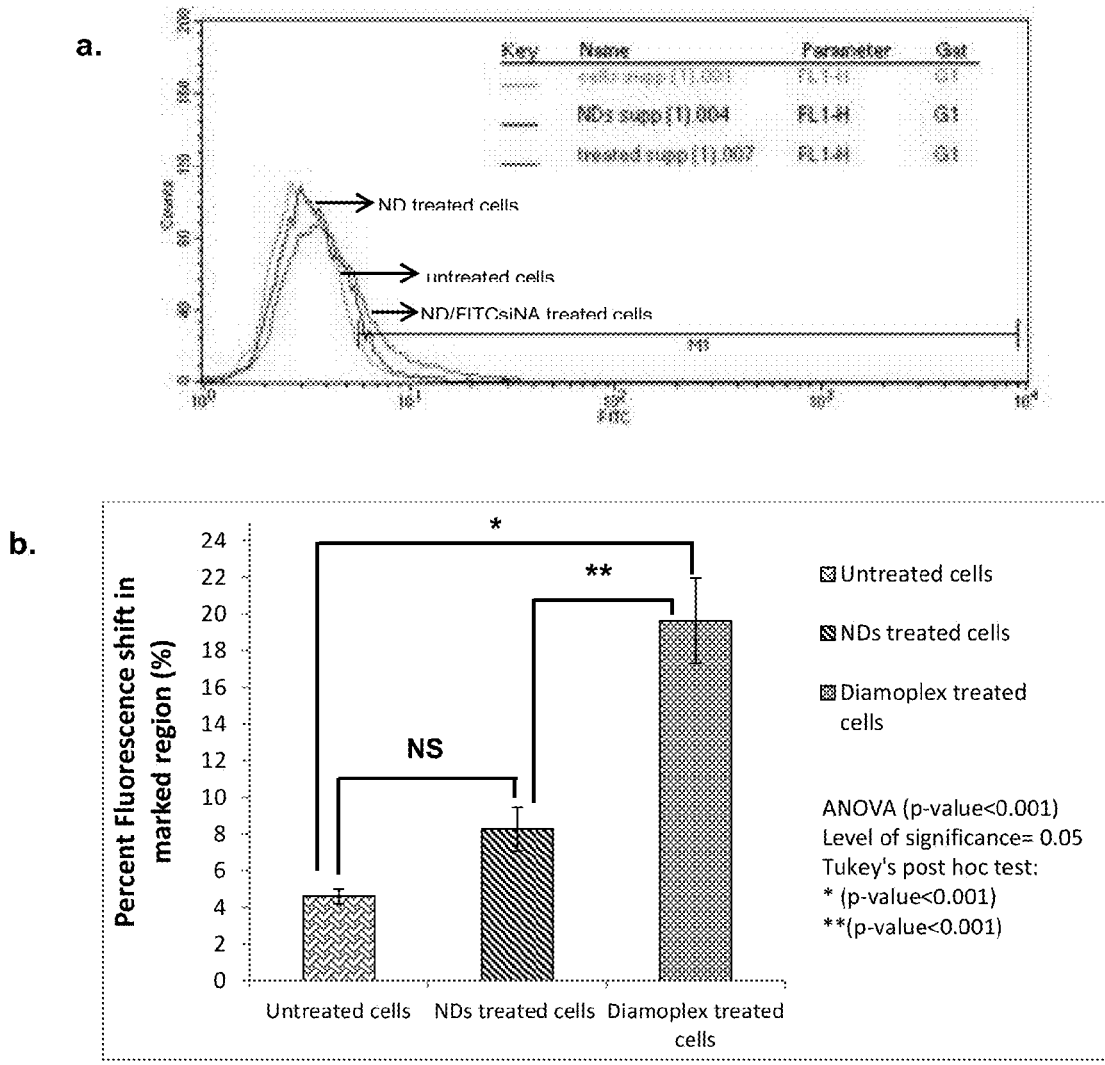

FIG. 22 shows a color coded scanning transmission X-ray microscopic composite map of a single A375 cell treated with nanodiamonds in exemplary embodiments of the present application. (Upper) Color coded scanning transmission X-Ray microscopic composite map of nanodiamond treated A375 cell revealing lysine-functionalized nanodiamonds, proteins and lipids; (Bottom) C 1s-edge X-ray absorption spectra as recorded by scanning transmission X-ray microscope. Individual peaks for lipids, proteins and NDs in X-ray absorption spectra are indicated FIG. 23 shows flow cytometric spectra for fluorescence shift of HeLa cells treated with nanodiamonds in exemplary embodiments of the present application. (a) Overlay of fluorescence spectra of untreated cells, lysine-ND treated cells and lysine ND-SiRNA complex treated cells; (b) Comparison of percent fluorescence shift for lysine ND treated HeLa cells.

DETAILED DESCRIPTION

I. Definitions

Unless otherwise indicated, the definitions and embodiments described in this and other sections are intended to be applicable to all embodiments and aspects of the application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

The term "suitable" as used herein means that the selection of the particular molecule, material and/or conditions would depend on the specific synthetic manipulation to be performed, and the identity of the molecule(s) and/or material(s) to be transformed, but the selection would be well within the skill of a person trained in the art. All synthetic process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a nucleic acid" should be understood to present certain aspects with one nucleic acid, or two or more additional nucleic acids.

In embodiments comprising an "additional" or "second" component, such as an additional or second nucleic acid, the second component as used herein is chemically different from the other components or first component. A "third" component is different from the other, first, and second components, and further enumerated or "additional" components are similarly different.

The term "alkyl" as used herein, whether it is used alone or as part of another group, means straight or branched chain, saturated alkyl groups. The number of carbon atoms that are possible in the referenced alkyl group is indicated by the numerical prefix "$C_{n1-n2}$". For example, the term $C_{1-6}$alkyl means an alkyl group having 1, 2, 3, 4, 5, or 6 carbon atoms.

The term "alkylene" as used herein means straight or branched chain, saturated alkylene group, that is, a saturated carbon chain that contains substituents on two of its ends. The number of carbon atoms that are possible in the referenced alkylene group is indicated by the numerical prefix "$C_{n1-n2}$". For example, the term $C_{1-6}$alkylene means an alkylene group having 1, 2, 3, 4, 5 or 6 carbon atoms.

The term "aryl", whether it is used alone or as part of another group, means a ring or ring system comprising at least one aromatic carbocycle and includes phenyl, naphthyl, indanyl and the like.

In embodiments of the present application, the amino acids described herein have at least one asymmetric center. These amino acids exist as enantiomers. Where amino acids possess more than one asymmetric center, they may exist as diastereomers. It is to be understood that all such isomers and mixtures thereof in any proportion are encompassed within the scope of the present application. It is to be further understood that while the stereochemistry of the amino acid may be as shown in any given amino acid listed herein, such amino acids may also contain certain amounts (e.g. less than 20%, suitably less than 10%, more suitably less than 5%) of amino acids having alternate stereochemistry. For example, amino acids that are shown without any stereochemical designations are understood to be racemic mixtures (i.e. contain an equal amount of each possible enantiomer or diastereomer). However, it is to be understood that all enantiomers and diastereomers are included within the scope of the present application, including mixtures thereof in any proportion.

The term "naturally occurring amino acid" as used herein refers to an organic compound comprising amine (—$NH_2$) and carboxylic acid (—COOH) functional groups, along with a side-chain specific to each amino acid. The key elements of an amino acid are carbon, hydrogen, oxygen and nitrogen, though other elements are found in the side-chains of certain amino acids, including S and Se. About 500 amino acids are known in nature[33]. They can be classified, for example, according to the core structural functional groups' locations as alpha (α), beta (β3), gamma (γ) or delta (δ), amino acids; other categories relate to polarity, pH level, and side-chain group type (e.g. acidic, basic, neutral, aliphatic, acyclic, aromatic, containing hydroxyl or sulfur, etc.). In an embodiment, the naturally occurring amino acid is one of the 23 proteinogenic amino acids, that is amino acids that are precursors to proteins, and are incorporated into proteins during translation.

The term "naturally occurring basic amino acid" as used herein refers to a naturally occurring amino acid, having a side chain comprising a basic group (i.e. can accept hydrogen ions). It will be appreciated by a person skilled in the art that whether a basic group exists in a protonated or deprotonated form depends, for example on the $pK_a$ of the basic group. In an embodiment, at least one basic group of the basic amino acid has been converted to its corresponding acid addition salt. In another embodiment, the acid addition salt is a pharmaceutically acceptable salt.

The term "amino acid derivative" as used herein refers to a naturally occurring amino acid, or an analog thereof, containing a modified functional group, such as a naturally occurring amino acid, or analog thereof, in which the amino group, the carboxyl group and/or a side chain function group has been derivatized. Examples of such groups include, but are not limited to, $C_{1-10}$alkyl-, aryl- and $C_{1-6}$alkylenearyl-functionalized amines, carboxylic acids, hydroxyls, thiols and/or amides, including di-functionalization of a group where possible (for example amines and amides). In a further embodiment, such groups include methyl-, ethyl, aryl- and benzyl-functionalized carboxylic acids, hydroxyls and/or thiols and/or methyl-, dimethyl-, ethyl-, diethyl, aryl-, diaryl, benzyl and dibenzyl-functionalized amines and/or amides. Amino acid derivatives are either naturally occurring or are synthetic.

The term "amino acid analog" as used herein refers to a naturally occurring amino acid, or a derivative thereof, in which one or more of the functional groups have been modified, for example oxidized, reduced, functionalized or removed, replaced with a functionally similar functional group, or moved to a different location on the amino acid molecule. Examples of such compounds are well known and studied in the art, and include, for example, β-amino acids, fluorinated amino acids and α-hydroxy analogs. Amino acid analogs are either naturally occurring or are synthetic.

The term "nanodiamond" or "ND" as used herein refers to a diamond particle having an average particle size of less than about 1 μm. "Average particle size" refers to the number average particle size based on the largest linear dimension of the particle (usually referred to as diameter). In an embodiment, the nanodiamonds have an average particle size of about 1 nm to 250 nm or less. In a further embodiment, the nanodiamonds have an average particle size of about 1 nm to about 10 nm.

The term "covalently linked" as used herein means that the referenced group is attached to the nanodiamond surface via at least one covalent linkage. In an embodiment, the covalent linkage is an ester or amide linkage, such as:

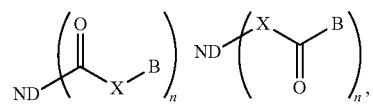

wherein ND represents the nanodiamond, X is O or NH, B represents the at least one naturally occurring basic amino acid, or an analog or derivative of a naturally occurring basic amino acid, or an acid addition salt thereof, and n is an integer representing the number of such groups on the nanodiamond. The selection of a suitable synthetic route to obtain an ester or amide linkage can be made by a person skilled in the art. A number of synthetic routes are known in the art, for example as described in Smith, M. B. and March J., "March's Advanced Organic Chemistry: Reactions, Mechanisms and Structure" 5th ed., John Wiley & Sons, Inc., 2001 (New York) at, for example, pages 482-486 and pages 506-510. In another embodiment, the at least one naturally occurring basic amino acid, or an analog or derivative of a naturally occurring basic amino acid, or an acid addition salt thereof, is covalently bonded to the nanodiamond via a linker group. In an embodiment, the linker group comprises at least one ester or amide linkage although a person skilled in the art would appreciate that other linker groups, such as ethers, thioethers, thioamides, thioesters and/or amines can additionally, or alternatively, be present. In a further embodiment, the linker group also comprises one or more $C_1$-$C_{20}$alkylene groups, such groups being either straight chain or branched chain alkylene groups. In another embodiment, when more than one amino acid is present, each amino acid is attached to the ND via its own linker or two or more of the amino acids are attached to the ND via the same linker. In an embodiment, the nanodiamonds are functionalized with at least one naturally occurring basic amino acid, or an analog or derivative of a naturally occurring basic amino acid, or an acid addition salt thereof, in a monolayer or multilayer arrangement.

The term "nucleic acid" as used herein includes all forms of oligonucleotides, deoxyribonucleic acid (DNA) and ribonucleic acid (RNA). Nucleic acids are either isolated from natural sources or prepared using well-known synthetic techniques. All forms of DNA and RNA, both single and double stranded, are included in the present application, for example, genomic DNA, complementary DNA (cDNA), plasmid DNA (pDNA), messenger RNA (mRNA), transfer RNA (tRNA), transfer-messenger RNA (tmRNA), ribosomal RNA (rRNA), small interfering RNA (sRNA), microRNA (miRNA), piwi-interacting RNA (piRNA), antisense RNA (aRNA), RNA interference (RNAi), small nuclear RNA (snRNA) and small nucleolar RNA (snoRNA), and portions thereof. Nucleic acids also include artificial analogs of natural nucleic acids that have been designed and synthesized for example, to improve stability, and include, for example, peptide nucleic acids, morpholino nucleic acids, locked nucleic acids, glycose nucleic acids and threose nucleic acids. Each of these later nucleic acid analogs is distinguished from naturally occurring DNA or RNA by changes to the backbone of the molecule. In an embodiment, the nucleic acid is any sequence of nucleotides that is used for diagnostic, therapeutic and/or cell monitoring applications.

The term "pristine nanodiamonds" or "pNDs" as used herein refers to carboxylated nanodiamonds in their original form as received from the manufacturer.

The term "reoxidized nanodiamonds" or "rNDs" as used herein refers to acid-treated nanodiamonds where most of surface functionalities are converted into carboxylate groups.

The term "fND" and the like as used herein refers to a functionalized nanodiamond comprising at least one hydrochloride acid addition salt of a lysine-based compound (2,6-diamino-N-(3-aminopropyl)hexanamide) covalently bonded via an amide linkage to a nanodiamond. The following schematic represents a hydrochloride acid addition salt of a 2,6-diamino-N-(3-aminopropyl)hexanamide covalently attached via an amide linkage to a nanodiamond in the configuration used in the studies described herein:

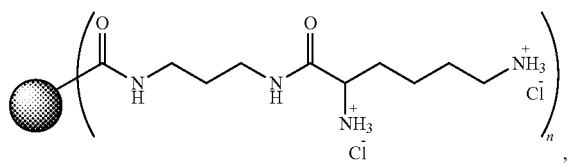

wherein n is an integer representing the number of 2,6-diamino-N-(3-aminopropyl)hexanamide groups on the nanodiamond. A person skilled in the art will appreciate that other possible configurations have one of the other two amino groups attached to the nanodiamond. In an embodiment, the lysine-based compound is attached to a nanodiamond as a mixture of all three possible configurations. In a further embodiment, the configurations where a primary amino group (i.e. the amino groups located at each end of the molecule) is attached to the nanodiamond represents the major species. A person skilled in the art would also appreciate that a plurality of 2,6-diamino-N-(3-aminopropyl)hexanamide, hydrochloride acid addition salts, will be covalently attached to the ND surface, i.e. that n will be a number representing the loading of the basic amino acid-linker groups on the nanodiamond. This number will depend on number of carboxylic acid groups available for reaction on the precursor carboxylated ND as well as the coupling conditions as would be understood by a person skilled in the art.

The term "ND-COOH" as used herein refers to a carboxylated nanodiamond. The following schematic represents a carboxylic acid group on the surface of a nanodiamond:

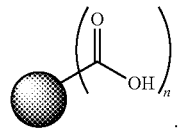

A person skilled in the art will appreciate that a plurality of groups will be covalently attached to the ND surface i.e. that n is an integer representing the number of groups on the nanodiamond. This number will depend on the conditions for the oxidation of the detonation nanodiamonds and the size of the nanodiamond as would be understood by a person skilled in the art. Further, it is possible for more than one type of group, including more than one type of amino acid, to be covalently attached to the ND surface in addition to the naturally occurring basic amino acid. In addition to the naturally occurring basic amino acid, it is possible for any type of naturally occurring amino acid, including acidic, and neutral, and analogs and derivatives thereof, to be covalently attached to the ND surface.

The term "nanodiamond-based" composition as used herein means that the composition comprises a nanodiamond.

The term "reversibly bound" as used herein refers to a non-covalent interaction, for example, between the functionalized ND and the nucleic acid molecules. Such interaction is one that is strong enough to allow transport of at least a portion of the intact complexes across a cell membrane, and that will allow release of at least a portion of the nucleic acid molecules once the complex is at its desired location, such as inside a cell. In an embodiment, the functionalized ND and nucleic acid are bound by electrostatic interactions.

The term "electrostatic interaction" refers to non-covalent attractive forces between molecules of opposite charge.

The term "subject" as used herein includes all members of the animal kingdom including mammals, and suitably refers to humans.

The term "pharmaceutically acceptable" means compatible with the treatment of subjects, in particular humans.

The term "pharmaceutically acceptable salt" means an acid addition salt suitable for, or compatible with, the treatment of subjects.

An acid addition salt suitable for, or compatible with, the treatment of subjects is any non-toxic organic or inorganic salt of any basic compound. Basic compounds that form an acid addition salt include, for example, compounds comprising an amino group. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to one skilled in the art.

The formation of a desired compound salt is achieved using standard techniques. For example, the neutral compound is treated with an acid or base in a suitable solvent and the formed salt is isolated by filtration, extraction or any other suitable method.

The terms "protecting group" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3$^{rd}$ Edition, 1999 and in Kocienski, P. Protecting Groups, 3rd Edition, 2003, Georg Thieme Verlag (The Americas). Examples of suitable protecting groups include, but are not limited to t-Boc, Ac, Ts, Ms, silyl ethers such as TMS, TBDMS, TBDPS, Tf, Ns, Bn, Fmoc, benzoyl, dimethoxytrityl, methoxyethoxymethyl ether, methoxymethyl ether, pivaloyl, p-methyoxybenzyl ether, tetrahydropyranyl, trityl, ethoxyethyl ethers, carbobenzyloxy, benzoyl and the like.

t-Boc as used herein refers to the group t-butyloxycarbonyl.

Ac as used herein refers to the group acetyl.

Ts (tosyl) as used herein refers to the group p-toluenesulfonyl.

Ms as used herein refers to the group methanesulfonyl.

TMS as used herein refers to the group trimethylsilyl.

TBDMS as used herein refers to the group t-butyldimethylsilyl.

TBDPS as used herein refers to the group t-butyldiphenylsilyl.

Tf as used herein refers to the group trifluoromethanesulfonyl.

Ns as used herein refers to the group naphthalene sulphonyl.

Bn as used herein refers to the group benzyl.

Fmoc as used herein refers to the group fluorenylmethoxycarbonyl.

Cbz as used herein refers to the group carboxybenzyl.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with early Alzheimer's disease can be treated to prevent progression, or alternatively a subject in remission can be treated with a compound or composition described herein to prevent recurrence. Treatment methods comprise administering to a subject a therapeutically effective amount of one or more of the complexes of the present application and optionally consist of a single administration, or alternatively comprises a series of administrations. For example, the complexes of the present application may be administered at least once a week. However, in another embodiment, the complexes may be administered to the subject from about one time per three weeks, or about one time per week to about once daily for a given treatment. In another embodiment, the complexes are administered 2, 3, 4, 5 or 6 times daily. The length of the treatment period depends on a variety of factors, such as the severity of the disease, the age of the patient, the concentration, the activity of the complexes of the present application, and/or a combination thereof. It will also be appreciated that the effective dosage of the complex used for the treatment or prophylaxis may increase or decrease over the course of a particular treatment or prophylaxis regime. Changes in dosage may result and become apparent by standard diagnostic assays known in the art. In some instances, chronic administration may be required. For example, the complexes of the present application are administered to the subject in an amount and for duration sufficient to treat the patient.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with a disease, disorder or condition or manifesting a symptom associated with a disease, disorder or condition or a reduction in the risk or probability of.

As used herein, the term "effective amount" or "therapeutically effective amount" means an amount effective, at dosages and for periods of time necessary to achieve the desired result. For example in the context of treating a disease, disorder or condition, an effective amount is an amount that, for example, reduces symptoms or severity of the disease, disorder or condition compared to without administration of the complex. Effective amounts may vary according to factors such as the disease state, age, sex and/or weight of the subject. The amount of a given complex that will correspond to such an amount will vary depending upon various factors, such as the given complex, the pharmaceutical formulation, the route of administration, the type of condition, disease or disorder, the identity of the subject being treated, and the like, but can nevertheless be routinely determined by one skilled in the art.

The term "administered" as used herein means administration of a therapeutically effective dose of a complex of the application to a cell either in cell culture or in a subject.

The term "gene therapy" as used herein refers to the use of DNA as a pharmaceutical agent to treat disease. In embodiments of the application, gene therapy includes administration or use of DNA that encodes a functional, therapeutic gene to replace a mutated gene, or administration or use of DNA that corrects a mutation or administration or use of DNA that encodes a therapeutic protein drug (rather than a natural human gene) to provide treatment. In gene therapy, DNA that encodes a therapeutic protein is comprised in the nanodiamond complexes of the present application, which are used to transport the DNA inside cells within the body. Once inside, the DNA becomes expressed by the cell machinery, resulting in the production of therapeutic protein, which in turn treats the subject's disease.

Some diseases that have shown some success with gene therapy are the retinal disease Leber's congenital amaurosis, X-linked severe combined immunodeficiency (SCID), ADA-SCID, adrenoleukodystrophy, cancers such as chronic lymphocytic leukemia (CLL), acute lymphocytic leukemia (ALL), multiple myeloma, cystic fibrosis and Parkinson's disease.

The term "antisense therapy" as used herein refers to a form of treatment for genetic disorders or infections. When the genetic sequence of a particular gene is known to be causative of a particular disease, it is possible to synthesize a strand of nucleic acid (DNA, RNA or a chemical analogue) that will bind to the messenger RNA (mRNA) produced by that gene and inactivate it, effectively turning that gene "off". This is because mRNA has to be single stranded for it to be translated. Alternatively, the strand of nucleic acid might be targeted to bind a splicing site on pre-mRNA and modify the exon content of an mRNA. This synthesized nucleic acid is termed an "anti-sense" oligonucleotide because its base sequence is complementary to the gene's messenger RNA (mRNA), which is called the "sense" sequence (so that a sense segment of mRNA "5'-AAGGUC-3'" would be blocked by the anti-sense mRNA segment "3'-UUCCAG-5'").

Antisense drugs have been studied in the treatment of a variety of diseases such as cancers (including lung cancer, colorectal carcinoma, pancreatic carcinoma, malignant glioma and malignant melanoma), diabetes, Amyotrophic lateral sclerosis (ALS), Duchenne muscular dystrophy and diseases such as asthma, arthritis and pouchitis with an inflammatory component. Two antisense drugs have been approved by the U.S. Food and Drug Administration (FDA), fomivirsen (marketed as Vitravene) as a treatment for cytomegalovirus retinitis and mipomersen (marketed as Kynamro) for homozygous familial hypercholesterolemia.

The term "RNA interference" (RNAi) as used herein which is also called post transcriptional gene silencing (PTGS), refers to a biological process in which RNA molecules inhibit gene expression, typically by causing the destruction of specific mRNA molecules. Historically, it was known by other names, including co-suppression, post transcriptional gene silencing (PTGS), and quelling. Two types of small ribonucleic acid (RNA) molecules—microRNA (miRNA) and small interfering RNA (siRNA)—are central to RNA interference. RNAs are the direct products of genes, and these small RNAs can bind to other specific messenger RNA (mRNA) molecules and either increase or decrease their activity, for example by preventing an mRNA from producing a protein. RNA interference has an important role in defending cells against parasitic nucleotide sequences—viruses and transposons—but also in directing development as well as gene expression in general. The RNAi pathway is found in many eukaryotes including animals and is initiated by the enzyme Dicer, which cleaves long double-stranded RNA (dsRNA) molecules into short double stranded fragments of ~20 nucleotides that are called siRNAs. Each siRNA is unwound into two single-stranded (ss) ssRNAs, namely the passenger strand and the guide strand. The passenger strand is degraded, and the guide strand is incorporated into the RNA-induced silencing complex (RISC). The most studied outcome is post-transcriptional gene silencing, which occurs when the guide strand base pairs with a complementary sequence in a messenger RNA molecule and induces cleavage by Argonaute, the catalytic component of the RISC complex. In some organisms, this process is known to spread systemically, despite the initially limited molar concentrations of siRNA.

RNAi has become a useful research tool, both in cell culture and in living organisms, because synthetic dsRNA introduced into cells can selectively and robustly induce suppression of specific genes of interest. RNAi may be used for large-scale screens that systematically shut down each gene in the cell, which can help to identify the components necessary for a particular cellular process or an event such as cell division. The pathway is also used as a practical tool in biotechnology and medicine.

II. Functionalized Nanodiamonds and their Compositions

A procedure for covalently bonding naturally occurring basic amino acids to detonated nanodiamonds (NDs) to obtain basic amino acid-functionalized nanodiamonds has been developed. NDs were oxidized and functionalized by binding basic amino acid moieties (e.g. lysine and lysine plus histidine) attached to a three-carbon-length linker (1,3-diaminopropane) to their surfaces through amide bonds. Raman and Fourier transform infrared spectroscopy, zeta potential measurement, dynamic light scattering, atomic force microscopic imaging, and thermogravimetric analysis were used to characterize the basic amino acid-functionalized NDs. The ability of basic amino acid-functionalized NDs to bind plasmid DNA and small interfering RNA was investigated by gel electrophoresis assay and through size and zeta potential measurements. NDs were successfully functionalized via a three-carbon-length-linker, producing a surface loading of 1.7 mmol $g^{-1}$ of ND. The basic amino acid-functionalized NDs formed highly stable aqueous dispersions with a zeta potential of +49 mV and a particle size of approximately 21 nm, as measured by DLS. AFM images confirmed the disaggregation of the basic amino acid functionalized NDs in comparison with carboxylated NDs. The hydrophilicity exhibited by the functionalized NDs in this study provides an advantage for their use in animal and human systems, as water can be used as a dispersion medium. The basic amino acid-functionalized NDs were found to bind, through electrostatic interactions, plasmid DNA (specifically, pGTCMV.IFN-GFP) and small interfering RNA (specifically, anti-GFP siRNA and FITC conjugated control siRNA), forming nanosized "diamoplexes". The basic amino acid-functionalized NDs show potential for use as delivery agents for nucleic acids. The basic amino acid-functionalized NDs were observed to interact with cells, and laser scanning confocal microscopic measurements showed internalization of basic amino acid-functionalized NDs. The basic amino acid-functionalized NDs also showed negligible cytotoxicity, remaining biocompatible from concentrations of 4 to 250 μg/mL in HeLa cells. A basic amino acid-functionalized NDs-siRNA complex was observed to deliver siRNA to the cytoplasm of a cell.

Accordingly, the present application includes a functionalized nanodiamond, comprising at least one naturally occurring basic amino acid, or an analog or derivative of a naturally occurring basic amino acid, or an acid addition salt thereof, covalently linked to a nanodiamond. In an embodiment, the at least one naturally occurring basic amino acid is selected from arginine, histidine and lysine, and analogs and derivatives thereof, or an acid addition salt thereof.

In an embodiment of the present application, the at least one naturally occurring basic amino acid is selected from one or more of histidine and lysine, or an acid addition salt thereof.

In an embodiment, the at least one naturally occurring basic amino acid, or analog or derivative thereof, is covalently linked to the nanodiamond via an ester linkage. For example, a suitable nanodiamond is reacted with a suitable basic amino acid under conditions to obtain an ester linkage. In an embodiment, the conditions to obtain the ester linkage comprise treating a carboxylated nanodiamond (ND-COOH) under conditions to activate the carboxylic acid, for example by conversion to the acid chloride (ND-COCl) or by reaction with a carboxylic acid activating reagent to provide a nanodiamond of the formula ND-CO-A, wherein A is an activating group for a carboxylic acid, followed by nucleophilic displacement of the chloride or A group with an oxygen nucleophile (such as a hydroxyl group) on the basic amino acid. Carboxylic acid activating reagents are well known in the art and include, for example, well known peptide coupling reagents such as dicyclohexylcarbodiimide (DCC), diisopropylcarbodiimide, hydroxybenzotriazole (HOBT), (Benzotriazol-1-yloxy)tris(dimethylamino)phosphonium hexafluorophosphate (BOP), [N,N,N',N'-tetramethyl-O-(7-azabenzotriazol-1-yl)uronium hexafluorophosphate (HATU) and the like. A person skilled in the art would appreciate that an ester linkage is also available using the same reaction conditions, but, in the alternative, reacting a detonated nanodiamond that has been treated under reductive conditions to provide a hydroxylated nanodiamond (ND-OH), with the basic amino acid comprising an activated carboxylic acid. It will also be appreciated by a person skilled in the art that one or more protecting groups can be used to protect certain other sites of the basic amino acid from reacting with the nanodiamond to form an ester linkage in an undesired location. The functionalized nanodiamond comprising the protected form of the basic amino acid can then subsequently be deprotected.

In an embodiment, the naturally occurring 'basic amino acid, or analog or derivative thereof, is covalently linked to the nanodiamond via an amide linkage. For example, a suitable nanodiamond is reacted with a suitable basic amino acid under conditions to obtain an amide linkage. In an embodiment, the conditions to obtain the amide linkage comprise treating a carboxylated nanodiamond (ND-COOH) under conditions to activate the carboxylic acid, for example by conversion to the acid chloride (ND-COCl) or by reaction with a carboxylic acid activating reagent to provide a nanodiamond of the formula ND-CO-A, wherein A is an activating group for a carboxylic acid, followed by nucleophilic displacement of the chloride or A group with a nitrogen nucleophile (such as an amino group) on the basic amino acid. Carboxylic acid activating reagents are well known in the art and include, for example, well known peptide coupling reagents such as dicyclohexylcarbodiimide (DCC), diisopropylcarbodiimide, hydroxybenzotriazole (HOBT), (Benzotriazol-1-yloxy)tris(dimethylamino)phosphonium hexafluorophosphate (BOP), [N,N,N',N'-tetramethyl-O-(7-azabenzotriazol-1-yl)uronium hexafluorophosphate (HATU) and the like. A person skilled in the art would appreciate that an amide linkage is also available using the same reaction conditions, but, in the alternative, reacting a detonated nanodiamond that has been treated under conditions to provide an amino-substituted nanodiamond (ND-NH$_2$), with a basic amino acid comprising an activated carboxylic acid. It will also be appreciated by a person skilled in the art that one or more protecting groups can be used to protect certain other sites of the basic amino acid from reacting with the nanodiamond to form an amide linkage in an undesired location. The functionalized nanodiamond comprising the protected form of the basic amino acid can then subsequently be deprotected.

In an embodiment, the at least one naturally occurring basic amino acid, or analog or derivative thereof, is covalently linked to the nanodiamond via a linker group. In an embodiment, the linker group comprises one or more $C_1$-$C_{20}$alkylene groups, such groups being either straight chain or branched chain alkylene groups. In an embodiment, the at least one basic amino acid is covalently linked to the nanodiamond via a linker group comprising a $C_{1-6}$alkylene group. In another embodiment, the at least one basic amino acid is covalently linked to the nanodiamond via a linker group comprising a propylene group. In an embodiment, the linker group is linked to the at least one basic amino acid via at least one ester or amide linkage although a person skilled in the art would appreciate that other linker groups, such as ethers, thioethers, thioamides, thioesters and/or amines is additionally, or alternatively, present. It is an embodiment that the linker group is linked to the at least one basic amino acid via an amide linkage.

It is an embodiment that, when more than one type of naturally occurring basic amino acid is covalently linked to the ND, each naturally occurring basic amino acid is linked via a different linker or each naturally occurring basic amino acid is linked via the same linker.

In an embodiment, the at least one naturally occurring basic amino acid and the linker group together form the structure:

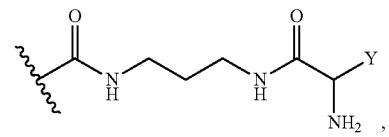

wherein Y is the side chain of the naturally occurring basic amino acid, or an acid addition salt thereof. In an embodiment, Y is selected from —(CH$_2$)$_4$NH$_2$,

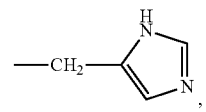

and —(CH$_2$)$_3$NHC(NH)NH$_2$.

In another embodiment, the at least one naturally occurring basic amino acid and the linker group together form the structure:

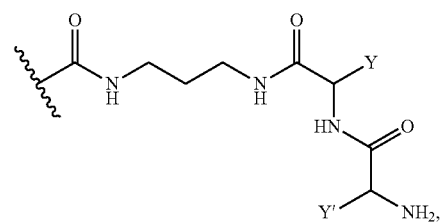

wherein Y and Y' are, independently, the side chain of the basic amino acid, or an acid addition salt thereof. In an embodiment, Y and Y' are independently selected from —(CH$_2$)$_4$NH$_2$,

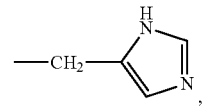

and —(CH$_2$)$_3$NHC(NH)NH$_2$.

In another embodiment, the naturally occurring basic amino acid and the linker group together form the structure:

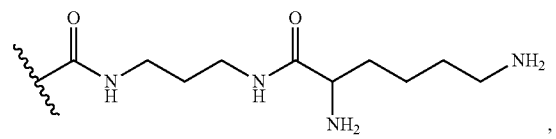 [SMILES: *C(=O)NCCCNC(=O)C(N)CCCCN]

or an acid addition salt thereof.

In another embodiment, the at least one naturally occurring basic amino acid and the linker group together form the structure:

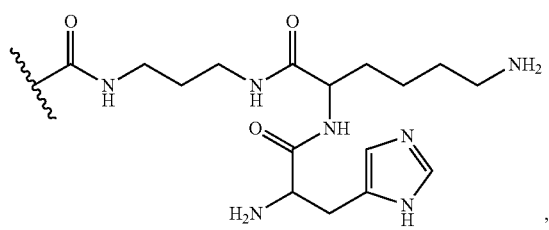 [SMILES: *C(=O)NCCCNC(=O)C(CCCCN)NC(=O)C(N)Cc1cnc[nH]1]

or an acid addition salt thereof.

In an embodiment of the present application the functionalized NDs comprising at least one naturally occurring basic amino acid, or an analog or derivative of a naturally occurring basic amino acid, or an acid addition salt thereof, covalently linked to the nanodiamond, further comprises one or more other types of amino acids covalently attached to the nanodiamond. In an embodiment, the other type of amino acid is a naturally occurring acidic or neutral amino acid, or an analog or derivative thereof, for example, aspartic acid, glutamatic acid, lysyl methyl ester, histidyl methyl ester. In an embodiment, the presence of naturally occurring neutral and/or acidic amino acids, and/or analogs or derivatives thereof, for example covalently attached to the nanodiamonds or present as an intermediate layer, modulate the binding of the functionalized nanodiamonds with nucleic acids, improving the intracellular delivery and release of the genetic material inside the cell, for example, in the vicinity of the nucleus.

In an embodiment, the naturally occurring basic amino acid-functionalized nanodiamonds are prepared from a detonation nanodiamond. In another embodiment, the naturally occurring basic amino acid-functionalized nanodiamonds are prepared from detonation nanodiamond that have been treated under oxidative or reductive conditions. In a further embodiment, the naturally occurring basic amino acid-functionalized nanodiamonds are prepared from detonation nanodiamonds that have been treated under oxidative conditions to provide a carboxylated nanodiamond (ND-COOH). In a further embodiment, the carboxylated nanodiamonds have a zeta potential of about −40 V to about −50 V, or about −45 V. In a further embodiment the basic amino acid-functionalized nanodiamonds are prepared from nanodiamonds having a diameter of about 1 nm to about 10 nm, about 3 nm to about 6 nm, or about 4 nm to about 5 nm.

In an embodiment, the functionalized nanodiamond has a surface loading of about 0.1 mmol/g nanodiamond to about 10 mmol/g nanodiamond. In another embodiment, the functionalized nanodiamond has a surface loading of about 1.7 mmol/g nanodiamond.

Acid addition salts of the naturally occurring basic amino acid-functionalized nanodiamonds are prepared, for example, by treating the neutral basic amino acid-functionalized nanodiamonds with the appropriate acid. In certain embodiments, deprotection of a protected basic amino acid-functionalized nanodiamond is performed under acidic conditions and the corresponding acid addition salt is obtained during this procedure.

In a further embodiment, the functionalized nanodiamonds of the present application further comprise targeting moieties, such as targeting peptides covalently attached to the surface. Identification of moieties that target chemical compounds, particles or entities to specific areas in a cell or subject are known in the art.

In an embodiment, the additional groups, including one or more naturally occurring neutral amino acids and naturally occurring acidic amino acids, and analogs and derivatives thereof, and targeting moieties, are covalently bonded to the nanodiamond in a sequential manner, prior to, or following, functionalization with the one or more naturally occurring basic amino acids, or analogs or derivatives thereof. In another embodiment, the additional groups, including one or more naturally occurring neutral amino acids and naturally occurring acidic amino acids, and analogs and derivatives thereof, and targeting moieties, are covalently bonded to the nanodiamond at the same time as functionalization with the one or more naturally occurring basic amino acids, or analogs or derivatives thereof.

The present application also includes a composition comprising a functionalized nanodiamond of the present application and a carrier. In an embodiment, the carrier is water.

In an embodiment, the composition comprising a functionalized nanodiamond of the present application is prepared by ultrasonicating functionalized nanodiamonds in a carrier such as water, for example reverse osmosis-purified water at a desired concentration, for example a concentration of about 2 mg/mL at a frequency of about 25 kHz for a time of about 4 hours, optionally followed by centrifugation at about 5200 g for about 6 minutes.

In another embodiment, the composition comprising a functionalized nanodiamond of the present application has a zeta potential of greater than about +30 mV. In a further embodiment, the aqueous composition has a zeta potential of about +49 mV.

In another embodiment, the composition has an average particle size of less than about 50 nm, about 5 nm to about 50 nm or about 21 nm.

The present application also includes a complex comprising a functionalized nanodiamond of the present application reversibly bound to a nucleic acid.

In an embodiment, the nucleic acid is DNA or RNA. In another embodiment, the nucleic acid is pDNA or siRNA. In a further embodiment, the nucleic acid is from the genome of an organism. It is an embodiment that the nucleic acid is a gene or a portion of a gene. In an embodiment, the organism is human. In another embodiment, the organism is a virus or bacteria and the nucleic acid is immunogenic. In a further embodiment, the nucleic acid has a therapeutic effect when administered to a subject.

In an embodiment, the ratio by weight of the functionalized nanodiamond to the nucleic acid is from about 20:1 to about 50:1 or about 40:1 to about 50:1.

The present application also includes a composition comprising one or more complexes of the present application and a carrier. In an embodiment, the composition comprises a complex of the present application and a carrier. In another embodiment, the carrier is water.

In another embodiment, the composition has an average particle size of from about 100 to about 300 nm.

In an embodiment, the composition has a zeta potential of at least about +20 mV. In another embodiment, the composition as a zeta potential of from about +30 mV to about +50 mV.

In another embodiment, the composition further comprises a serum. In an embodiment, the serum is fetal bovine serum.

The complexes of the present application are suitably formulated into pharmaceutical compositions and/or vaccine compositions for administration to subjects in a biologically compatible form suitable for administration in vivo. Accordingly, the present application further includes a pharmaceutical composition comprising one or more complexes of the present application and a pharmaceutically acceptable carrier. The present application also includes a vaccine composition comprising one or more complexes of the present application and a carrier suitable for administration in a vaccine. It will be appreciated by a person skilled in the art that a salt of a basic amino acid in a pharmaceutical composition will be a pharmaceutically acceptable salt, and a salt of a basic amino acid in a vaccine composition will be a salt suitable for administration in a vaccine.

The complexes of the present application are administered to a subject in a variety of forms depending on the selected route of administration, as will be understood by those skilled in the art. A complex of the present application is, for example, administered, for example, by oral, parenteral, buccal, sublingual, nasal, rectal, patch, pump or transdermal administration and the pharmaceutical compositions formulated accordingly.

Parenteral administration includes intravenous, intraperitoneal, subcutaneous, intramuscular, transepithelial, nasal, intrapulmonary, intrathecal, rectal and topical modes of administration. In an embodiment, parenteral administration is by continuous infusion over a selected period of time. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

It is also possible to freeze-dry the complexes of the present application and use the lyophilizates obtained, for example, for the preparation of products for injection.

The pharmaceutical forms suitable for injectable use include sterile aqueous solutions or dispersions and sterile powders for the extemporaneous preparation of sterile injectable solutions or dispersions. In all cases, the form is sterile and fluid to the extent that easy syringability exists.

Complexes of the present application may be used alone or in combination with other known agents useful for treating diseases, disorders or conditions. When used in combination with other agents useful in treating diseases, disorders or conditions, it is an embodiment that the complexes of the present application are administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion.

The dosage of the complexes of the present application can vary depending on many factors such as the pharmacodynamic properties of the complex, the mode of administration, the age, health and weight of the recipient, the nature and extent of the symptoms, the frequency of the treatment and the type of concurrent treatment, if any, and the clearance rate of the complex in the subject to be treated. One of skill in the art can determine the appropriate dosage based on the above factors. Complexes of the present application are administered initially in a suitable dosage that is optionally adjusted as required, depending on the clinical response. In an embodiment, complexes of the present application are administered in a single daily dose or the total daily dose is divided into two, three or four daily doses.

III. Methods and Uses

The basic amino-acid functionalized NDs of the present application are novel and therefore the present application includes all uses of these NDs, including therapeutic uses, diagnostic uses and research uses.

The functionalized NDs of the present application show potential for use as delivery agents for nucleic acids such as plasmids and siRNA. The complexes of the present application have been shown to be capable of delivering a nucleic acid such as siRNA to a cell.

Accordingly, the present application includes a method for delivering a nucleic acid to a cell, comprising administering a complex of the present application or a composition comprising such a complex to the cell.

The present application also includes a use of a complex of the present application or a composition comprising such a complex for delivering a nucleic acid to a cell.

Complexes capable of delivering a nucleic acid to a cell can be useful for treating diseases, disorders or conditions such as those having a genetic basis. Therefore the complexes of the present application can be useful as medicaments. Accordingly, the present application includes a complex of the present application for use as a medicament.

The present application also includes a method for treating a disease, disorder or condition comprising administering a complex of the present application, a pharmaceutical composition comprising such a complex or a vaccine composition comprising such a complex to a subject in need thereof. The present application further includes a use of a complex of the present application, a pharmaceutical composition comprising such a complex or a vaccine composition comprising such a complex for treating a disease, disorder or condition as well as a use of a complex of the present application, a pharmaceutical composition comprising such a complex or a vaccine composition comprising such a complex for the preparation of a medicament for treating a disease, disorder or condition. The present application also includes a complex of the present application, a pharmaceutical composition comprising such a complex or a vaccine composition comprising such a complex for use in treating a disease, disorder or condition.

In an embodiment, the disease, disorder or condition is a disease, disorder or condition having a genetic basis.

In an embodiment, the disease, disorder or condition having a genetic basis is a disease, disorder or condition which is treatable using gene therapy, antisense therapy or RNA interference. In another embodiment, the disease, disorder or condition having a genetic basis is a disease, disorder or condition which is preventable or treatable by the delivery of a genetic vaccine to a cell.

In embodiments of the present application, the disease, disorder or condition includes cardiovascular diseases, hepatitis B, cancer, ocular neovascularization, acute liver failure, Alzheimer's disease and cystic fibrosis. In another embodiment, the disease, disorder or condition is a disease, disorder or condition which is treatable by the delivery of siRNA to a cell such as hepatitis B, cancer, ocular neovascularization and acute liver failure. In a further embodiment, the disease, disorder or condition is a disease, disorder or condition which is preventable by the delivery of a genetic vaccine, for example a disease, disorder or condition involving a human pathogen such as hepatitis C and human papilloma virus or an animal pathogen such as porcine reproductive and respiratory virus.

The present application also includes a method of eliciting an immune response in a subject in need thereof, comprising administering a complex of the applicaiton or a vaccine composition of the application to the subject.

The following non-limiting examples are illustrative of the present application:

EXAMPLES

Example 1

Synthesis, Physiochemical Characterization and Nucleic Acid Binding Studies of Lysine Functionalized Nanodiamonds Detonation nanodiamonds (NDs) are carbon-based nanomaterials that, because, for example their size (4-5 nm), stable inert core, alterable surface chemistry, fluorescence, and/or biocompatibility, are emerging as bioimaging agents and promising tools for the delivery of biochemical molecules into cellular systems. However, ND particles possess a strong propensity to aggregate in liquid formulation media, restricting their applicability in biomedical sciences. The present studies explored the covalent functionalization of NDs with lysine to develop nanoparticles useful as nonviral vectors for transferring nucleic acids across cellular membranes.

A. Materials and Methods

I. Chemicals

Pharmaceutical-grade (ND98) carboxylic acid-functionalized NDs with an average particle size of 5 nm were purchased from Dynalene Inc. (Whitehall, Pa.). Tosoh Corporation (Grove City, Ohio) provided YTZ™ grinding media (0.05 mm). Dry dimethylformamide (DMF), 4M hydrochloric acid (HCl) (in dioxane) and ethidium bromide solution (~1% in water) were obtained from Sigma-Aldrich (Oakville, ON, Canada). Boc-lysine(Boc)-OH, Fmoc-NH(CH$_2$)$_3$NH$_2$.HCl, diisopropylethylamine (DIPEA), piperidine, and HATU [N,N,N',N'-tetramethyl-O-(7-azabenzotriazol-1-yl)uronium hexafluorophosphate] were obtained from ChemImpex International, Inc. (Wood Dale, Ill.). Dichloromethane (DCM) (high-performance liquid chromatography grade) was purchased from Thermo Fisher Scientific (Waltham, Mass.) and was dried using a solvent purification system (MBraun Incorporated, Stratham, N.H.). Thionyl chloride was acquired from Alfa Aesar (Ward Hill, Mass.). The pGTC-MV.IFN-GFP plasmid (encoding for interferon gamma and green fluorescent protein genes)[34] was used as a model plasmid for examining the binding properties of NDs. Anti-GFP siRNA was purchased from Ambion™ (Life Technologies Inc., Burlington, ON, Canada). Gibco™ UltraPure DNase/RNase-free water was obtained from Invitrogen (Life Technologies Inc, Burlington, ON, Canada). All chemicals were at ≥99% purity.

II. Preparation and Functionalization of NDs with Lysine

Unless otherwise stated, all reactions (Scheme 1) were carried out under a nitrogen atmosphere using standard Schlenk techniques. Ultrasonication was performed using a bath sonicator in some steps of the reaction scheme in order to improve the accessibility of chemical reagents to the surfaces of the nanosized particles.

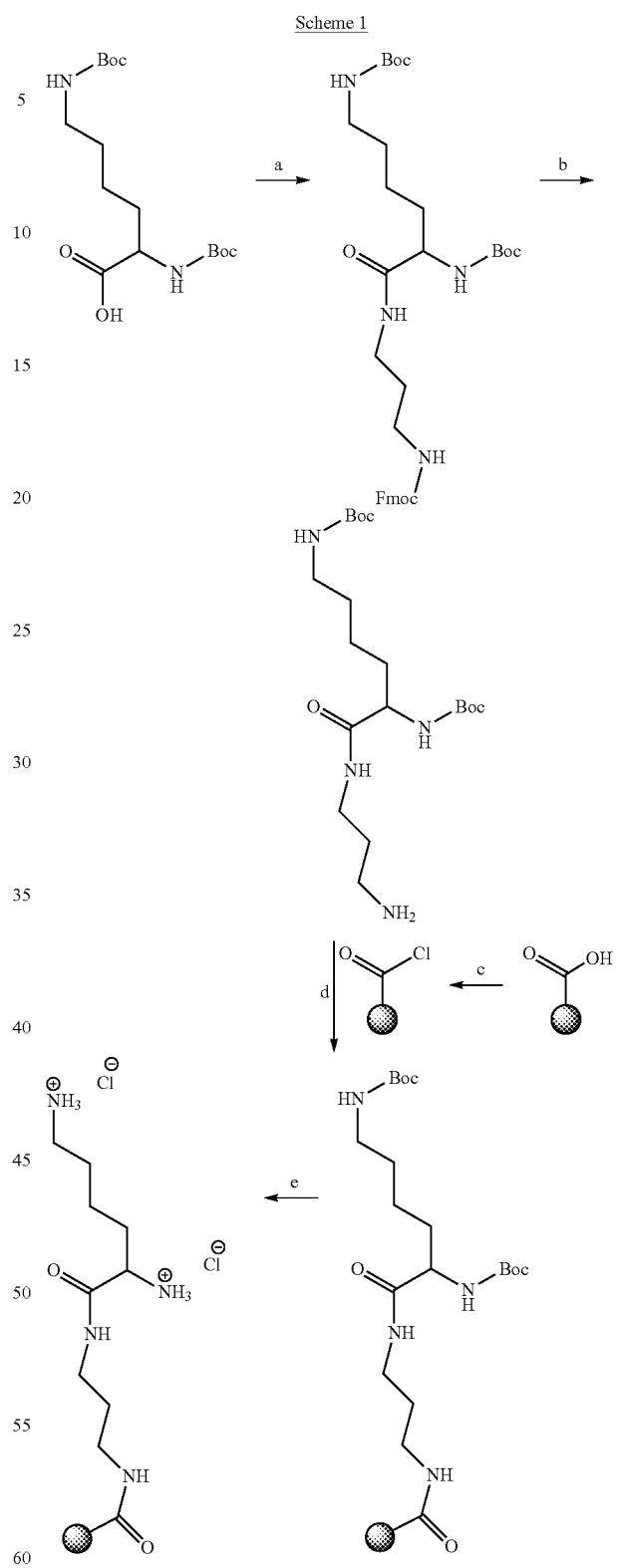

Scheme 1

Scheme 1 shows the preparation and functionalization of nanodiamonds (NDs) with lysine via a three-carbon-length linker: (a) synthesis of [N'—(N$^\alpha$,N$^\epsilon$-bis-Boc-lysyl),N''-(Fmoc)-diaminopropane], reagents, and solvents—Fmoc-NH(CH$_2$)$_3$NH$_2$.HCl, HATU [N,N,N',N'-tetramethyl-O-(7-azabenzotriazol-1-yl)uranium hexafluorophosphate], diisopropylethylamine, and dimethylformamide (DMF); (b) Fmoc deprotection, reagents, and solvents—50% (v/v) piperidine-DMF; (c) reoxidation of pristine carboxylated NDs, reagents—concentrated sulfuric acid and concentrated nitric acid, and preparation of acid chloride—functionalized NDs, reagents—thionyl chloride; (d) synthesis of Boc-protected lysine-functionalized NDs, solvent—DMF; (e) deprotection of Boc on lysine-functionalized NDs, reagents, and solvents—hydrochloric acid and dichloromethane.

Step a: synthesis of N'—($N^\alpha$,$N^\epsilon$-bis-Boc-lysyl),N"-(Fmoc)-diaminopropane In a dry Schlenk flask, Boc-lysine(Boc)-OH (8.661 mmol) was dissolved in dry DMF (15 mL), followed by the addition of HATU (10.82 mmol) and DIPEA (17.97 mmol). The reaction mixture was then stirred at room temperature for 15 minutes before the addition of a 10 mL solution of Fmoc-NH($CH_2$)$_3$$NH_2$.HCl (9.925 mmol) and DIPEA (10.92 mmol) in DMF. After 18 hours, DMF was removed from the reaction mixture under high vacuum, and the sample was dissolved in DCM (100 mL) and extracted with a saturated aqueous solution of sodium bicarbonate (4×100 mL). The organic phase was dried with sodium sulfate before removing the DCM under vacuum. Upon further purification by column chromatography (Silica Gel 60, EMD Inc, Mississauga, ON, Canada) using a methanol-chloroform (1:9, v/v) solvent system, a pale yellow solid compound, N'—($N^\alpha$,$N^\epsilon$-bis-Boc-lysyl),N"-(Fmoc)-diaminopropane was obtained with a yield of 79%.

Step b: Fmoc deprotection of [N'—($N^\alpha$,Nϵ-bis-Boc-lysyl), N"-(Fmoc)-diaminopropane], The removal of Fmoc from [N'—($N^\alpha$,$N^\epsilon$-bis-Boc-lysyl), N"-(Fmoc)-diaminopropana], was carried out using 300 mg of the compound and 10 mL of a 50% (v/v) piperidine-DMF mixture at room temperature. The recovered Fmoc-deprotected product was used in step d without further purification.

Step c: Reoxidation of NDs and Preparation of Acid Chloride-Functionalized NDs

In order to promote the surface functionalization of the pristine carboxylated NDs (pNDs), they were reoxidized in a mixture of concentrated nitric and sulfuric acids (1:3, v/v) with overnight ultrasonication.[35,36,37] The reoxidized NDs (rNDs) were subsequently dialyzed with water using a cellulose membrane with an average pore radius of 2.4 nm until neutral pH was achieved, and then they were freeze-dried. To promote amide bond formation between the NDs and the Fmoc-deprotected product obtained in Step B, the surface carboxylic acid groups of the rNDs were converted into more reactive acyl chloride functional groups using an excess of thionyl chloride[38,39,40] in the presence of YTZ grinding media. This mixture was ultrasonicated at a frequency of 25 kHz in a bath sonicator (Transsonic TI-H-5 Ultrasonicator; Elma Hans Schmidbauer GmbH and Co K G, Singen, Germany) for 22 hours, refluxed for 5 hours at 70° C., and ultrasonicated for 48 hours. Finally, the sample was dried overnight under high vacuum.

Steps d and e: Preparation of Lysine-Functionalized NDs

The Fmoc-deprotected product obtained in Step B was dissolved in 10 mL of DMF and added to the acid chloride-functionalized NDs (100 mg) suspended in 5 mL of DMF. The heterogeneous mixture was refluxed for 45 minutes at 75° C., ultrasonicated for 72 hours, and lyophilized. Boc removal (step e, Scheme 1) was achieved by suspending the Boc-protected lysine-functionalized NDs (fNDs) in 10 mL of DCM and 10 equivalents of HCl (4 M in dioxane)[41] for 90 minutes. This produced positively charged fNDs capable of electrostatic interactions with the negatively charged phosphate groups of DNA. The fNDs were dialyzed with ethanol followed by water, using a cellulose membrane with an average pore radius of 2.4 nm, before being freeze-dried.

III. Nuclear Magnetic Resonance and Mass Spectroscopic Characterization of

N'—($N^\alpha$,$N^\epsilon$-bis-Boc-lysyl), N"-(Fmoc)-diaminopropane

Proton nuclear magnetic resonance ($^1$H NMR) spectra were recorded on a Bruker 500 MHz Avance spectrometer (Bruker BioSpin, Milton, ON, Canada). Chemical shifts for $^1$H NMR are reported in ppm in reference to the residual $^1$H resonances of deuterated chloroform at δ 7.26. The mass spectrum was obtained using the QSTAR™ XL MS/MS System (ESI-Q-TOF) (Applied Biosystems, Toronto, ON, Canada).

IV. ND Dispersions

NDs (2 mg/mL) in reverse osmosis-purified water (Millipore, Milford, Mass.) were ultrasonicated at a frequency of 25 kHz for 4 hours and centrifuged at 5200 g for 6 minutes. The resulting dispersions were used for Raman spectroscopy, atomic force microscopy (AFM), gel electrophoresis, and zeta potential and size distribution measurements. For the dispersion stability experiment, the ND samples were sonicated for 20 minutes and allowed to settle for 3 days at room temperature without centrifugation.

V. Raman Spectroscopic Measurements

Raman spectroscopic measurements were carried out using a Renishaw Invia Reflex microscope (Renishaw Inc, Chicago, Ill.) fitted with a 514.5 nm argon ion laser (Spectra-Physics™ 163-M42-010 Spectra Physics™, Santa Clara, Calif.) and 1800 line/mm grating. Aqueous dispersions of NDs were dropped onto a gold-coated silicon wafer (Platypus Technologies, Madison, Wis.) and allowed to dry. A Leica N PLAN Objective (Leica Microsystems, Buffalo Grove, Ill.) 50× with a numerical aperture of 0.75 was used to focus the sample, and backscattered Raman signals were detected using a Peltier-cooled charge-coupled device. Instrument calibration was verified using an internal silicon wafer, measured at 520 $cm^{-1}$. The Raman spectra of NDs and N'—($N^\alpha$, $N^\epsilon$-bis-Boc-lysyl),N"-(Fmoc)-diaminopropane were acquired in the static scanning mode. Baseline correction was performed using Renishaw WiRE software (v3.2; Renishaw Inc).

VI. Infrared Spectroscopy

Infrared (IR) spectra of all materials were recorded on a Bruker IFS 66v/S Fourier transform spectrometer (Bruker Optics, Billerica, Mass.) in the mid-IR range using a liquid nitrogen-cooled mercury cadmium telluride detector at the Canadian Light Source, University of Saskatchewan, Saskatoon, SK, Canada. All sample measurements were carried out in the solid state using pelletized, homogeneous powder dispersions of the materials in a potassium bromide matrix. For N'—($N^\alpha$,$N^\epsilon$-bis-Boc-lysyl),N"-(Fmoc)-diaminopropane, a PIKE MIRacle™ Single Reflection ATR (PIKE Technologies, Madison, Wis.) accessory was used in order to avoid potential pressure-induced changes. In all cases, 512 individual interferograms were averaged for both the background and the sample measurements from which the absorbance spectra were calculated.

Data analysis was performed with the Bruker OPUS software package (v6.5; Bruker Optics). Baseline correction was performed on all raw absorbance spectra using the built-in concave rubber band correction routine (number of baseline points: 32; number of iterations: 2) to strictly avoid the introduction of any artificial features into the spectra.

VII. Size and Zeta Potential Measurements

Particle size and zeta potential measurements were obtained using a Malvern Zetasizer Nano ZS instrument (Malvern Instruments Ltd, Malvern, Worcestershire, UK).

The size distribution of NDs in water was obtained by measuring the light scattered ($\theta=173°$) by particles (dynamic light scattering, DLS) illuminated with a laser beam, using the CONTIN algorithm to analyze the decay rates that are a function of the translational diffusion coefficients of the particles, D. The measured data are reported in volume distribution. The hydrodynamic radius, $R_H$, of the particles was estimated using the Stokes-Einstein equation ($R_H=kT/6\pi\eta qD$), where k is the Boltzmann constant, T is the temperature, and $\eta$ is the viscosity of the solution. This analysis gives an estimate of size based upon the hydrodynamic radius of spherical particles having a translational diffusion coefficient equivalent to the actual particles. Size distribution values were derived from three measurements, each consisting of a minimum of ten individual runs.

Zeta potential measurements were based upon laser Doppler electrophoresis and phase analysis light scattering analysis. The reported zeta potentials are the average of three measurements, each derived from a minimum of ten individual runs.

VIII. Atomic Force Microscopy (AFM)

AFM images were obtained in intermittent contact mode using an atomic force microscope (Agilent 4500; Agilent Technologies, Inc, Chandler, Ariz.) equipped with a silicon cantilever (T190R; Nanoscience Instruments, Inc, Phoenix, Ariz.).

The specifications of the silicon cantilever include a force constant of approximately 45 N/m and a resonant frequency of approximately 190 kHz. A small volume (25 μL) of ND dispersion samples was dropped onto a freshly prepared poly-L-lysine-coated mica substrate and allowed to incubate for 1 minute. The substrate was then rinsed with purified water and dried gently using a stream of nitrogen gas. The amplitude range was between 1 and 1.5 V for all measurements, while the amplitude ratio for set point to free air oscillation was 0.80. Ambient conditions were maintained throughout the experimental procedure, and the scan rate used for image acquisition ranged from 0.5 to 1 lines per second (512 pixels per line). Line scan profiles were obtained for three particles from each sample, and the reported particle sizes were determined from the particle height (SPIP, v5.1.6; Image Metrology A/S, Lyngby, Denmark).

IX. Thermogravimetric Analysis

Thermogravimetric analysis was carried out using a TGA Q50 (TA Instruments-Waters LLC, New Castle, Del.). The furnace tube carrying the sample was heated to 450° C., and the percentage weight loss was obtained as a function of the temperature. The surfaces of the pNDs and rNDs were considered dominated by carboxylic acid functional groups, and surface loading was calculated using the following equation:

$$\text{Surface loading} = \frac{\text{Number of } moles_{lost\ functional\ group}}{Weight_{total\ sample} - Weight_{lost\ sample}}$$

Any loss in weight that occurred below 115° C. was attributed to water and was excluded from estimates of surface loading.

IX. Agarose Gel Electrophoresis

Electrophoresis was performed in 1% (for pDNA) or 2% (for siRNA) agarose gels prepared with tris-acetate ethylenediaminetetraacetic acid buffer and ethidium bromide at a final concentration of 1 μg/mL. The amounts of pDNA and siRNA in each sample were 500 and 400 ng, respectively. Complexes of fNDs-pDNA and fNDs-siRNA with different weight ratios (fNDs:nucleic acid component ranging from 1:1 to 50:1) were prepared in ultrapure water and incubated for 30 minutes at room temperature. Uncomplexed pDNA and siRNA were used as standards. All samples were loaded into the gel using 30% glycerol and were subjected to electrophoresis at 100 V using a Bio-Rad PowerPac HC electrophoresis apparatus (Bio-Rad Laboratories, Inc, Mississauga, ON, Canada) for 1 hour for pDNA or 45 minutes for siRNA. The gels were then imaged using an AlphaImager™ imaging system (Alpha Innotech Corporation, San Leandro, Calif.) to detect ultraviolet fluorescence.

X. Size and Zeta Potential Measurements of fND-pDNA and fND-siRNA Complexes

Size and zeta potential measurements of fND-genetic material complexes formed at weight ratios in the range between 1:1 and 50:1 were performed using the Zetasizer Nano ZS (Malvern Instruments Ltd). Different sets of samples were prepared for analysis of size and zeta potential using the same sample preparation technique as described for agarose gel electrophoresis assay. Each reported value was obtained from the Z-average size, and each value is the average of four measurements, each consisting of a minimum of ten individual runs.

B. Results and discussion

I. Synthesis of fNDs

The synthesis of the lysine functionality intermediate (N'—(N$^\alpha$,N$^\epsilon$-bis-Boc-lysyl),N"-(Fmoc)-diaminopropane) and its subsequent covalent functionalization with NDs was performed (Scheme 1). The $^1$H NMR spectrum of N'—(N$^\alpha$, N$^\epsilon$-bis-Boc-lysyl),N"-(Fmoc)-diaminopropane was used to establish its structure: $^1$H NMR (500 MHz, deuterated chloroform) δ 7.76 (d, J=7.5, 2H, fluorenyl), 7.61 (d, J=7.4, 2H, fluorenyl), 7.39 (t, J=7.5, 2H, fluorenyl), 7.31 (t, J=7.4, 2H, fluorenyl), 6.67 (s, 1H, NH), 5.48 (s, 1H, NH), 5.23 (s, 1H, NH), 4.67 (s, 1H, NH), 4.38 (d, J=7.0, 2H, fluorenyl-CH$_2$), 4.21 (t, J=7.0, 1H, fluorenyl-CH), 4.04 (s, 1H), 3.28 (m, 2H), 3.20 (m, 2H), 3.10 (m, 2H), 1.63-1.82 (m, 4H), 1.48 (m, 2H), 1.43 (s, 18H, Boc-(CH$_3$)$_6$), 1.37 (m, 2H). The synthesis of N'—(N$^\alpha$,N$^\epsilon$-bis-Boc-lysyl),N"-(Fmoc)-diaminopropane was also confirmed by mass spectroscopic measurements: electrospray ionization mass spectrometry mass-to-charge ratio calculated for $C_{34}H_{48}N_4O_7$: 624.3523 [M]. found 625.3603 [M+1]$^+$.

Figure 1:
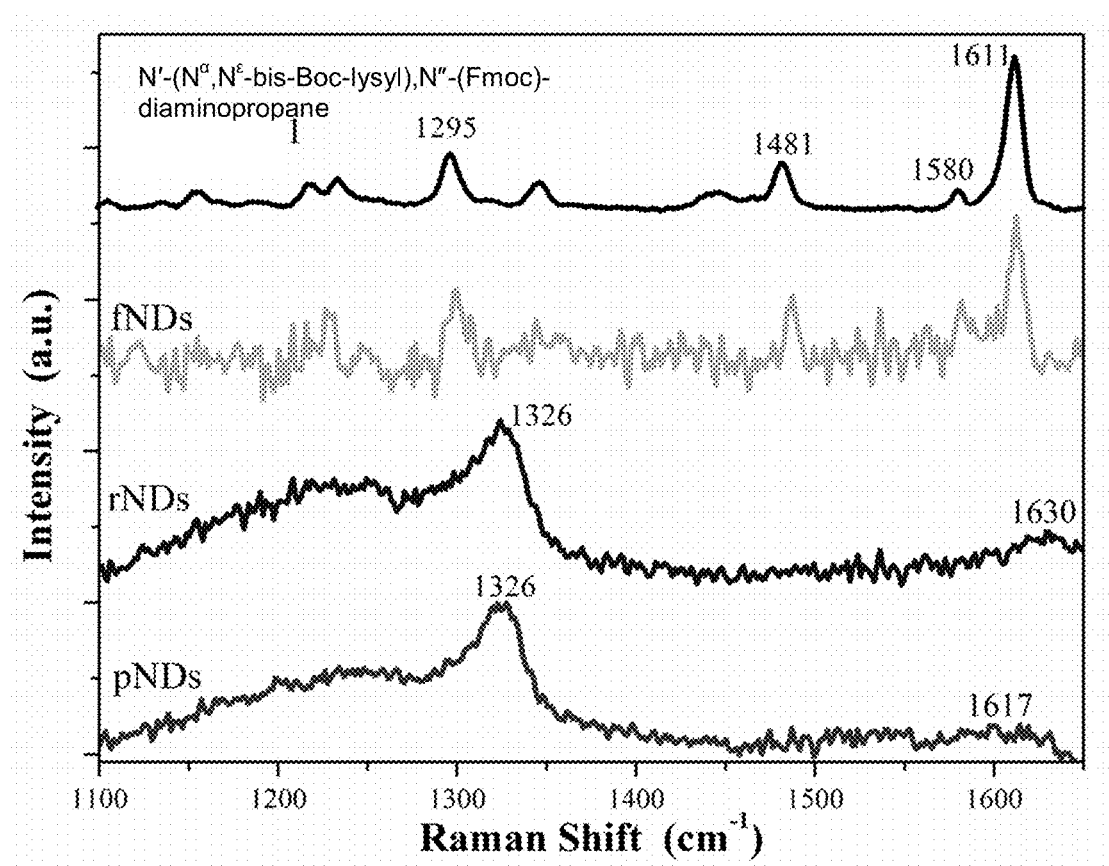
FIG. 1 shows a baseline-corrected static scan Raman spectra of the pristine carboxylated nanodiamonds (pNDs), re-oxidized nanodiamonds (rNDs), lysine functionalized nanodiamonds (fNDs), and [N'—(N$^\alpha$,N$^\epsilon$-bis-Boc-lysyl),N"-(Fmoc)-diaminopropane] using a 514.5 nm excitation source in exemplary embodiments of the present application. A total of 128 accumulations were collected for pNDs and rNDs, while the spectrum of fNDs was obtained from a single acquisition.

II. Surface Functionalization Assessed by Raman Spectroscopy, IR Spectroscopy, Zeta Potential, and Thermogravimetric Measurements To provide evidence of functionalization of NDs with the lysine functionality, Raman spectroscopy of pNDs, rNDs, fNDs, and N'—(N$^\alpha$,N$^\epsilon$-bis-Boc-lysyl),N"-(Fmoc)-diaminopropane was performed (FIG. 1). The pNDs showed the signature peak of diamond at 1326 cm$^{-1}$, which is downshifted in frequency compared with the 1332 cm$^{-1}$ Raman peak assigned to bulk diamond.[42] This frequency shift could be attributed to the smaller size of NDs, as explained by the phonon confinement model.[43,44] The existence of the diamond peak at ~1326 cm$^{-1}$ after the reoxidation process suggests that the intrinsic diamond structure was unaltered by the harsh acidic oxidation conditions. A broad peak was also observed at 1617 cm$^{-1}$ on the pND spectra, which could have arisen because of overlapping signals from the in-plane stretching of the sp$^2$ carbon (G-mode) at ~1590 cm$^{-1}$, oxygen-hydrogen (O—H) bending at ~1635 cm$^{-1}$, and carbon-oxygen double bond stretching of the carboxylic acid group at ~1740 cm$^{-1}$.[45]

The suppression of the D-band of graphitic carbon (~1410 cm$^{-1}$) in the Raman spectra of pristine and reoxidized NDs supports the existence of high ratios of sp$^3$/sp$^2$ carbon in NDs.[46] After reoxidation, the emergence of a prominent band at ~1630 cm$^{-1}$ was accompanied by a decrease in the 1590-cm$^{-1}$ band of graphitic carbon, supporting the use of mineral acids in the oxidation of graphitic carbon. Raman spectroscopy was not used to monitor carboxylic acid vibrations in any of the samples.

The Raman spectrum of N'—(N$^\alpha$,N$^\epsilon$-bis-Boc-lysyl),N''-(Fmoc)-diaminopropane revealed noticeable peaks of carbon-hydrogen (C—H) deformation at ~1481 cm$^{-1}$, amide III at ~1295 cm$^{-1}$, and amide I at ~1611 cm$^{-1}$, with a weak shoulder representing amide II observed at ~1580 cm$^{-1}$. The fND spectrum was acquired by a single scan, as additional laser scanning resulted in burning of the fNDs. In comparison with the Raman spectrum of N'—(N$^\alpha$,N$^\epsilon$-bis-Boc-lysyl),N''-(Fmoc)-diaminopropane, the Raman spectrum of the fNDs exhibited amide I (~1612 cm$^{-1}$), amide II (~1582 cm$^{-1}$), amide III (~1299 cm$^{-1}$), and C—H deformation (~1482 cm$^{-1}$) peaks, indicating that the functionalization had been successful. The Raman peak of fNDs at 1299 cm$^{-1}$ is very broad in comparison with the corresponding peak of N'—(N$^\alpha$,N$^\epsilon$-bis-Boc-lysyl),N''-(Fmoc)-diaminopropane because of interference from the diamond signal. The covalent modification of the NDs with the lysine functionality, which has a much higher mass than carbon, caused a further downshift in the frequency of the diamond signal in fNDs.

Figure 2:
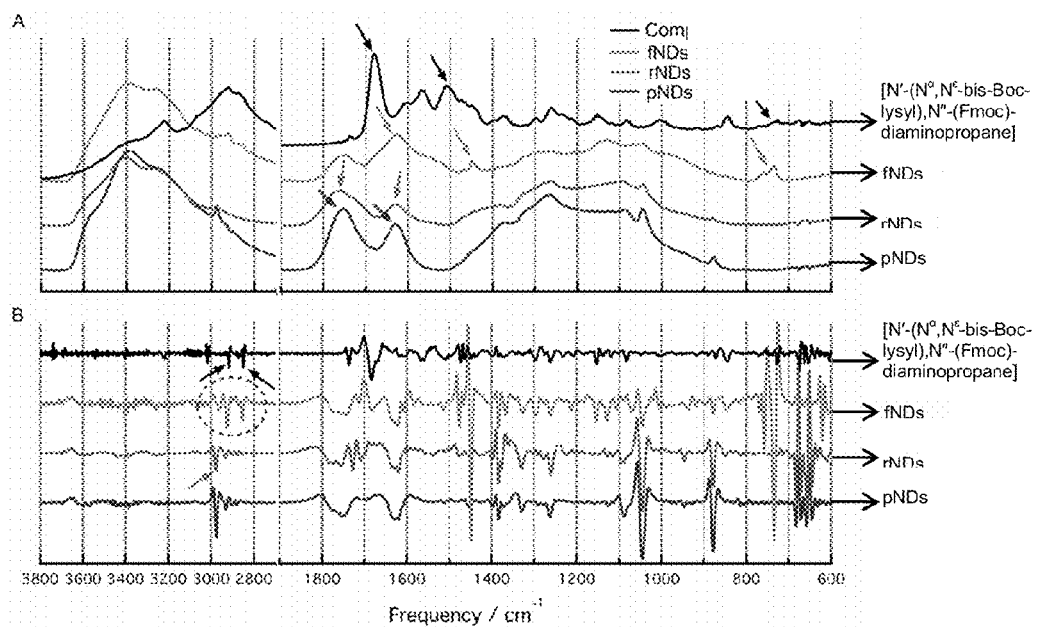
FIG. 2 shows baseline-corrected absorbance and attenuated total reflectance: (A) infrared spectra of the pristine carboxylated nanodiamonds (pNDs), reoxidized nanodiamonds (rNDs), lysine-functionalized nanodiamonds (fNDs), and [N'—(N$^\alpha$,N$^\epsilon$-bis-Boc-lysyl),N"-(Fmoc)-diaminopropane] in exemplary embodiments of the present application.

Overall, the Raman spectra obtained in the present study support the formation of fNDs. However, as the Raman cross section is smaller than the fluorescence cross section, it is likely that fluorescence swamps the Raman signals. Hence, to strengthen the evidence of functionalization, IR spectroscopy, a complementary technique to Raman spectroscopy, was performed at various stages of functionalization, including on N'—(N$^\alpha$,N$^\epsilon$-bis-Boc-lysyl),N''-(Fmoc)-diaminopropane (FIG. 2A). Band positions are indicated by the second derivative curves (FIG. 2B).

The ND spectra showed that characteristic bands at ~1045 cm$^{-1}$ and ~1262 cm$^{-1}$ due to vibrations of ether-like groups[47] might arise from the covalent bonding of inter-particulate carboxylic and/or hydroxyl groups, as well as bands in the C—H stretching region at ~2900 cm$^{-1}$ due to vibrations arising from the C—H bonds present on the surface of the NDs. In fact, a very broad IR spectrum ranging from 1000 to 1500 cm$^{-1}$ is identified as the "fingerprint region" of NDs in the literature.[46]

All ND spectra were found to have features in the carbonyl region (~1760 cm$^{-1}$), suggesting that the raw material was already somewhat oxidized. While not wishing to be limited by theory, the peaks at ~1630 cm$^{-1}$ (O—H bending) and ~3400 cm$^{-1}$ (O—H stretching) may have originated because of either the water adsorbed onto the NDs/potassium bromide or the presence of covalently bonded hydroxyl functional groups on the surface of the NDs.

Comparing the spectra of fNDs with those of pNDs and rNDs, it is evident from both the peak height and shape of the band located at ~1630 cm$^{-1}$ that the functionalization reaction was successful. The presence of an amide I band from ~1640 to 1690 cm$^{-1}$ and an amide II shoulder from ~1510 to 1580 cm$^{-1}$ in the fND spectrum provide further evidence of functionalization. These bands were also observed in the N'—(N$^\alpha$,N$^\epsilon$-bis-Boc-lysyl),N''-(Fmoc)-diaminopropane spectrum at a slightly higher frequency. The peak at ~730 cm$^{-1}$ in the spectra of both fNDs and N'—(N$^\alpha$,N$^\epsilon$-bis-Boc-lysyl),N''-(Fmoc)-diaminopropane is associated with the rocking mode of hydrocarbons with more than four methylene groups,[48] while a methylene deformation band can be observed at ~1465 cm$^{-1}$. A combination of the spectra of the two starting materials (rNDs and N'—(N$^\alpha$,N$^\epsilon$-bis-Boc-lysyl), N''-(Fmoc)-diaminopropane) was recognizable in the C—H stretching region of the second derivative spectra (FIG. 2B, red oval shape), further verifying the lysine functionalization of NDs.

The functionalization of NDs with lysine was also confirmed by the zeta potential measurements (Table 1). The pNDs showed a negative zeta potential of −21.1 mV, suggesting that negatively charged surface functional groups such as carboxylate were present. After reoxidation, the mean zeta potential shifted to −23.7 mV, indicating a slight increase in the density of negatively charged surface groups. The lysine-modified NDs showed a positive zeta potential of +48.9 mV, demonstrating the predominance of a large number of positively charged (amine) groups on their surfaces.

Thermogravimetric analyses were performed to provide quantitative estimates of the surface loading of functional groups attached to the NDs. The thermograms of the pNDs and rNDs did not show any considerable weight loss in the temperature range of 30° C.-440° C., indicating that NDs are thermally stable in this range (FIG. 3).

The surface loading of the pNDs, rNDs, and fNDs was calculated (Table 2) from their respective thermograms. Providing that the surfaces of pNDs and rNDs are dominated by carboxylate groups, the estimated surface coverage was 0.35 mmol g$^{-1}$ for the pNDs and 1.0 mmol g$^{-1}$ for the rNDs, while the fNDs demonstrated a surface loading of 1.7 mmol g$^{-1}$ of ND. This coverage is greater than was found in a previously reported study of the covalent functionalization of long-chain alkyl groups on the surface of NDs (0.3-0.4 mmol g$^{-1}$).[26] The high surface functionalization confers a high nucleic acid-binding capacity to the nanomaterial.

III. Dispersion of NDs in Aqueous Medium and AFM Imaging

For biomedical applications, the stability of the biomaterial in aqueous medium is important, as aggregation can lead to toxic effects in biological systems. In the present study, the pND, rND, and fND samples were dispersed in water and the stability of the resultant hydrosols was monitored for 3 days. While sedimentation of the pND and rND hydrosols was observed to occur within the first 5 minutes of incubation, fNDs remained stable even after 3 days (FIG. 4). This was in agreement with the results of the above-discussed zeta potential measurements, which also indicated that fNDs have colloidal stability in water. According to the DLVO theory (Derjaguin-Landau-Verwey-Overbeek), repulsive forces dominate among particles in systems with a zeta potential higher than +30 mV, which prevents aggregation and flocculation of the colloidal system.[49] As in table 1, the fNDs of the present study have a zeta potential of +49 mV.

While not wishing to be limited by theory, the high aqueous dispersibility of fNDs may be explained by the greater hydrophilicity of the lysine hydrochloride functional groups found on their surfaces,[50] as well as inter-particle repulsion due to the positively charged amine groups of lysine. On the other hand, the sedimentation of pNDs and rNDs is most likely due to van der Waals' forces, dipole-dipole interactions, and/or hydrogen bonding between the surface functional groups. A similar dispersion behavior has been shown to occur with adenosine-functionalized multiwalled carbon nanotubes, which exhibit greater aqueous solubility than pristine, reoxidized forms.[36]

Particle size is also considered to be an important parameter in the development of bionanomaterials. Therefore, hydrodynamic particle size measurements were carried out in this study to gain more insight into the suitability of fNDs for use in gene delivery applications (FIG. 5). The pNDs were found to have a very wide size distribution (polydispersity index [PDI]=0.56) when dispersed in aqueous medium, with a major fraction of the particles having size distributions centered at 1280 nm. Reoxidation did not improve the particle dispersibility considerably; while a shift towards smaller size with a peak at 531 nm was observed, the broadness in the size distribution was maintained (PDI=0.59). No NDs smaller than 50 nm in diameter were detected in either pND or rND samples. In addition to the physical inter-particle interactions that cause agglomeration of pristine and reoxidized NDs, the surface carboxylate groups can also result in the formation of tightly bound aggregates via anhydride bond formation.[25]

In contrast, when the size of the fNDs was examined, the surface functionalization was found to result in a large reduction in aggregate size, with the majority of particles centering at 21 nm. A narrower size distribution (PDI=0.25) was also observed when compared with the pND and rND particle distributions. The fNDs in this study were also found to have considerably smaller hydrodynamic radii than those obtained in a previous study that functionalized NDs with glycine through a silane linker (peak at >350 nm).[25] The disaggregation of fNDs also contributes to their dispersion stability in aqueous media.

AFM was used to determine the topographic features (FIG. 6A) and size (FIG. 6B) of pNDs (i), rNDs (ii), and fNDs (iii). Since substrate surface features and drying could cause aggregation of the particles, the height rather than the diameter is reported for particle size. The pNDs formed irregularly shaped aggregates of 40-80 nm, while the rNDs appeared to be round with a comparatively smaller aggregate size of 20-60 nm.

In agreement with the DLS measurements, AFM images provided visual evidence for the disaggregation of NDs after their functionalization with the lysine functionality (FIG. 6A, iii). The particles of fNDs were found to be 3-5 nm in size.

Besides aggregation on a solid mica surface, the environment of the sample and the principle of the measurement technique can also influence the size determination of particles, as can be observed in the differences in particle sizes determined by DLS and AFM. DLS measures the average hydrodynamic radius of nanoparticles in liquid medium under the assumption that they are spherical in shape, while AFM measures the height and diameter of individual particles devoid of their native environment. The different principles utilized by these two techniques for size determination have also been considered to be a cause of size variation in an earlier study.[51]

IV. Binding of fNDs to Nucleic Acids

As the nanosize, positive zeta potential, and hydrophilic properties of fNDs suggest that they may be useful in biomedical applications, the applicability of fNDs as nonviral vectors was evaluated by examining their ability to bind and protect pDNA and siRNA. Weak binding can lead, for example to the disruption of vector-nucleic acid complexes by negatively charged protein molecules, leading to inefficient gene delivery.[52] Therefore, the binding stability of complexes is useful for the protection of genetic material against enzymatic degradation and the production of high levels of gene expression in cellular systems.[34]

In this study, the binding efficacy of the fNDs for genetic material was examined by carrying out gel electrophoresis assays on a series of fNDs:pDNA (FIG. 7A) and fNDs:siRNA (FIG. 7B) weight ratios. The naked pDNA revealed two major bands (FIG. 7A, lane 1), corresponding to the two different forms of pDNA: a highly mobile supercoiled form and a lesser mobile band representing the circular form. The complexes obtained by using equal weight ratios of fNDs and pDNA were not stable, as the migration of pDNA was not hindered (FIG. 7A, lane 2). However, no pDNA bands were detected at fNDs:pDNA weight ratios of 5:1 and above (lanes 3-12), indicating that the formation of a complex between the pDNA and the fNDs hampered its migration towards the anode. For siRNA (FIG. 7B), the trend of binding was found to be similar. However, complex formation was comparatively less efficient than that observed with pDNA, as siRNA was detected in its free form at weight ratios of 5:1 (FIG. 7B, lane 3) and 10:1 (lane 4). The band intensity gradually decreased with an increase in the amount of fNDs, and only a negligible amount of siRNA was detected in its free form at weight ratios of 20:1 and higher (lanes 6-12).

As the size of a nanomaterial-nucleic acid complex can also have an impact on transfection efficacy, it would be useful if a delivery agent condensed genetic material to inhibit its degradation by nucleases and promote cellular internalization. A size in the range of 100-300 nm is considered useful for producing efficient transfection.[53] In addition to a useful size, the surface charge of transfection complexes also has an effect on the intracellular delivery of transgenes, and an overall positive charge is desired in order to promote internalization across the negatively charged cell surface by means of favorable electrostatic interactions.[54]

In order to explore these parameters, the size and zeta potential of particles formed at various weight ratios of fNDs: pDNA and fNDs:siRNA were measured. An increase in the weight proportion of fNDs to genetic material from 1:1 to 50:1 resulted in a shift in zeta potential from negative to positive, indicating that no free genetic material was available at higher weight ratios. The fND:pDNA particles exhibited considerable aggregation (precipitate) at a 6:1 weight ratio because of a neutral zeta potential (FIG. 8A), while this neutral zeta potential was reached at a much higher weight ratio (20:1) in the fND-siRNA system (FIG. 8B).

With an increase in ratio from 10:1 to 50:1, particle size was found to stabilize around 110 nm for fND-pDNA complexes (FIG. 8A) and was less than 280 nm for the fND-siRNA complexes (FIG. 8B). In the case of the fND-pDNA complexes, the zeta potential reached +40-50 mV at ratios of 30:1 and beyond, while a positive zeta potential of nearly 30 mV was attained at a ratio of 50:1 in fND-siRNA complexes. These results demonstrate the ability of fNDs to condense pDNA and form complexes with pDNA and siRNA within a size range suitable for producing efficient transfection. These size and zeta measurements correlate well with those from the gel electrophoresis assay, indicating that the retardation of nucleic acid material coincides with the electroneutrality of the "diamoplexes."

In this study, the ratio of lysine functionality present per base pair of pDNA and siRNA was also calculated based on the surface loading of the fNDs and the number of base pairs of nucleic acids (Table 3). The differences in the binding behavior of these two genetic materials to the fNDs can be attributed to structural differences of the circular pDNA having 5805 base pairs and linear siRNA having only 21 base pairs. The formation of complexes between nanoparticles and siRNA has also been observed to occur at a higher weight ratio than nanoparticles and pDNA in previous studies involving chitosan nanoparticles.[55,56]

While not wishing to be limited by theory, a suggested model for the formation of complexes between fNDs and pDNA or siRNA, taking into account the binding behavior, size, and zeta potential measurements of the complexes, as well as the structures of the genetic materials, is shown in FIG. 9. In this model, the pDNA is thought to form a spherical nanostructure with positively charged fNDs, while the structural configuration of linear siRNA with fNDs is rather complex, involving several linear siRNA sequences.

Example 2

Cellular Studies of Lysine-Functionalized Nanodiamonds

One of the basic requirements for the consideration of a material for use in delivering therapeutic agents into biological systems is its cellular interaction, leading to successful internalization. Previous studies showed the ability of nanodiamonds (NDs) to be internalized by mammalian cells via passive diffusion, clathrin-mediated endocytosis and macropinocytosis.[57,58]

In the present study, Raman-fluorescence and elastic light scattering mapping were applied to explore the interaction of NDs with human cells. The use of laser scanning confocal microscopy to identify the localization of NDs in a human cell line using the autofluorescence of NDs as a detection marker was also investigated. Some advantages and disadvantages of employing these techniques as tools for in vitro tracking of NDs are discussed.

In addition to cellular interaction and consequent internalization, another requirement of a delivery agent to be used in biological systems is its biocompatibility.[28,6] Although earlier studies have demonstrated negligible in vitro toxicity of NDs[27,28,59,60,61,18], the cell type, size, surface properties and/or shape of nanoparticles can influence the biocompatibility.[62] Therefore, the cytotoxicity of pristine carboxylated nanodiamonds (pNDs) and lysine-functionalized nanodiamonds (fNDs), with and without serum, was tested in the present studies using a human cell line.

Flow cytometry was used to assess the efficacy of fNDs to deliver anti-green fluorescent protein (GFP) small interfering RNA (siRNA) in mammalian cells expressing GFP.

A. Materials

HeLa cells (human cervical cancer cells), Eagle's Minimum Essential Medium (EMEM), and Dulbecco's Modified Eagle Medium (DMEM) were obtained from American Type Culture Collection, VA, USA. HeLa cells expressing GFP (HeLa/GFP) were acquired from Cell Biolabs, Calif., USA. Fetal bovine serum (FBS) and 0.1 mM MEM Non-Essential Amino Acids were acquired from Gibco, ON, Canada. Lipofectamine™ RNAiMAX and (Dimethylthiazol-2-yl)-2,5-diphenyltetrazolium bromide (MTT) reagent were purchased from Invitrogen, ON, Canada. Trypsin and antibiotics were obtained from Sigma Aldrich, ON, Canada, and anti GFP siRNA was purchased from Ambion, ON, Canada. Cell culture plates and polystyrene petri dishes were purchased from Falcon B D, ON, Canada. Gold-coated silicon wafer was supplied by Platypus Technologies, WI, USA and coverslips were purchased from VWR International, ON, Canada.

B. Methods

I. Cell Culture

HeLa cells were grown in EMEM supplemented with 10% FBS and 1% antibiotic/antimycotic agents. The growth medium for HeLa/GFP cells was DMEM supplemented with 10% FBS, 0.1 mM non-essential amino acids and 1% antibiotic/antimycotic agents. All the cells were grown to 70-80% confluency at 37° C. in a humidified incubator supplied with 5% $CO_2$. The second passage from the initiation of the frozen cell line was used for all of the experiments. In general, no more than 12 passages from the original population were used for any of the experiments. In all of the assays, the media of the cells was replaced with fresh unsupplemented media one hour prior to the treatment and the cells were incubated at 37° C. and 5% $CO_2$ in a humidified incubator.

II. ND Dispersion Preparation

Unless stated, the dispersions of NDs for all the assays were prepared in unsupplemented media with 4 hours of bath sonication at a frequency of 25 kHz without heating.

III. Imaging of Cells Incubated with NDs Using Raman-Fluorescence and Backscattering Mode Microspectroscopic Mapping Raman-fluorescence and backscattering mode mapping of cells incubated with NDs was carried out using a Renishaw Invia Reflex microscope. Pieces of gold-coated silicon wafer were washed with double distilled water and 70% ethanol, and placed in the wells of a 48-well plate. HeLa cells, at a density of 10,000 cells per well were allowed to adhere to the gold substrate 24 hours prior to ND treatment. Then, the media of each well was replaced with 200 µl of the ND dispersion prepared at a concentration of 200 µg/mL. After 7 hours, the media was supplemented with FBS to a final concentration of 10%. The cells were incubated with NDs for 24 hours, and then washed three times with sterile phosphate buffer saline (PBS) (5 minutes each) using a plate shaker to remove non-internalized NDs. Gold wafers with cells were placed in a polystyrene Petri dish containing 2 mL of PBS.

Raman-fluorescence and backscattering mode mapping of the cells was carried out with 514.5 nm (1800 lines/mm grating) and 1060 nm (1200 lines/mm grating) lasers, respectively. A long working-distance 50× objective allowed the measurements of the cells in PBS. The instrument was calibrated using a silicon wafer measuring at 520 $cm^{-1}$. The laser intensity during the Raman-fluorescence mapping was 100%, while the backscattering mapping was performed with 0.1% (pNDs treated cells and control) and 0.05% (fNDs treated cells and control) laser intensity. The lower and upper intensity limits of the Look Up Table, used to create the map of control and treated cells, were set manually from 3400 to 4000 (Raman-fluorescence maps), 13500 to 38000 (backscattering maps using 0.1% laser intensity) and 3153 to 5594 (backscattering maps using 0.05% laser intensity). The Raman-fluorescence maps were constructed using signal to axis intensity values from 1315 to 1345 $cm^{-1}$. The intensity of the laser at 1058.22 nm was used for constructing the backscattering maps. A rainbow color scheme was chosen for representing the intensity in the maps, where violet represents the lowest intensity and red represents the highest intensity of the scattered light.

IV. Imaging of NDs with Cells Using Laser Scanning Confocal Microscopy

To evaluate whether NDs can be detected in the cells based upon their intrinsic fluorescence, laser scanning confocal microscopy was performed. HeLa cells seeded at a density of 40,000 cells per well were allowed to adhere to a coverslip placed in 12-well plate for 24 hours. The media of cells was replaced with 1 mL of NDs dispersion prepared at a concentration of 50 µg/mL. After 6 hours, FBS was added to the media of the cells at a final concentration of 10%. The cells were incubated for a total of 24 hours and then washed three times with PBS (5 minutes each). Slides of the live cells were prepared and imaged with a Leica TCS SP5 laser scanning confocal microscope (Leica Microsystems Inc., Benshein, Germany; WCVM, University of Saskatchewan, Saskatoon, Canada) using a 63× oil immersion objective. The sample excitation was carried out with a 476 nm argon laser source and the emission was collected from 492 to 677 nm. A total of 44 z-sections of cells were imaged, each with a step size of 0.38 µm.

V. MTT Assay

The cytotoxicity of pNDs and fNDs in serum and serum free medium was evaluated in HeLa cells by MTT assay. The stock dispersions of pNDs and fNDs at a concentration of 250 µg/mL were prepared in serum and serum-free EMEM. A two-fold serial dilution from the stock preparation of NDs was carried out to reach a concentration of 4 µg/mL. The cells were plated in 96-well cell culture plates at a density of 5,000 cells per well (100 µL volume) and allowed to adhere for 24 hours. The media of the cells was replaced with a 100 µL volume of each dilution of NDs (with serum and without serum). After 24 hours, the treatment was terminated with PBS. The cells were incubated in EMEM with serum for another 48 hours to perform the MTT assay. 10 µL of sterile MTT stock solution (5 mg/mL of MTT in PBS) diluted in 90 µL of supplemented EMEM was added to each well, and the plates were incubated at 5% $CO_2$/37° C. for 45 minutes. Thereafter, the supernatant containing excess MTT solution was removed and the plates were dried gently. The formazan crystals resulting from the reduction of MTT were extracted in DMSO by shaking the plates for 10 minutes on a plate shaker. The plates were incubated at 37° C. for 10 minutes to remove any air bubbles formed during shaking. To prevent any interference in reading absorbance that may occur due to the ND particles, the plates were centrifuged at 160 g for 10 minutes. The supernatant from the each well was transferred to the new 96-well plates and the absorbance was read at 550 nm using a microplate reader (BioTek™ Microplate Synergy HT, VT, U.S.A.). The cells grown under the same conditions without ND treatment were used as controls. The mean absorbance of the control cells was set to 100% and consequently, the cellular viability was calculated as percent viability based on the formula:

$$\% \text{ Cell viability} = \frac{Absorbance_{treated}}{Absorbance_{control}} * 100.$$

VI. Fluorescence Activated Cell Sorting (FACS)

FACS was used to evaluate the transfection ability of a fNDs-siRNA complex. HeLa/GFP cells were seeded in a 6-well plate at a density of $1 \times 10^5$ cells per well and allowed to adhere for 24 hours. The fNDs-siRNA complex was prepared at a weight ratio of 35:1 fNDs:siRNA using the method described above. Lipofectamine was used as a positive control for delivering the siRNA to the cells. Cells with no siRNA treatment were used as a control. The cells were treated with fNDs-siRNA, Lipofectamine-siRNA and naked siRNA at a final siRNA concentration of 60 nM. After 7 hours, the Lipofectamine-siRNA treatment was removed (due to the high toxicity of Lipofectamine) and fresh supplemented media was added to the wells. On the remaining wells, after 7 hours of treatment, the media was supplemented with FBS to a final concentration of 10%. After 24 hours of treatment, the media from all of the wells were aspirated and replaced with fresh supplemented media, and the plates were incubated for another 48 hours.

Thereafter, the cells were washed three times with PBS (5 minutes each), harvested using trypsin (0.25%)-EDTA, and resuspended in supplemented EMEM media (10% FBS). The cell suspension was transferred into a 5-mL flow cytometry tube and GFP knockdown was measured by a BD FACSCalibur™ (BD Biosciences, Calif., USA) flow cytometer using a 488-nm excitation laser. A total of 10,000 events were recorded per sample. The GFP fluorescence was measured using 585/42 nm (FL2) band pass filters with the detector voltage set to 392 V. The signals were amplified using logarithmic mode with an amplification gain of 1. The forward scatter (volatge-E1, mode-linear, amplitude gain-3.35) and side scatter (voltage-334, mode-linear, amplitude gain-1.00) excluded the cell debris. Data were analyzed using BD CellQuest™ Pro software (version 6.0). To quantify the GFP knockdown, the histogram (GFP intensity versus number of events) was divided into four equal quadrants, and assigned low, mild, moderate and high GFP fluorescence intensity regions. The relative percentage GFP intensity shown by the treatment groups was determined by combining the populations of moderate and high GFP intensity quadrants, and then comparing those with the untreated cells.

VII. Statistical Analyses

MTT results are expressed as the mean of $n=3\pm S.E.M$, where each n is derived from the average of 3 individual measurements. Scheffé post-hoc multiple comparison tests was used for statistical analyses when the sample variance was homogenous. In case of non-homogenous variance, Dunnett's T3 post-hoc multiple comparison test was used. The significant differences were considered at $p<0.05$ level. SPSS program version 19.0 was used.

B. Results and Discussion

I. Interaction of NDs with Human Cells

The cellular interaction of NDs was examined using the technique of backscattering mode microspectroscopic mapping and laser confocal scanning microscopy.

Backscattering Mode Mapping

Considering the high refractive index of diamonds (2.4), it could be possible to identify these particles in the cells by measuring the intensity of elastically scattered light. NDs scatter the light elastically with a higher intensity than cellular structures of the same size[63] since the refractive indices of cellular materials are almost half (~1.35 to ~1.7) that of the diamond[64]. For example, synthetic diamond nanocrystals (55 nm) have been identified in cells using differential interference contrast microscopy and have shown potential to act as a scattering labe[65].

Hence, with an aim of identifying the cellular association of detonation NDs, an area of a gold substrate with cells was scanned to measure elastically scattered light. The backscatter map of the pNDs treated cells showed a high intensity red region (surrounded by a green region) only near one end of the cells (FIG. 10B), when compared to the control cells (FIG. 12B). No red color was observed in any other region of the cells. However a clearly distinct blue colored region accompanied by an indigo-colored region can be observed near the inner cellular membrane, in contrast to the central region of cells that showed a violet color (least intensity). The backscatter map of the fND-treated cells (FIG. 11B) demonstrated clear distinct red regions near the cellular membrane and also towards the center of the cells, when compared with the control cells (FIG. 12C).

Hence, the backscattering mode mapping demonstrated the interaction of fNDs with the cells. It should be noted that no NDs were observed in the white light images of NDs treated cells. While not wishing to be limited by theory, this may be attributed either due to the smaller size of NDs that is beyond the resolution power of Raman microspectroscopy or due to the cellular internalization of NDs themselves. Although the backscattering maps provided evidence of cellular interaction of fNDs with cells, it was not clear if the NDs were present inside the cells or on the surface of cells.

Laser Confocal Scanning Microscopy

With an aim of examining the cellular internalization ability of fNDs, laser scanning confocal microscopy was carried out on HeLa cells cultured in the media containing fNDs. As the NDs used in this study did not show bright fluorescence emission at a particular wavelength, the images were collected over a wide emission range[66]. The brightfield (A), fluorescence (B) and overlay of brightfield and fluorescence (C) images of the top, middle and bottom z-positions of fND treated HeLa cell are shown (FIG. 13). The top, middle and bottom sections correspond to the $44^{th}$ $22^{nd}$ and $1^{st}$ sections, respectively. An overlay of brightfield and fluorescence image of a middle slice of an fND treated live cell revealed internalization of a few fND particles, as marked by the red circle (FIG. 13C, middle). These particles appear to be localized near the nucleus of the cell. However, the fluorescence of these particles in the middle z-section was not distinctly identified due to the interference originating from cellular autofluorescence. The overlay of fluorescence and brightfield image of four consecutive slices from the middle ($21^{st}$) towards the bottom of the cell revealed more distinct fND fluorescence emission, since the autofluorescence from the cell was less dominating towards the bottom of the cell (FIG. 14C).

It was revealed that the NDs used in this study had their own fluorescence, but the emission was not bright enough to be detected distinctly by the confocal fluorescence microscopy. It should be noted that these detonation NDs were not irradiated and annealed. While not wishing to be limited by theory, this might create the (N-V) color centers emitting bright fluorescence with high photostability[67,68]. Accordingly, it will be useful to irradiate NDs with high energy sources such as proton, electron or helium ions, followed by thermal annealing to create the bright color centers in the NDs, which could be detected by confocal microscopy.

However, from this preliminary study, there is evidence that the fNDs are able to internalize into the cells.

III. Cytotoxicity Assay

It is important to test the cytotoxicity of a delivery agent before proceeding to optimization of its transfection efficacy. Using the HeLa cell line, cytotoxic effects of seven different concentrations of NDs, ranging from 4 to 250 µg/mL incubated with cells for 24 hours, in the presence and absence of serum, were studied. In these experiments, none of the examined concentrations of pNDs showed statistically significant differences in cellular viabilities compared to control and 4 µg/mL pNDs treated cells (Scheffé post-hoc multiple comparison test, $p<0.05$), indicating biocompatibility of pNDs towards the HeLa cells (FIG. 15). In addition, the presence or absence of serum during the treatment did not contribute to any considerable changes in the cellular viabilities (FIG. 15).

The overall mean cellular viabilities after treatment with pNDs in the absence of serum ranged from 88.70 to 102.27%, while the cells incubated with pNDs in presence of serum showed a mean cellular viability of from 100.79 to 108.87%. This indicates, that although not significant, the pNDs with serum have a proliferative effect on the cells since the observed mean cellular viability was greater than 100% with all of the tested concentrations, in agreement with Schrand et al[62].

The fNDs also had negligible cytotoxic effects on HeLa cells as none of the tested concentrations showed significant differences in cell viabilities compared to control and 4 µg/mL fND treated cell population, both in presence and in absence of the serum in the cell culture medium (FIG. 16, Dunnett's T3 post-hoc multiple comparison test, $p<0.05$). The mean cellular viability ranged from 86.61 to 105.24% in fNDs treated cells with serum, which decreased slightly to 84.44 to 99.50% when the serum was excluded from the treatment medium. Overall, the percentage viability of the cells incubated with fNDs (FIG. 16) was a little lower than that observed with pNDs (FIG. 15).

This cytotoxicity assay demonstrated that the NDs do not possess inherent cellular toxicity as supported by other studies[58,28,18], when used in the concentration range from 4 to 250 µg/mL. It will be appreciated, that many other factors such as type of cell line, impurities, functionalization and/or size of nanoparticles can ultimately affect the behavior of NDs in biological systems[69]. However, the NDs used in this study were observed to exhibit high biocompatibility towards the HeLa cell line.

IV: fNDs as siRNA Delivery Agents

The siRNA is a double stranded fragment of RNA possessing 21-23 nucleotides that has recently gained interest for silencing specific gene expression[70]. After being internalized into cells, one strand of siRNA assembles into an RNA induced silencing complex (RISC) depending upon the structural features of siRNA[71]. Argonaute 2, a catalytic element of the RNA induced silencing complex, activates the RISC complex by cleaving the sense strand of siRNA[72,73], which subsequently releases its antisense strand free to degrade the complementary mRNA released from the nucleus into the cytoplasm of the cell[74]. The activated RISC continues its silencing effect until it undergoes degradation or a significant dilution below the therapeutic level[75].

RNA-interference mediated silencing induced by siRNA has found early applications in treating hepatitis B[76], cancer[77,78], ocular neovascularization[79] and acute liver failure[80]. Therefore it would be useful for silencing gene expression to deliver siRNA efficiently into the cytoplasm of a cell, making it available for cleaving the complementary post-transcriptional mRNA. However, the anionic nature of siRNA provides a barrier for its effective internalization across the negatively charged cellular surface, bringing the need for a carrier that could effectively deliver siRNA into the cytoplasm of cells.

The fNDs demonstrated the potential to act a siRNA delivery agent, therefore its efficacy to deliver anti GFP-siRNA in HeLa/GFP cells was evaluated by flow cytometry. The majority of the gated untreated HeLa/GFP cells were found in the moderate GFP (42%) followed by the high GFP (30%) intensity quadrants, while the mild and low GFP intensity regions consisted of only 17% and 11% of the gated events, respectively (FIG. 17A). Lipofectamine, a commercially available transfecting agent, when used as a siRNA delivery agent substantially shifted the HeLa/GFP cell population towards the lower GFP intensity regions, with only 2% and 22% of the gated cells remaining in the high and moderate GFP intensity quadrants, respectively (FIG. 17B).

The fNDs:siRNA (35:1,w/w/) as a transfection complex also shifted the cell population towards the lower GFP intensity, with 15% and 39% cells appearing in low and mild GFP intensity quadrants, respectively (FIG. 17C). But a similar shift was also observed in the naked siRNA treated HeLa/GFP cells, which showed 30% and 31% of cell population in the low and mild GFP intensity regions, respectively (FIG. 17D).

Overall, the Lipofectamine-siRNA (positive control) knocked the GFP intensity down by 66% (FIG. 18) relative to the untreated group. The fNDs-siRNA knocked down the GFP intensity by 36%, which was 9% less than that observed with naked siRNA treated cells (45%).

V. Summary

In this study, the high fluorescence of NDs and cells limited the use of Raman microspectroscopy in detecting the diamond signal of NDs interacting with the cells. However, the maps constructed by measuring the elastically scattered light have a higher potential for identification of the NDs in the cells. The comparison of fluorescence and backscattering maps of fND-treated and untreated cells provided clear evidence of the interaction of fNDs with cells. Laser scanning confocal microscopic measurements suggested the internalization of some particles of fNDs. The pNDs and fNDs demonstrated high biocompatibility in HeLa cells up to a 250 μg/mL concentration, with no considerable alterations in cell viability by the presence or absence of serum in the treatment media.

Example 3

Evaluation of the Feasibility of Scanning Transmission X-Ray Spectrometry to Identify Nanodiamonds in Mammalian Cells Soft X-ray spectromicroscopy of the cells incubated with fNDs was carried out using a scanning transmission X-ray spectromicroscope (STXM) at beamline 101D-1 of the Canadian Light Source (CLS, University of Saskatchewan, Saskatoon, SK, Canada). The advantages associated with STXM include high spatial resolution (less than 50 nm)[81,82], non-interference from the fluorescence of cells or NDs, and no need of staining cellular structures. A375 cells were plated on silicon nitride windows, placed in a 24-well cell culture plate, at a density of 10,000 cells per well, and allowed to adhere for 24 hours. After treating with NDs for 2 hours, the samples were sent to CLS for the soft X-Ray microscopic measurements.

To fulfill the requirements for identification inside the cells, the NDs should possess a unique identifiable STXM spectrum. Spectra from the four different regions of NDs (FIG. 19A) at the C 1s edge were recorded to examine the possibility of identifying these nanoparticles in cells. All of the spectra were similar, with the same absorption peaks at the C 1s edge (FIG. 19B), supporting the use of STXM in detecting NDs in cells.

Measurements at the C 1s edge from six different regions of a single cell treated with NDs (FIG. 20A) revealed three different spectral patterns (FIGS. 20B and 20C). In stack 1 (FIG. 20B), the green and blue colored spectra were identical; while pink spectra showed absorption peaks at somewhat different energy range. The blue and green colored spectral pattern were assigned to proteins, while the pink colored pattern arose due to the lipids present in the cells, as discussed in other studies[81,83,84]. The spectra shown in stack 2 (FIG. 20C) were identical to the spectra obtained from NDs alone (FIG. 19B). Therefore, these spectra indeed can be assigned to the NDs. Subsequently by fitting these spectra, the presence of NDs (FIG. 21A), proteins (FIG. 21B) and lipids (FIG. 21C) was revealed, indicated by the brighter regions in the respective figures. The constructed color image of the scanned cellular region clearly revealed the cellular composition and association of NDs (FIG. 22); where blue colored region corresponds to the lipids of the cell, green indicates the cellular proteins and red demonstrates NDs. The magenta color observed in the cells is due to the overlap of the red and blue colors, indicating the association of lipids with NDs.

Therefore, STXM is useful to identify NDs and can be used to reveal the origin of ND signals.

Example 4

Functionalization of Nanodiamonds with Lysine and Histidine

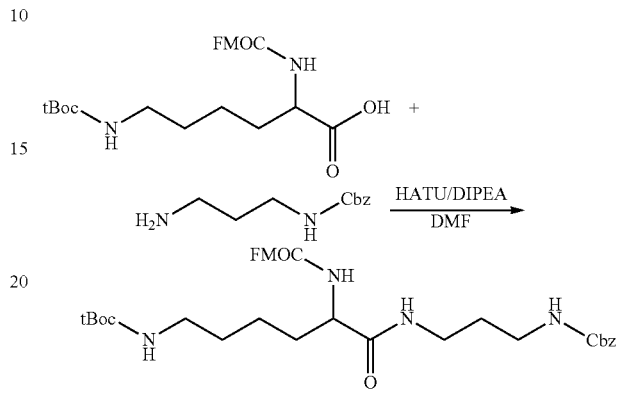

(a) Synthesis of N'—(N$^\alpha$-Fmoc-N$^\epsilon$-Boc-Lysyl)-N"-Cbz-diaminopropane N$^\alpha$-Fmoc-N$^\epsilon$-Boc-Lysyl (8.661 mmoles) was dissolved in 15 mL of dry DMF, followed by the addition of O-(7-azabenzotriazol-1-yl)-N,N,N',N'-tetramethyluronium hexafluorophosphate (HATU) (10.82 mmoles) and diisopropylethylamine (DIPEA) (17.97 mmoles) and maintained under a nitrogen atmosphere in a Schlenk flask. The reaction mixture was stirred for 15 minutes at room temperature.

Cbz-diaminopropane (9.925 mmoles) was dissolved in 10 mL of dry DMF and DIPEA (10.92 mmoles) was added into it. The solution of Cbz-diaminopropane was added in the reaction mixture. The reaction was kept at room temperature under nitrogen atmosphere and constant stirring overnight. After completion of the reaction, DMF was removed under vacuum and the solid white compound was dissolved in 100 mL of DCM. Vortexing was done to ensure complete dissolution. The compound was extracted using saturated solution of sodium bicarbonate (3×100 mL), dried with sodium sulphate and filtered. The obtained purified organic phase was subjected to solvent evaporation under vacuum. The solid compound was redissolved in minimum amount of DCM and washed with excess ether. The precipitates obtained as a result of ether washing was filtered and dried under vacuum to produce desired compound which appeared as white powder.

The percentage yield of N'—(N$^\alpha$-Fmoc-N$^\epsilon$-Boc-Lysyl)-N"-Cbz-diaminopropane was 71.06%

(b) Fmoc deprotection from N'—(N$^\alpha$-Fmoc-N$^\epsilon$-Boc-Lysyl)-N"-Cbz-diaminopropane

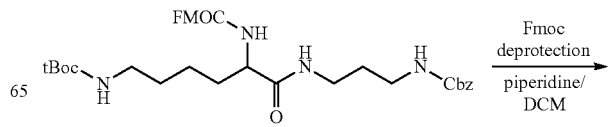

-continued

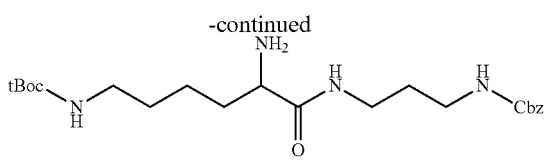

N'—(Nα-Fmoc-Nε-Boc-Lysyl)-N'''-Cbz-diaminopropane (6.1173 mmoles) was dissolved in 50% dry dichloromethane (DCM) (10 mL) and 50% piperidine (10 mL) under nitrogen atmosphere in a Schlenk flask. The reaction was monitored for completion by TLC. The reaction was completed in two hours. After completion, excess acetone was added in the reaction mixture. Upon standing, white crystalline precipitate of piperidine bi-product was formed in the mixture which was filtered under vacuum. Solvent evaporation was performed to obtain dry compound. The compound was redissolved in minimum amount of DCM and washed with excess hexanes. The hexane insoluble portion was separated and subjected to solvent evaporation producing a yellowish oil as the desired compound.

The percentage yield of Fmoc deprotected N'—(N$^\alpha$—N$^\epsilon$-Boc-Lysyl)-N'''-Cbz-diaminopropane was 77.73%

(c) Attachment of N$^\alpha$-Nim-Bis-Boc histidine to Fmoc deprotected N'—(N$^\alpha$—N$^\epsilon$-Boc-Lysyl)-N'''-Cbz-diaminopropane

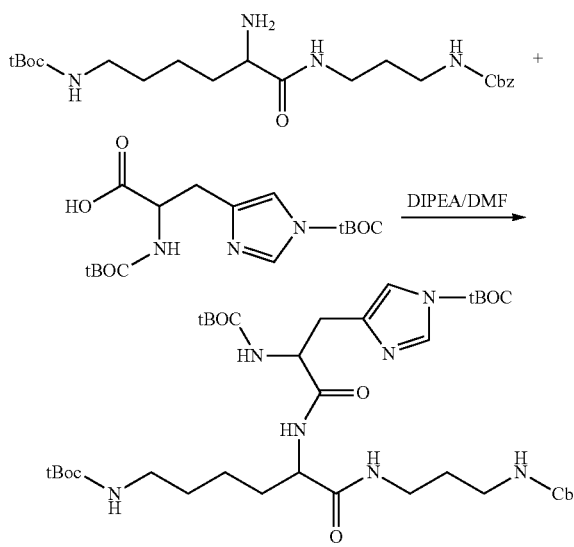

N$^\alpha$-Nim-Bis-Boc histidine (2.35 mmoles) was dissolved in 15 mL of dry dimethylformamide (DMF), followed by addition of DIPEA (4.86 mmoles) under nitrogen atmosphere maintained in the Schlenk flask. HATU was not added since histidine was already in the form of activated ester.

Fmoc deprotected N'—(N$^\alpha$—N$^\epsilon$-Boc-Lysyl)-N'''-Cbz-diaminopropane (2.35 mmoles) was dissolved in 10 mL of dry DMF and the solution was added to the reaction mixture. The reaction was kept at room temperature under nitrogen atmosphere and constant stirring overnight. After completion, DMF was removed under vacuum and the compound was dissolved in 100 mL of DCM followed by extraction using saturated sodium bicarbonate (3×100 mL) and 10% sodium chloride (1×100 mL). The organic phase was dried using sodium sulphate and filtered. Purified organic phase was subjected to solvent evaporation to obtain dark yellow oil as the desired compound.

The percentage yield of N'—(N$^\alpha$—(N$^\alpha$-Nim-Bis-Boc histidine) N$^\epsilon$-Boc-Lysyl)-N'''-Cbz-diaminopropane was 73.85%

(d) Cbz deprotection from N'—(N$^\alpha$—(N$^\alpha$-Nim-Bis-Boc histidine) N$^\epsilon$-Boc-Lysyl)-N'''-Cbz-diaminopropane

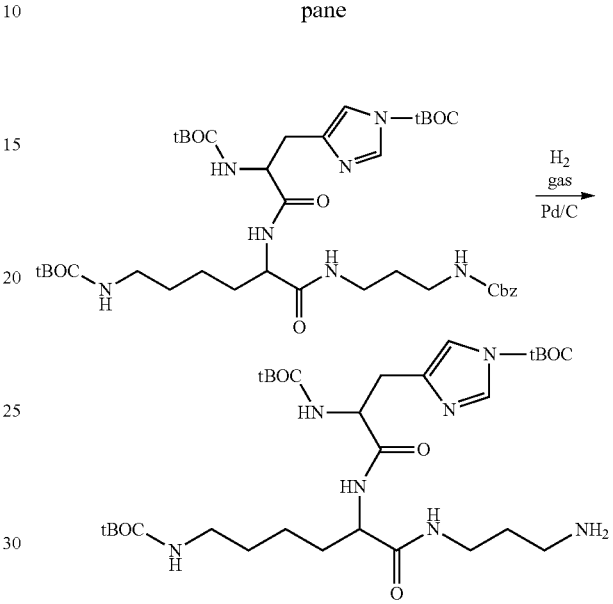

Catalytic amount of palladium on carbon (Pd/C) was suspended in 10 mL of methanol under a hydrogen atmosphere in the Schlenk flask.

N'—(N$^\alpha$—(N$^\alpha$-Nim-Bis-Boc histidine) N$^\epsilon$-Boc-Lysyl)-N'''-Cbz-diaminopropane (1.7443 mmoles) was dissolved in 10 mL of methanol and the solution was added to the reaction mixture. The balloon filled with hydrogen gas was attached to the reaction flask using syringe method. Nitrogen supply was stopped to allow hydrogen to flow through the reaction mixture. The reaction was kept under constant stirring overnight. After completion, filtration was performed to remove palladium. A minute quantity of palladium left in the filtrate was removed by refiltation using celite. The clean filtrate was then subjected to solvent evaporation to remove methanol under vacuum and white crystalline powder of the desired compound was obtained.

The percentage yield of Cbz deprotected N'—(N$^\alpha$—(N$^\alpha$-Nim-Bis-Boc histidine) N$^\epsilon$-Boc-Lysyl)-N'''-diaminopropane was 99%

(e) Formation of Acid Chloride Functionalized Nanodiamonds

Reoxidized nanodiamonds (153 mg) were suspensed in 20 mL of thionyl chloride in the presence of YTZ grinding media under nitrogen atmosphere maintained in a Schlenk flask. The mixture was sonicated at 25 kHz without heating for four hours followed by reflux for 20 hours at 100° C. using oil bath. The reaction mixture was again sonicated under the same conditions for 2 hours followed by reflux for 3 hours. The thionyl chloride was removed by vacuum in the Schlenk line.

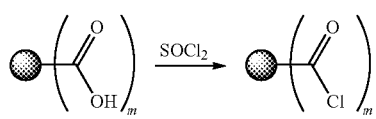

(f) Attachment of Cbz Deprotected N'—(N$^\alpha$—(N$^\alpha$-Nim-Bis-Boc Histidine) N$^\epsilon$-Boc-Lysyl)-N''-Diaminopropane to Acid Chloride Nanodiamonds and tBOC Deprotection

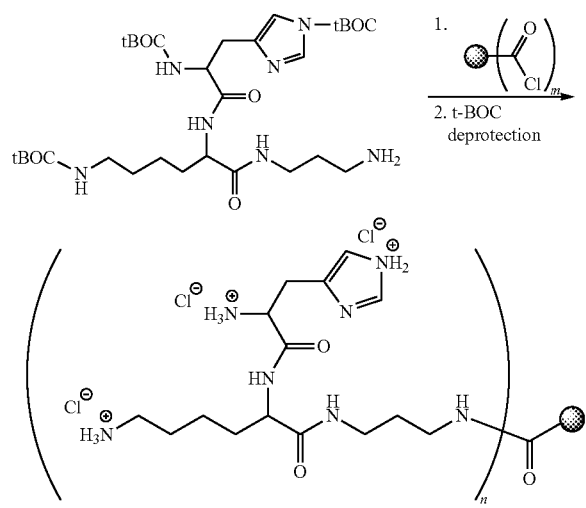

Acid chloride nanodiamonds (153 mg) were suspended in dry DMF (10 mL) under a nitrogen atmosphere maintained in the schlenk flask.

Cbz deprotected N'—(N$^\alpha$—(N$^\alpha$-Nim-Bis-Boc histidine) N$^\epsilon$-Boc-Lysyl)-N''-diaminopropane (0.468 mmoles) was dissolved in dry DMF and air was purged from of the solution by using nitrogen gas. The solution was added to the reaction mixture under nitrogen. The reaction mixture was sonicated at 25 kHz for 4 hours and refluxed at 100° C. using oil bath for 20 hours. After completion, the mixture was again sonicated under the same conditions for 2 hours followed by reflux for 3 hours. DMF was removed under vacuum and the functionalized nanodiamonds were suspended in methanol for dialysis to remove unattached starting material using cellulose membrane and 90% ethanol as the bath. The ethanol bath was changed at regular intervals.

N'—(N$^\alpha$—(N$^\alpha$-Nim-Bis-Boc histidine) N$^\epsilon$-Boc-Lysyl)-N''-diaminopropane functionalized nanodiamonds were subjected to solvent evaporation to remove methanol. The dry functionalized nanodiamonds were suspended in 10 mL of DCM in a Schlenk flask maintained under a nitrogen atmosphere and 10 eq. of 4M HCl (in dioxane) was added. The reaction mixture was stirred for 90 minutes at room temperature, the solvent was pumped off and subjected to freeze drying for 3 days to obtain Boc deprotected histidine-lysine functionalized nanodiamonds.

Example 5

Flow Cytometry for Evaluating Cellular Uptake of Lysine-NDs: Preparation of ND Dispersion Primary dispersion of lysine-NDs was prepared in aqueous media at final concentration of 2 mg/mL. Zirconia (YTZ) grinding media was added and the dispersion was subjected to untrasonication for 4 hours at 25 kHz without heating. The dispersion was then centrifuged at 5200 g for 3 minutes to sediment the YTZ grinding media and aggregated ND particulates. The resulting dispersion was used in the subsequent cellular experiments.

A. Method:

Flow cytometry was used to evaluate the cellular internalization of lysine-NDs which were complexed with FITC conjugated control SiRNA. HeLa cells were seeded in 6 well plates at a density of 2×10$^5$ cells/well. The cells were incubated at 37° C. and 5% CO$_2$ to allow attachment. FITC conjugated control SiRNA was complexed with lysine-NDs dispersed in aqueous medium at a specific weight ratio of 1:40 by incubating the dispersion for 30 minutes at room temperature. The final concentration of SiRNA in each well was 75 pmoles. The attached cells were then treated with lysine ND-SiRNA complexes. Untreated and uncomplexed lysine-NDs treated cells were used as negative and positive control respectively. After treatment induction, the cells were incubated at 37° C. and 5% CO$_2$. The treatments were terminated after 20 hours and cells were washed with 1×PBS three times for 5 minutes each. The cells were harvested using trypsin and 0.25% EDTA, centrifuged at 95 g and 4° C. for 5 minutes to obtain cell pellets. The individual cell pellets were re-suspended in 500 µL of 1×PBS, transferred into 5 mL flow cytometer tubes and the fluorescence was measured using BD FACS Calibur™ (BD Biosciences, CA, USA). Fluorescence from FITC SiRNA complexed with lysine-NDs was analysed using FITC (FL1-H) channel by plotting log of fluorescence intensity versus number of events. A total of 10,000 events were recorded in the gated region per sample. The data was obtained and evaluated using BD CellQuest™ Pro software (version 6.0). The results were analysed by comparing the relative fluorescence shift from negative to positive for treated cells to the auto fluorescence of untreated cells.

B. Statistical Analysis:

Flow cytometry results for cellular internalization of lysine-NDs in aqueous medium were expressed as the mean of n=3±S.D. One way ANOVA and Tukey's post hoc multiple comparisons were used for analysis since samples were normally distributed and had homogenous variance.

C. Result:

Flow cytometry results indicate a statistically significant positive fluorescence shift of 19.6±2.3% for cells treated with lysine NDs-FITC SiRNA complex as compared to untreated cells (4.6±0.42%). It should also be noted that there was a significant difference in the fluorescence shift for lysine NDs treated cells (8.27±1.2%) and lysine NDs-FITC SiRNA complex treated cells (19.6±2.3%) (FIG. 23, ANOVA, Tukey's post hoc multiple comparison, p-value<0.05). The findings illustrate cellular association of lysine-NDs and also indicate intracellular delivery of FITC conjugated SiRNA.

While the present application has been described with reference to what are presently considered to be the preferred examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE SPECIFICATION

1. Schrand A, Hens S A C, Shenderova O. Nanodiamond particles: properties and perspectives for bioapplications. *Crit. Rev Solid State Mater Sci.* 2009; 34(1-2):18-74.
2. Danilenko V V. On the history of the discovery of nanodiamond synthesis. *Phys Solid State.* 2004; 46(4):595-599.
3. Dolmatov V Y. Application of detonation nanodiamond. In: Shenderova O A, Gruen D M, editors. *Ultrananocrystalline Diamond: Synthesis, Properties, and Applications.* New York: William Andrew Publishing; 2006:477-528.
4. Bondar' V S, Pozdnyakova I O, Puzyr' A P. Applications of nanodiamonds for separation and purification of proteins. *Phys Solid State.* 2004; 46(4):758-760.
5. Chow E K, Zhang X Q, Chen M, et al. Nanodiamond therapeutic delivery agents mediate enhanced chemoresistant tumor treatment. *Sci Transl Med.* 2011; 3(73):73ra21.
6. Li J, Zhu Y, Li W, Zhang X, Peng Y, Huang Q. Nanodiamonds as intracellular transporters of chemotherapeutic drug. *Biomaterials.* 2010; 31(32):8410-8418.
7. Dolmatov V Y. Detonation synthesis ultradispersed diamonds: properties and applications. *Russ Chem. Rev.* 2001; 70(7):607-626.
8. Shenderova O A, Hens S A C. Detonation nanodiamond particles processing, modification and bioapplications. In: Ho D, editor. *Nanodiamonds: Applications in Biology and Nanoscale Medicine*. New York: Springer; 2010:79-116.
9. Aleksenskiĭ A E, Baĭdakova M V, Vul' A Y, Siklitskiĭ V I. The structure of diamond nanoclusters. *Phys Solid State.* 1999; 41(4):668-671.
10. Jiang T, Xu K. FTIR study of ultradispersed diamond powder synthesized by explosive detonation. *Carbon.* 1995; 33(12):1663-1671.
11. Krueger A. New carbon materials: biological applications of functionalized nanodiamond materials. *Chemistry.* 2008; 14(5):1382-1390.
12. Kaur R, Badea I. Nanodiamonds as novel nanomaterials for biomedical applications: drug delivery and imaging systems. *International Journal of Nanomedicine.* 2013; 8:203-220.
13. Schrand, A. M., S. A. C. Hens, and O. A. Shenderova, *Nanodiamond particles: Properties and perspectives for bioapplications*. Critical Reviews in Solid State and Materials Sciences, 2009. 34(1-2): p. 18-74.
14. Mochalin, V. N., et al., *The properties and applications of nanodiamonds*. Nature Nanotechnology, 2012. 7(1): p. 11-23.
15. Puzyr A P, Purtov K V, Shenderova O A, Luo M, Brenner D W, Bondar V S. The adsorption of aflatoxin B1 by detonation-synthesis nanodiamonds. *Dokl Biochem Biophys.* 2007; 417(1):299-301.
16. Shimkunas R A, Robinson E, Lam R, et al. Nanodiamond-insulin complexes as pH-dependent protein delivery vehicles. *Biomaterials.* 2009; 30(29):5720-5728.
17. Wang H D, Niu C H, Yang Q, Badea I. Study on protein conformation and adsorption behaviors in nanodiamond particle-protein complexes. *Nanotechnology.* 2011; 22(14):145703.
18. Huang H, Pierstorff E, Osawa E, Ho D. Active nanodiamond hydrogels for chemotherapeutic delivery. *Nano Lett.* 2007; 7(11):3305-3314.
19. Zhang X Q, Chen M, Lam R, Xu X, Osawa E, Ho D. Polymer-functionalized nanodiamond platforms as vehicles for gene delivery. *ACS Nano.* 2009; 3(9):2609-2616.
20. Chen M, Zhang X Q, Man H B, Lam R, Chow E K, Ho D. Nanodiamond vectors functionalized with polyethylenimine for siRNA delivery. *J Phys Chem. Lett.* 2010; 1(21):3167-3171.
21. Ida S, Tsubota T, Tanii S, Nagata M, Matsumoto Y. Chemical modification of the diamond surface using benzoyl peroxide and dicarboxylic acids. *Langmuir.* 2003; 19(23):9693-9698.
22. Tsubota T, Tanii S, Ida S, Nagata M, Matsumoto Y. Chemical modification of diamond surface with various carboxylic acids by radical reaction in liquid phase. *Diam Relat Mater.* 2004; 13(4-8):1093-1097.
23. Tsubota T, Ohno T, Yoshida H, Kusakabe K. Introduction of molecules containing a $NO_2$ group on diamond surface by using radical reaction in liquid phase. *Diam Relat Mater.* 2006; 15(4-8):668-672.
24. Liu Y, Gu Z, Margrave J L, Khabashesku V N. Functionalization of nanoscale diamond powder: fluoro-, alkyl-, amino-, and amino acid-nanodiamond derivatives. *Chem. Mater.* 2004; 16(20):3924-3930.
25. Krüger A, Liang Y, Jarre G, Stegk J. Surface functionalisation of detonation diamond suitable for biological applications. *J Mater Chem.* 2006; 16(24):2322-2328.
26. Krueger A, Boedeker T. Deagglomeration and functionalisation of detonation nanodiamond with long alkyl chains. *Diam Relat Mater.* 2008; 17(7-10):1367-1370.
27. Schrand A M, Huang H, Carlson C, et al. Are diamond nanoparticles cytotoxic? *J Phys Chem B.* 2007; 111(1):2-7.
28. Schrand A M, Dai L, Schlager J J, Hussain S M, Osawa E. Differential biocompatibility of carbon nanotubes and nanodiamonds. *Diam Relat Mater.* 2007; 16(12):2118-2123.
29. Chen M, Pierstorff E D, Lam R, et al. Nanodiamond-mediated delivery of water-insoluble therapeutics. *ACS Nano.* 2009; 3(7):2016-2022.
30. Faraji A H, Wipf P. Nanoparticles in cellular drug delivery. *Bioorg Med. Chem.* 2009; 17(8):2950-2962.
31. Krueger A, Stegk J, Liang Y, Lu L, Jarre G. Biotinylated nanodiamond: simple and efficient functionalization of detonation diamond. *Langmuir.* 2008; 24(8):4200-4204.
32. Ozawa M, Inaguma M, Takahashi M, Kataoka F, Krüger A, Osawa E. Preparation and behavior of brownish, clear nanodiamond colloids. *Adv Mater.* 2007; 19(9):1201-1206.
33. Wagner, Ingrid; Musso, Hans (November 1983). "New Naturally Occurring Amino Acids". *Angew. Chem. Int. Ed. Engl.* 22 (22): 816-828.
34. Singh J, Yang P, Michel D, Verrall R E, Foldvari M, Badea I. Amino acid-substituted gemini surfactant-based nanoparticles as safe and versatile gene delivery agents. *Curr Drug Deliv.* 2011; 8(3):299-306.
35. Kim B, Sigmund W M. Functionalized multiwall carbon nanotube/gold nanoparticle composites. *Langmuir.* 2004; 20(19):8239-8242.
36. Pham T A, Son S M, Jeong Y T. Water-dispersible multi-walled carbon nanotubes and novel hybrid nanostructures. *Synth React Inorg Met-Org Nano-Metal Chem.* 2010; 40(4):216-224.
37. Liu J, Rinzler A G, Dai H, et al. Fullerene pipes. *Science.* 1998; 280(5367):1253-1256.
38. Kong H, Gao C, Yan D. Functionalization of multiwalled carbon nanotubes by atom transfer radical polymerization and defunctionalization of the products. *Macromolecules.* 2004; 37(11):4022-4030.

[39] Philip B, Xie J, Abraham J K, Varadan V K. Polyaniline/carbon nanotube composites: starting with phenylamino functionalized carbon nanotubes. *Polym Bull.* 2005; 53(2): 127-138.

[49] Sainsbury T, Erickson K, Okawa D, Zonte C S, Fréchet J M J, Zettl A. Kevlar functionalized carbon nanotubes for next-generation composites. *Chem. Mater.* 2010; 22(6): 2164-2171.

[41] Han G, Tamaki M, Hruby V J. Fast, efficient and selective deprotection of the tert-butoxycarbonyl (Boc) group using HCl/dioxane (4 M). *J Pept Res.* 2001; 58(4):338-341.

[42] Solin S A, Ramdas A K. Raman spectrum of diamond. *Phys Rev B.* 1970; 1(4):1687-1698.

[43] Ager J W 3rd, Veirs D K, Rosenblatt G M. Spatially resolved Raman studies of diamond films grown by chemical vapor deposition. *Phys Rev B Condens Matter.* 1991; 43(8):6491-6499.

[44] Ganesan S, Maradudin A A, Oitmaa J. A lattice theory of morphic effects in crystals of the diamond structure. *Ann Phys.* 1970; 56(2):556-594.

[45] Mochalin V, Osswald S, Gogotsi Y. Contribution of functional groups to the Raman spectrum of nanodiamond powders. *Chem. Mater.* 2009; 21(2):273-279.

[46] Mochalin V N, Shenderova O, Ho D, Gogotsi Y. The properties and applications of nanodiamonds. *Nat. Nanotechnol.* 2012; 7(1):11-23.

[47] Osipov V Y, Aleksenskiy A E, Shames A I, Panich A M, Shestakov M S, Vul A Y. Infrared absorption study of surface functional groups providing chemical modification of nanodiamonds by divalent copper ion complexes. *Diam Relat Mater.* 2011; 20(8):1234-1238.

[48] Bellamy L J. Alkanes. In: Bellamy L J. *Advances in Infrared Group Frequencies.* 1st ed. London: Methuen; 1968:1-20.

[49] Kim T, Lee K, Gong M S, Joo S W. Control of gold nanoparticle aggregates by manipulation of interparticle interaction. *Langmuir.* 2005; 21(21):9524-9528.

[50] Zhao D, Li Q, Duan E, Li H, Shen X. Solubility of L-lysine hydrochloride in dimethyl sulfoxide, methanol, ethanol, water, and glycol between (283 and 323) K. *J Chem Eng Data.* 2009; 54(7):2126-2127.

[51] Zanetti-Ramos B G, Fritzen-Garcia M B, Creczynski-Pasa T B, et al. Characterization of polymeric particles with electron microscopy, dynamic light scattering, and atomic force microscopy. *Particul Sci Technol.* 2010; 28(5):472-484.

[52] Singh J, Michel D, Chitanda J M, Verrall R E, Badea I. Evaluation of cellular uptake and intracellular trafficking as determining factors of gene expression for amino acid-substituted gemini surfactant-based DNA nanoparticles. *J Nanobiotechnology.* 2012; 10:7.

[53] Donkuru M, Badea I, Wettig S, Verrall R, Elsabahy M, Foldvari M. Advancing nonviral gene delivery: lipid- and surfactant-based nanoparticle design strategies. *Nanomedicine (Lond).* 2010; 5(7):1103-1127.

[54] Akinc A, Lynn D M, Anderson D G, Langer R. Parallel synthesis and biophysical characterization of a degradable polymer library for gene delivery. *J Am Chem Soc.* 2003; 125(18):5316-5323.

Katas H, Alpar H O. Development and characterisation of chitosan nanoparticles for siRNA delivery. *J Control Release.* 2006; 115(2): 216-225.

[56] Lee D W, Yun K S, Ban H S, Choe W, Lee S K, Lee K Y. Preparation and characterization of chitosan/polygulur-onate nanoparticles for siRNA delivery. *J Control Release.* 2009; 139(2):146-152.

[57] Faklaris O, Joshi V, Irinopoulou T, Tauc P, Sennour M, Girard H, Gesset C I, Arnault J-C, Thorel A, Boudou J-P, et al.: Photoluminescent Diamond Nanoparticles for Cell Labeling: Study of the Uptake Mechanism in Mammalian Cells. *ACS Nano* 2009, 3:3955-3962.

[58] Liu K K, Wang C C, Cheng C L, Chao J I: Endocytic carboxylated nanodiamond for the labeling and tracking of cell division and differentiation in cancer and stem cells. *Biomaterials* 2009, 30:4249-4259.

[59] Yu S J, Kang M W, Chang H C, Chen K M, Yu Y C: Bright fluorescent nanodiamonds: No photobleaching and low cytotoxicity. *Journal of the American Chemical Society* 2005, 127:17604-17605.

[60] Liu K K, Cheng C L, Chang C C, Chao J I: Biocompatible and detectable carboxylated nanodiamond on human cell. *Nanotechnology* 2007, 18:325102.

[61] Chao J I, Perevedentseva E, Chung P H, Liu K K, Cheng C Y, Chang C C, Cheng C L: Nanometer-sized diamond particle as a probe for biolabeling. *Biophysical Journal* 2007, 93:2199-2208.

[62] Schrand A M, Johnson J, Dai L, Hussain S M, Schlager J J, Zhu L, Hong Y, Osawa E: Cytotoxicity and Genotoxicity of Carbon Nanomaterials. *Safety of Nanoparticles: From Manufacturing to Medical Applications* 2009:159-187.

[63] Colpin Y, Swan A, Zvyagin A V, Plakhotnik T: Imaging and sizing of diamond nanoparticles. *Optics Letters* 2006, 31:625-627.

[64] Tuchin V V: Methods and algorithms for the measurement of the optical parameters of tissues. In *Tissue Optics: Light Scattering Methods and Instruments for Medical Diagnosis*, edn 2. SPIE; 2007:143-256.

[65] Smith B R, Niebert M, Plakhotnik T, Zvyagin A V: Transfection and imaging of diamond nanocrystals as scattering optical labels. *Journal of Luminescence* 2007, 127:260-263.

[66] Kompan M E, Terukov E I, Gordeev S K, Zhukov S G, Nikolaev Y A: Photoluminescence spectra of ultradisperse diamond. *Physics of the Solid State* 1997, 39:1928-1929.

[67] Fu C C, Lee H Y, Chen K, Lim T S, Wu H Y, Lin P K, Wei P K, Tsao P H, Chang H C, Fann W: Characterization and application of single fluorescent nanodiamonds as cellular biomarkers. *Proceedings of the National Academy of Sciences of the United States of America* 2007, 104:727-732.

[68] Weng M F, Chiang S Y, Wang N S, Niu H: Fluorescent nanodiamonds for specifically targeted bioimaging: Application to the interaction of transferrin with transferrin receptor. *Diamond and Related Materials* 2009, 18:587-591.

[69] Lewinski N, Colvin V, Drezek R: Cytotoxicity of nanoparticles. *Small* 2008, 4:26-49.

[70] Dykxhoorn D M, Novina C D, Sharp P A: Killing the messenger: Short RNAs that silence gene expression. *Nature Reviews Molecular Cell Biology* 2003, 4:457-467.

[71] Schwarz D S, Hutvágner G, Du T, Xu Z, Aronin N, Zamore P D: Asymmetry in the assembly of the RNAi enzyme complex. *Cell* 2003, 115:199-208.

[72] Matranga C, Tomari Y, Shin C, Bartel D P, Zamore P D: Passenger-Strand Cleavage Facilitates Assembly of siRNA into Ago2-Containing RNAi Enzyme Complexes. *Cell* 2005, 123:607-620.

[73] Rand T A, Ginalski K, Grishin N V, Wang X: Biochemical identification of Argonaute 2 as the protein required for RNA-induced silencing complex activity. *Proceedings of the National Academy of Sciences of the United States of America* 2004, 101:14385-14389.

[74] Ameres S L, Martinez J, Schroeder R: Molecular Basis for Target RNA Recognition and Cleavage by Human RISC. *Cell* 2007, 130:101-112.

[75] Bartlett D W, Davis M E: Insights into the kinetics of siRNA-mediated gene silencing from live-cell and live-animal bioluminescent imaging. *Nucleic Acids Research* 2006, 34:322-333.

[76] McCaffrey A P, Nakai H, Pandey K, Huang Z, Salazar F H, Xu H, Wieland S F, Marion P L, Kay M A: Inhibition of hepatitis B virus in mice by RNA interference. *Nature Biotechnology* 2003, 21:639-644.

[77] Filleur S, Courtin A, Ait-Si-Ali S, Guglielmi J, Merle C, Harel-Bellan A, Clezardin P, Gabon F: SiRNA-mediated inhibition of vascular endothelial growth factor severely limits tumor resistance to Antiangiogenic thrombospondin-1 and slows tumor vascularization and growth. *Cancer Research* 2003, 63:3919-3922.

[78] Yang G, Thompson J A, Fang B L, Liu J S: Silencing of H-ras gene expression by retrovirus-mediated siRNA decreases transformation efficiency and tumor growth in a model of human ovarian cancer. *Oncogene* 2003, 22:5694-5701.

[79] Reich S, Fosnot J, Kuroki A, Tang W X, Yang X Y, Maguire A, Bennett J, Tolentino M: Small interfering RNA (siRNA) targeting VEGF effectively inhibits ocular neovascularization in a mouse model. *Molecular Vision* 2003, 9:210-216.

[80] Zender L, Hütker S, Liedtke C, Tillmann H L, Zender S, Mundt B, Walternathe M, Gösling T, Flemming P, Malek N P, et al.: Caspase 8 small interfering RNA prevents acute liver failure in mice. *Proceedings of the National Academy of Sciences of the United States of America* 2003, 100: 7797-7802.

[81] Lawrence J R, Swerhone G D W, Leppard G G, Araki T, Zhang X, West M M, Hitchcock A P: Scanning transmission X-ray, laser scanning, and transmission electron microscopy mapping of the exopolymeric matrix of microbial biofilms. *Applied and Environmental Microbiology* 2003, 69:5543-5554.

[82] Hitchcock A P, Dynes J J, Johansson G, Wang J, Botton G: Comparison of NEXAFS microscopy and TEM-EELS for studies of soft matter. *Micron* 2008, 39:311-319.

[83] Dynes J J, Lawrence J R, Korber D R, Swerhone G D W, Leppard G G, Hitchcock A P: Quantitative mapping of chlorhexidine in natural river biofilms. *Science of the Total Environment* 2006, 369:369-383.

[84] Lawrence J R, Dynes J J, Korber D R, Swerhone G D W, Leppard G G, Hitchcock A P: Monitoring the fate of copper nanoparticles in river biofilms using scanning transmission X-ray microscopy (STXM). *Chemical Geology* 2012, 329: 18-25.

TABLE 1

Zeta potential measurements of nanodiamonds (NDs)

| Sample[1] | Zeta Potential (mV) in reverse osmosis-purified water[2] |
|---|---|
| pNDs | −21.1 ± 0.2 |
| rNDs | −23.7 ± 0.5 |
| fNDs | 48.9 ± 0.1 |

[1]Abbreviations: pNDs, pristine carboxylated nanodiamonds; rNDs, re-oxidized nanodiamonds; fNDs, lysine functionalized nanodiamonds.
[2]Each value represents the mean plus or minus standard deviation of three measurements (n ≥ 10).

TABLE 2

Surface loading of nanodiamonds (NDs), as calculated from their respective thermograms.[1]

| Sample[2] | Surface loading (mmol/g) |
|---|---|
| pNDs | 0.35 |
| rNDs | 1.00 |
| fNDs | 1.70 |

[1]Weight loss below 115° C. is excluded.
[2]Abbreviations: pNDs, pristine carboxylated nanodiamonds; rNDs, re-oxidized nanodiamonds; fNDs, lysine functionalized nanodiamonds.

TABLE 3

Ratios of lysine functionality residues on the nanodiamonds (NDs) per base pair of genetic material, as calculated from surface loading measurements[1]

| Weight ratio of fNDs:genetic material | Calculated lysine functionality per pDNA base pair ratio | Calculated lysine functionality per siRNA base pair ratio |
|---|---|---|
| 1:1 | 1.1 | 1.1 |
| 5:1 | NR | 5.4 |
| 6:1 | 6.6 | NR |
| 10:1 | 11 | 11 |
| 20:1 | 22 | 22 |
| 30:1 | 33 | 32 |
| 40:1 | 44 | 43 |
| 50:1 | 55 | 54 |

[1]Abbreviations: fNDs, lysine-functionalized nanodiamonds; pDNA, plasmid DNA; siRNA, small interfering RNA; NR, not reported.

The invention claimed is:

1. A functionalized nanodiamond comprising at least one naturally occurring basic amino acid, or an analog or derivative of a naturally occurring basic amino acid, or an acid addition salt thereof, covalently linked to a nanodiamond, wherein the at least one naturally occurring basic amino acid, or an analog or derivative of a naturally occurring basic amino acid, or an acid addition salt thereof, is covalently linked to the nanodiamond via an amide linkage, and/or wherein the at least one naturally occurring basic amino acid, or an analog or derivative of a naturally occurring basic amino acid, or an acid addition salt thereof, is covalently linked to the nanodiamond via a linker group comprising a $C_{1-6}$ alkylene group.

2. The functionalized nanodiamond of claim 1, wherein the at least one naturally occurring basic amino acid is selected from one or more of lysine, arginine and histidine, and an analog or derivative thereof.

3. The functionalized nanodiamond of claim 1, wherein the at least one naturally occurring basic amino acid and the linker group together form the structure:

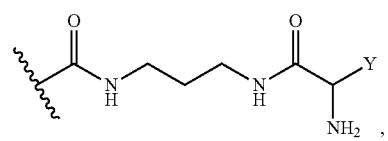

Wherein Y is selected from —(CH$_2$)$_4$NH$_2$,

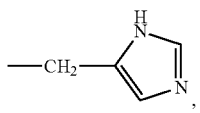

and —(CH$_2$)$_3$NHC(NH)NH$_2$.

4. The functionalized nanodiamond of claim 1, wherein the at least one naturally occurring basic amino acid and the linker group together form the structure:

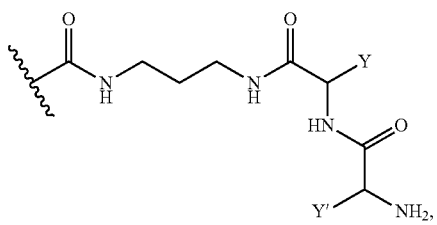

wherein Y and Y' are, independently, selected from —(CH$_2$)$_4$NH$_2$,

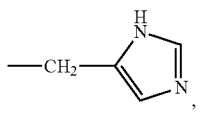

and —(CH$_2$)$_3$NHC(NH)NH$_2$.

5. The functionalized nanodiamond of claim 1, wherein the nanodiamond is prepared from a detonation nanodiamond.

6. The functionalized nanodiamond of claim 1, wherein the nanodiamond has a diameter of about 1 nm to about 10 nm, about 3 nm to about 6 nm or about 4 nm to about 5 nm.

7. The functionalized nanodiamond of claim 1, wherein the functionalized nanodiamond has a surface loading of about 0.1 mmol/g nanodiamond to about 10 mmol/g nanodiamond or about 1.7 mmol/g nanodiamond.

8. The functionalized nanodiamond of claim 1, wherein the nanodiamond further comprises one or more additional amino acids covalently linked thereto, wherein the additional amino acids are selected from naturally occurring acidic amino acids and naturally occurring neutral amino acids, and analogs and derivatives thereof.

9. The functionalized nanodiamond of claim 8, wherein the additional amino acids are selected from aspartic acid, glutamatic acid, lysyl methyl ester and histidyl methyl ester, and analogs and derivatives thereof.

10. The functionalized nanodiamond of claim 1, wherein the nanodiamond further comprises one or more targeting moieties covalently linked thereto.

11. A composition comprising a functionalized nanodiamond of claim 1 and a carrier.

12. The composition of claim 11, wherein the composition has a zeta potential of greater than about +30 mV.

13. The composition of claim 11, wherein the composition has an average particle size of about 5 nm to about 50 nm or about 21 nm.

14. A complex comprising a functionalized nanodiamond of claim 1 reversibly bound to a nucleic acid.

15. The complex of claim 14, wherein the nucleic acid has a therapeutic effect when administered to a subject.

16. The complex of claim 14, wherein the ratio by weight of the functionalized nanodiamond to the nucleic acid is from about 20:1 to about 50:1 or about 40:1 to about 50:1.

17. A pharmaceutical composition comprising the complex of claim 15 and a carrier.

18. A method for delivering a nucleic acid to a cell, comprising administering a complex of claim 15 to the cell.

19. A method of eliciting an immune response in a subject in need thereof, comprising administering a complex of claim 15 to the subject.

* * * * *